United States Patent
Barnes et al.

(10) Patent No.: US 10,560,643 B2
(45) Date of Patent: Feb. 11, 2020

(54) SYSTEMS AND METHODS FOR HYPERSPECTRAL IMAGING

(71) Applicant: Spectral Image, Inc., Greenwich, CT (US)

(72) Inventors: Michael Barnes, Melbourne, FL (US); Zhihong Pan, Cary, NC (US); Sizhong Zhang, Durham, NC (US)

(73) Assignee: Spectral Image, Inc., Melbourne, FL (US)

( * ) Notice: Subject to any disclaimer, the term of this patent is extended or adjusted under 35 U.S.C. 154(b) by 1101 days.

(21) Appl. No.: 14/800,597

(22) Filed: Jul. 15, 2015

(65) Prior Publication Data
US 2016/0080665 A1 Mar. 17, 2016

Related U.S. Application Data

(63) Continuation of application No. 12/370,557, filed on Feb. 12, 2009, now Pat. No. 9,117,133.
(Continued)

(51) Int. Cl.
*A61B 5/00* (2006.01)
*H04N 5/33* (2006.01)
(Continued)

(52) U.S. Cl.
CPC .......... *H04N 5/332* (2013.01); *A61B 5/0059* (2013.01); *A61B 5/0064* (2013.01);
(Continued)

(58) Field of Classification Search
CPC .... H04N 5/332; H04N 5/2351; H04N 5/2256; H04N 5/238; G06K 9/2018;
(Continued)

(56) References Cited

U.S. PATENT DOCUMENTS 4,807,622 A 2/1989 Ohkaka et al.
4,817,622 A 4/1989 Pennypacker et al.
(Continued)

OTHER PUBLICATIONS

Chan et al., 2007, "Imaging with Terahertz Radiation," Rep. Prog. Phys. 70: 1325-1379.
(Continued)

*Primary Examiner* — Peter Luong
(74) *Attorney, Agent, or Firm* — Brett A. Lovejoy; Andrew J. Antczak; Morgan, Lewis & Bockius LLP

(57) ABSTRACT

An apparatus for analyzing a subject including a hyperspectral image module is provided. It is used to identify a suspect region of a subject by using a hyperspectral sensor (for obtaining a hyperspectral image of the subject), a control computer including a processor unit (PU) and a computer readable memory (CRM) (for controlling and is in electronic communication with the sensor), a control software module including instructions stored in the CRM and executed by the PU (for controlling said at least one operating parameter of the sensor), a spectral calibrator module including instructions stored in the CRM and executed by the PU (for applying a wavelength dependent spectral calibration standard constructed for the sensor to a hyperspectral image), and a light source for illuminating the subject. An optional contact probe module is used to collect a signal of the suspect region for medical diagnosis.

16 Claims, 16 Drawing Sheets

Related U.S. Application Data

(60) Provisional application No. 61/073,527, filed on Jun. 18, 2008.

(51) Int. Cl.
  *G06T 7/00* (2017.01)
  *G06K 9/20* (2006.01)
  *H04N 5/225* (2006.01)
  *H04N 5/235* (2006.01)
  *H04N 5/238* (2006.01)

(52) U.S. Cl.
  CPC .......... *A61B 5/0075* (2013.01); *A61B 5/0077* (2013.01); *A61B 5/417* (2013.01); *A61B 5/442* (2013.01); *A61B 5/444* (2013.01); *A61B 5/445* (2013.01); *A61B 5/7246* (2013.01); *A61B 5/7267* (2013.01); *A61B 5/742* (2013.01); *G06K 9/2018* (2013.01); *G06T 7/0012* (2013.01); *H04N 5/2256* (2013.01); *H04N 5/238* (2013.01); *H04N 5/2351* (2013.01); *A61B 5/726* (2013.01); *G06K 2209/05* (2013.01); *G06T 2207/30088* (2013.01); *G06T 2207/30096* (2013.01)

(58) Field of Classification Search
  CPC .............. G06K 2209/05; G06T 7/0012; G06T 2207/30096; G06T 2207/30088; A61B 5/7246; A61B 5/0077; A61B 5/742; A61B 5/0075; A61B 5/7267; A61B 5/0064; A61B 5/0059; A61B 5/445; A61B 5/444; A61B 5/442; A61B 5/417; A61B 5/726
  See application file for complete search history.

(56) References Cited

U.S. PATENT DOCUMENTS

| | | | |
|---|---|---|---|
| 5,772,593 A | 6/1998 | Hakamata | |
| 5,782,770 A | 7/1998 | Mooradian et al. | |
| 5,969,754 A | 10/1999 | Zeman | |
| 6,118,935 A | 9/2000 | Samworth | |
| 6,236,880 B1 | 5/2001 | Raylman et al. | |
| 6,422,508 B1 | 7/2002 | Barnes | |
| 6,427,022 B1 | 7/2002 | Craine et al. | |
| 6,556,858 B1 | 4/2003 | Zeman | |
| 6,640,130 B1 | 10/2003 | Freeman et al. | |
| 6,640,132 B1 | 10/2003 | Freeman et al. | |
| 6,741,884 B1 | 5/2004 | Freeman et al. | |
| 6,810,279 B2 | 10/2004 | Mansfield et al. | |
| 6,828,558 B1 | 12/2004 | Arnone et al. | |
| 6,937,885 B1 | 8/2005 | Lewis et al. | |
| 6,957,099 B1 | 10/2005 | Arnone et al. | |
| 7,013,172 B2 | 3/2006 | Mansfield et al. | |
| 7,239,909 B2 | 7/2007 | Zeman | |
| D566,283 S | 4/2008 | Brafford et al. | |
| 2002/0070341 A1 | 6/2002 | Toomey | |
| 2003/0123056 A1 | 7/2003 | Barnes et al. | |
| 2004/0010196 A1 | 1/2004 | Wang et al. | |
| 2005/0018987 A1 | 1/2005 | Ruf et al. | |
| 2005/0205667 A1 | 9/2005 | Rowe | |
| 2005/0256745 A1 | 11/2005 | Dalton | |
| 2005/0270528 A1 | 12/2005 | Geshwind et al. | |
| 2006/0017922 A1 | 1/2006 | Lewis et al. | |
| 2006/0028643 A1 | 2/2006 | Gottlieb et al. | |
| 2006/0072109 A1 | 4/2006 | Bodkin et al. | |
| 2006/0082762 A1 | 4/2006 | Leverette et al. | |
| 2006/0122515 A1 | 6/2006 | Zeman et al. | |
| 2006/0153262 A1 | 7/2006 | Barbieri et al. | |
| 2006/0210132 A1 | 9/2006 | Christiansen et al. | |
| 2007/0016079 A1 | 1/2007 | Freeman et al. | |
| 2007/0024946 A1* | 2/2007 | Panasyuk ............. | A61B 5/0059 359/253 |
| 2007/0046956 A1 | 3/2007 | Burlingame | |
| 2007/0156038 A1 | 7/2007 | Zeman et al. | |
| 2007/0158569 A1 | 7/2007 | Zeman | |
| 2007/0161906 A1 | 7/2007 | Zeman et al. | |
| 2007/0161907 A1 | 7/2007 | Goldman et al. | |
| 2007/0224694 A1 | 9/2007 | Puchalski | |
| 2007/0249913 A1 | 10/2007 | Freeman et al. | |
| 2007/0268485 A1 | 11/2007 | Polonskly | |
| 2008/0004533 A1 | 1/2008 | Jansen et al. | |
| 2008/0045818 A1 | 2/2008 | Wood | |
| 2008/0046217 A1 | 2/2008 | Polonskly | |
| 2008/0080755 A1 | 4/2008 | Payonk et al. | |
| 2009/0137908 A1 | 5/2009 | Patwardhan | |
| 2012/0274896 A1 | 11/2012 | Vermeer et al. | |
| 2015/0051498 A1 | 2/2015 | Darty | |

OTHER PUBLICATIONS

Chen et al., 2005, "Development of a Thermal and Hyperspectral Imaging System for Wound Characterization and Metabolic Correlation," Johns Hopkins APL Technical Digest 26:67-74.

Donner et al., 2006, "A Spectral Shading Model for Human Skin," International Conference on Computer Graphics and Interactive Techniques. ACM SIGGRAPH 2006 Sketches, 1 page.

Dawes-Higgs et al., Accuracy and reliability of a dynamic biomechanical skin measurement probe for the analysis of stiffness and viscoelasticity., Physiol Meas. Feb. 2004;25(1 ):97-105.

Khaodhiar et al., 2007, "The Use of Medical Hyperspectral Technology to Evaluate Microcirculatory Changes in Diabetic Foot Ulcers and to Predict Clinical Outcomes," Diabetes Care 30:903-910.

Krishnaswamy, 2005, "BioSpec: A Biophysically-Based Spectral Model of Light Interaction with Human Skin," Thesis presented to the University of Waterloo, 83 pages.

Mittleman el al., 1999, "Recent Advances in Terahertz Imaging," Appl. Phys. B, 10 pages.

Nakao et al., 1995, "Real-time Multi-spectral Image Processing for Mapping Pigmentation in Human Skin," Proc. Ninth IS&T/SID Color Imaging Conference, IS&T, 7 pages.

N.p. (Apr. 12, 2004). "How many types of cancers are there?." Medical News Today. Retrieved from http://www.medicalnewstoday.com/releases/7193.php.

Yang et al , 2003, "A CCD Camera-based Hyperspectral Imaging System for Stationary and Airborne Applications," Geocarto International 18(2):71-80.

\* cited by examiner

| Hyperspectral information | 844 |
| --- | --- |
| Subject data record 1 | 846-1 |
|     Subject identifier | 848-1 |
|     Subject demographic information | 850-1 |
|     Hyperspectral data cube 1 | 852-1-1 |
|     ⋮ | |
|     Hyperspectral data cube M | 852-1-M |
|     Optional THz sensor output 1 | 854-1-1 |
|     ⋮ | |
|     Optional THz sensor output M | 854-1-M |
|     Optional conventional image 1 | 856-1-1 |
|     ⋮ | |
|     Optional conventional image M | 856-1-M |
|     Hyperspectral image 1 | 858-1-1 |
|     ⋮ | |
|     Hyperspectral image M | 858-1-M |
|     Clinical characterization 1 | 860-1-1 |
|     ⋮ | |
|     Clinical characterization M | 860-1-M |
|     Diagnosis 1 | 862-1-1 |
|     ⋮ | |
|     Diagnosis M | 862-1-M |
|     Treatment 1 | 864-1-1 |
|     ⋮ | |
|     Treatment M | 864-1-M |
|     Other data | 866-1 |
|     ⋮ | |
| Subject data record N | 846-N |
|     ⋮ | |

Fig. 8B

SYSTEMS AND METHODS FOR HYPERSPECTRAL IMAGING

This application is a continuation of U.S. patent application Ser. No. 12/370,557, filed Feb. 12, 2009, which claims priority to U.S. Provisional Patent Application No. 61/073,527, filed Jun. 18, 2008, and entitled "Systems and Methods for Hyperspectral Medical Imaging," the entire contents of which are hereby incorporated by reference herein.

FIELD OF THE APPLICATION

This application generally relates to systems and methods for medical imaging.

BACKGROUND

Affecting more than one million Americans each year, skin cancer is the most prevalent form of cancer, accounting for nearly half of all new cancers reported, and the number is rising. However, according to the American Academy of Dermatology, most forms of skin cancer are almost always curable when found and treated early. For further details, see A. C. Geller et al., "The first 15 years of the American Academy of Dermatology skin cancer screening programs: 1985-1999," Journal of the American Academy of Dermatology 48(1), 34-41 (2003), the entire contents of which are hereby incorporated by reference herein. As the number of subjects diagnosed with skin cancer continues to rise year-by-year, early detection and delineation are increasingly useful.

During a conventional examination, dermatologists visually survey the skin for lesions or moles that fit certain pre-defined criteria for a potential malignant condition. If an area is suspect, the doctor will perform a biopsy, sending the tissue to a pathology lab for diagnosis. Though effective, this method of detection is time consuming, invasive, and does not provide an immediate definitive diagnosis of a suspect lesion. It is also vulnerable to false positives which introduce unnecessary biopsy and associated costs. More importantly, early detection is very difficult at best, as developing cancers are not usually visible without close inspection of the skin.

Medical imaging has the potential to assist in the detection and characterization of skin cancers, as well as a wide variety of other conditions.

Hyperspectral medical imaging is useful because, among other things, it allows information about a subject to be obtained that is not readily visible to the naked eye. For example, the presence of a lesion may be visually identifiable, but the lesion's actual extent or what type of condition it represents may not be discernable upon visual inspection, or for that matter whether the lesion is benign or cancerous. Although tentative conclusions about the lesion can be drawn based on some general visual indicators such as color and shape, generally a biopsy is needed to conclusively identify the type of lesion. Such a biopsy is invasive, painful, and possibly unnecessary in cases where the lesion turns out to be benign.

In contrast, hyperspectral medical imaging is a powerful tool that significantly extends the ability to identify and characterize medical conditions. "Hyperspectral medical imaging" means utilizing multiple spectral regions to image a subject, e.g., the entire body or a body part of a human or animal, and thus to obtain medical information about that subject. Specifically, each particular region of a subject has a unique spectral signature extending across multiple bands of the electromagnetic spectrum. This spectral signature contains medical, physiological, and compositional information about the corresponding region of the subject. For example, if the subject has a cancerous skin lesion, that lesion may have a different color, density, and/or composition than the subject's normal skin, thus resulting in the lesion having a different spectrum than the normal skin. While these differences may be difficult to visually detect with the naked eye, the differences may become apparent through spectroscopic analysis, thus allowing the lesion (or other medical condition resulting in a measurable spectroscopic feature) to be identified, characterized, and ultimately more readily treated than would be possible using conventional visual inspection and biopsy. Such spectral differences can be presented to a user (such as a physician), for example, by constructing a two-dimensional image of the lesion. See, for example, U.S. Pat. No. 6,937,885, the entire contents of which are hereby incorporated by reference.

However, the potential applicability of conventional systems and methods for hyperspectral medical imaging has been limited by the types of sensors and analytical techniques used. What are needed are more powerful and robust systems and methods for collecting, analyzing, and using hyperspectral information to diagnose and treat subjects.

SUMMARY

Embodiments of the application provide systems and methods of spectral medical imaging. Alternative embodiments of the application also provide systems and methods of analysis by a contact probe based on a result from the prior spectral medical imagine analysis.

One aspect provides a method of hyperspectral medical imaging for diagnosing a medical condition of a subject. One embodiment provides an apparatus for analyzing the skin of a subject comprising (i) a hyperspectral sensor for obtaining a hyperspectral image of the subject, (ii) a control computer for controlling the hyperspectral sensor, where the control computer is in electronic communication with the hyperspectral sensor and where the control computer controls at least one operating parameter of the hyperspectral sensor, and where the control computer comprises a processor unit and a computer readable memory, (iii) a control software module, stored in the computer readable memory and executed by the processor unit, the control software comprising instructions for controlling the at least one operating parameter of the hyperspectral sensor, (iv) a spectral calibrator module, stored in the computer readable memory and executed by the processor unit, the spectral calibrator module comprising instructions for applying a wave-length dependent spectral calibration standard constructed for the hyperspectral sensor to a hyperspectral image collected by the hyperspectral sensor, and (v) a light source that illuminates the skin of the subject for the hyperspectral sensor.

Under another aspect, an apparatus for analyzing the skin of a subject includes: a hyperspectral sensor for obtaining a hyperspectral image of the subject; a control computer for controlling the hyperspectral sensor, where the control computer is in electronic communication with the hyperspectral sensor and where the control computer controls at least one operating parameter of the hyperspectral sensor, and where the control computer includes a processor unit and a computer readable memory; a control software module, stored in the computer readable memory and executed by the processor unit, the control software including instructions for controlling the at least one operating parameter of the hyperspectral sensor; a spectral calibrator module, stored in the computer readable memory and executed by the processor unit, the spectral calibrator module including instructions for applying a wavelength dependent spectral calibration standard constructed for the hyperspectral sensor to a hyperspectral image collected by the hyperspectral sensor; and a light source that illuminates the skin of the subject for the hyperspectral sensor.

In some embodiments, the at least one operating parameter is a sensor control, an exposure setting, a frame rate, or an integration rate. In some embodiments, a power to the light source is controlled by the control software module. In some embodiments, the apparatus further includes one or more batteries for powering the hyperspectral sensor, the control computer and the light source, where the apparatus is portable. In some embodiments, the apparatus further includes a scan mirror to provide simulated motion for a hyperspectral scan of the skin of the subject. In some embodiments, the light source includes a polarizer. In some embodiments, the hyperspectral sensor includes a cross polarizer. In some embodiments, the hyperspectral includes a sensor head, and the control software module includes instructions for moving the sensor head through a range of distances relative to the subject, including a first distance that permits a wide field view of a portion of the subject's skin, and a second distance that permits a detailed view of a portion of the subject's skin. In some embodiments, the hyperspectral sensor is mounted on a tripod. In some embodiments, the tripod is a fixed sensor tripod or a fixed sensor tripod on wheels. In some embodiments, the hyperspectral sensor is mounted on a mobile rack. In some embodiments, the hyperspectral sensor can be mounted on one or more of a scanning bed and an articulated arm. Alternatively, the hyperspectral sensor can be handheld and include fiber optics that are manually moved to obtain reflected light from different portions of the subject.

In some embodiments, the apparatus further includes: a plurality of signatures, each signature in the plurality of signatures corresponding to a characterized human lesion; and a spectral analyzer module stored in the computer readable memory, the spectral analyzer module including instructions for comparing a spectrum acquired using the hyperspectral sensor to a signature in the plurality of signatures. In some embodiments, the apparatus further includes a trained data analysis algorithm, stored in the computer readable memory, for identifying a region of the subject's skin of biological interest using an image obtained by the apparatus. In some embodiments, the trained data analysis algorithm is a trained neural network, a trained support vector machine, a decision tree, or a multiple additive regression tree. In some embodiments, the apparatus further includes a trained data analysis algorithm, stored in the computer readable memory, for characterizing a region of the subject's skin of biological interest using an image obtained by the apparatus. In some embodiments, the trained data analysis algorithm is a trained neural network, a trained support vector machine, a decision tree, or a multiple additive regression tree. In some embodiments, the apparatus further includes a trained data analysis algorithm, stored in the computer readable memory, for determining a portion of a hyperspectral data cube that contains information about a biological insult in the subject's skin. In some embodiments, the trained data analysis algorithm is a trained neural network, a trained support vector machine, a decision tree, or a multiple additive regression tree.

In some embodiments, the apparatus further includes: a storage module, stored in the computer readable media, where the storage module includes a plurality of spectra of the subject's skin taken at different time points; and an analysis module, stored in the computer readable media, where the analysis module includes instructions for using the plurality of spectra to form a normalization baseline of the skin. In some embodiments, the different time points span one or more contiguous years. In some embodiments, the analysis module further includes instructions for analyzing the plurality of spectra to determine a time when a biological insult originated. In some embodiments, the biological insult is a lesion.

In some embodiments, the apparatus further includes a sensor other than a hyperspectral sensor. In some embodiments, the other sensor is a digital camera, a LIDAR sensor, or a terahertz sensor. In some embodiments, the apparatus further includes a fusion module, stored in the computer readable memory, for fusing an image of a portion of the skin of the subject from the other sensor and an image of a portion of the skin of the subject from the hyperspectral sensor. In some embodiments, the fusion module includes instructions for color coding or greyscaling data from the image of a portion of the skin of the subject from the hyperspectral sensor onto the image of a portion of the skin of the subject from the other sensor. In some embodiments, the fusion module includes instructions for color coding or greyscaling data from the image of a portion of the skin of the subject from the other sensor onto the image of a portion of the skin of the subject from the hyperspectral sensor. In some embodiments, the fusion module includes instructions for color coding or greyscaling data from the image of a portion of the skin of the subject from the other sensor as well as color coding or greyscaling data from the image of a portion of the skin of the subject from the hyperspectral sensor.

Some embodiments further include an integrated display for displaying data from the hyperspectral sensor and a value of the at least one operating parameter that is controlled by the control computer. In some embodiments, the integrated display further displays the probabilistic presence of a biological insult to the skin of the subject.

Some embodiments further include a spectral analyzer module, stored in the computer readable media, where the spectral analyzer module includes instructions for determining a boundary of an image of a biological insult in the hyperspectral image. In some embodiments, the boundary of the image of the biological insult is manually determined by a user. In some embodiments, the boundary of the image of the biological insult is determined by a trained data analysis algorithm. Some embodiments further segments the image of the biological insult into multiple segments. Some embodiments further include a communications module, the communications module including instructions for communicating the boundary of the image of the biological insult to a local or remote computer over a network connection. In some embodiments, the communications module further includes instructions for communicating a frame of reference of the skin of the subject with the boundary of the image of the biological insult to the local or remote computer over the network connection.

Under another aspect, a method of diagnosing a medical condition in a subject, the subject having a plurality of regions, includes: obtaining light from each region of the plurality of regions without regard to any visible characteristics of the plurality of regions; resolving the light obtained from each region of the plurality of regions into a corresponding spectrum; based on a stored spectral signature corresponding to the medical condition, obtaining a probability that each spectrum includes indicia of the medical condition being present in the corresponding region; if the probability exceeds a pre-defined threshold, displaying an indicator representing the probable presence of the medical condition in the corresponding region.

Under another aspect, a method of diagnosing a medical condition in subject, the subject having a plurality of regions, includes: resolving light obtained from each region of the plurality of regions into a corresponding spectrum; based on a stored spectral signature corresponding to the medical condition, obtaining a probability that each spectrum includes indicia of the medical condition being present in the corresponding region; if the probability exceeds a first pre-defined threshold, displaying an indicator representing the probable presence of the medical condition in the corresponding region; accepting user input setting a second pre-defined threshold; and if the probability exceeds the second pre-defined threshold, displaying an indicator representing the probable presence of the medical condition in the corresponding region.

Under another aspect, a method of diagnosing a medical condition in subject, the subject having a plurality of regions, includes: resolving light obtained from each region of the plurality of regions into a corresponding spectrum; based on a stored spectral signature corresponding to the medical condition, obtaining a probability that each spectrum includes indicia of the medical condition being present in the corresponding region; if the probability exceeds a first pre-defined threshold, displaying an indicator representing the probable presence of the medical condition in the corresponding region, and displaying at least one of a type of the medical condition, a category of the medical condition, an age of the medical condition, a boundary of the medical condition, and a new area of interest for examination.

Under another aspect, a method of diagnosing a medical condition in a subject includes: at a first distance from the subject, obtaining light from each region of a first plurality of regions of the subject; resolving the light obtained from each region of the first plurality of regions into a corresponding spectrum; based on a spectral characteristic present in a subset of the first plurality of regions, determining a second distance from the subject allowing for closer examination of the subset; at a second distance from the subject, obtaining light from each region of a second plurality of regions of the subject, the second plurality of regions including the subset; resolving the light obtained from each region of the second plurality of regions into a corresponding spectrum; based on a stored spectral signature corresponding to the medical condition, obtaining a probability that each spectrum includes indicia of the medical condition being present in the corresponding region; and if the probability exceeds a pre-defined threshold, displaying an indicator representing the probable presence of the medical condition in the corresponding region.

Under another aspect, a method of characterizing a medical condition in a subject, the subject having a plurality of regions, includes: at a first time, resolving light obtained from each region of the plurality of regions into a corresponding spectrum; storing the spectra corresponding to the first time; at a second time subsequent to the first time, resolving light obtained from each region of the plurality of regions into a corresponding spectrum; based on a comparison of the spectra corresponding to the second time to the spectra corresponding to the first time, determining that the medical condition had been present at the first time although it had not been apparent at the first time; and displaying an indicator representing the probable presence of the medical condition in the subject.

One alternative embodiment provides an apparatus for analyzing the skin of a subject comprising (i) a hyperspectral sensor for obtaining a hyperspectral image of the subject, (ii) a control computer for controlling the hyperspectral sensor, where the control computer is in electronic communication with the hyperspectral sensor and where the control computer controls at least one operating parameter of the hyperspectral sensor, and where the control computer comprises a processor unit and a computer readable memory, (iii) a control software module, stored in the computer readable memory and executed by the processor unit, the control software comprising instructions for controlling the at least one operating parameter of the hyperspectral sensor, (iv) a spectral calibrator module, stored in the computer readable memory and executed by the processor unit, the spectral calibrator module comprising instructions for applying a wave-length dependent spectral calibration standard constructed for the hyperspectral sensor to a hyperspectral image collected by the hyperspectral sensor, (v) a light source that illuminates the skin of the subject for the hyperspectral sensor, and (vi) a contact probe module in electronic communication with the control computer, where the contact probe module is configured to measure a region of interest of the skin of the subject that is identified based on an aspect of the hyperspectral image, and where the contact probe module comprises a first probe head unit connected to a handle unit.

In some alternative embodiments, the contact probe module further comprises a connector unit connected to the handle unit. In some alternative embodiments, the first probe head unit is configured to obtain a signal from a region of interest of the skin of the subject, where the signal is an electrical, a magnetic, a thermal, a mechanical, a radiometric, a photometric, or an optical signal. In some alternative embodiments, the handle unit is configured to receive the first probe head unit and a second probe head unit, where the first probe head unit is a different type of probe head than the second probe head unit. In some alternative embodiments, the first probe head unit is an electrical probe, a magnetic probe, a thermal probe, a mechanical probe, a radiometric probe, a photometric probe or an optical probe. In some alternative embodiments, the contact probe module is configured to obtain more than one type of signal from the region of interest of the skin of the subject. In some alternative embodiments, the contact probe module is configured to measure at least a first type of signal and a second type of signal, where the first type of signal is different than the second type of signal. In some alternative embodiments, the contact probe module is configured to measure the region of interest of the skin of the subject at a plurality of different times.

One alternative aspect provides a method of diagnosing a medical condition of a subject using a contact probe module, the subject having a plurality of regions of skin of interest, the method comprising: (A) obtaining light from each region of skin in the plurality of regions of skin of interest; (B) resolving light obtained in the obtaining (A) from each region of skin in the plurality of regions of skin into a corresponding spectrum using a hyperspectral module, thereby constructing a plurality of spectra; (C) identifying a suspect region of skin in the plurality of regions of skin by obtaining a first indication that a first spectrum in the plurality of spectra that corresponds to the suspect region includes an indicia of the medical condition being present in the suspect region; (D) collecting, after the identifying (C), a measurement of the suspect region using the contact probe module thereby obtaining a second indication that the medical condition is present in the suspect region, where the contact probe module is configured to obtain a signal from the suspect region; and (E) outputting an indicator representing the presence of the medical condition in the suspect region to a user, a user interface device, or a monitor; or outputting an indicator representing the presence of the medical condition in the suspect region in user readable form to a computer readable storage medium or a local or remote computer system; or displaying an indicator representing the presence of the medical condition in the suspect region. In some embodiments, the light has been previously obtained and stored in the alternative hyperspectral apparatus.

In some alternative embodiments, the first indication is made based on a comparison between the first spectrum and a stored predetermined spectral signature corresponding to the medical condition and where the stored predetermined spectral signature is obtained from a region that is known to have the medical condition. In some alternative embodiments, the first indication is made based on a comparison between the first spectrum and a stored predetermined spectral signature corresponding to the medical condition and where the first indication is made when the first spectrum shares a similarity to the stored predetermined spectral signature. In some alternative embodiments, the similarity is determined based on a similarity metric computed between the first spectrum and the stored predetermined spectral signature. In some alternative embodiments, the first indication is made based on a comparison between the first spectrum and a stored predetermined spectral signature corresponding to the medical condition and where the second indication is made when the signal from the suspect region shares a similarity to the stored measurement signature. In some alternative embodiments, the similarity is determined based on a similarity metric computed between the signal from the suspect region and the stored measurement signature. In some embodiments, the first indication is made based on a comparison between the first spectrum and a stored predetermined spectral signature corresponding to the medical condition. In some alternative embodiments, the second indication is made based on comparison between the measurement and a stored measurement signature corresponding to the medical condition. In alternative some embodiments, the signal is an electrical signal, a magnetic signal, a thermal signal, a mechanical signal, or an optical signal.

BRIEF DESCRIPTION OF DRAWINGS

FIG. 8B illustrates an exemplary database of spectral information for one or more subjects, according to some embodiments.

DETAILED DESCRIPTION

Embodiments of the application provide systems and methods for spectral medical imaging.

Specifically, the present application provides systems and methods that enable the diagnosis of a medical condition in a subject using spectral medical imaging data obtained using any combination of sensor such as a LIDAR sensor, a thermal imaging sensor, a millimeter-wave (microwave) sensor, a color sensor, an X-ray sensor, a UV sensor, a NIR sensor, a SWIR sensor, a MWIR sensor, a LWIR sensor, and/or a hyperspectral image sensor. For example, a hyperspectral image of the subject can be obtained by irradiating a region of the subject with a light source, and collecting and spectrally analyzing the light from the subject. An image that maps the spectrally analyzed light onto visible cues, such as false colors and/or intensity distributions, each representing spectral features that include medical information about the subject is then generated based on the spectral analysis. Those visible cues, the hyperspectral image, can be displayed in "real time" (that is, preferably with an imperceptible delay between irradiation and display), allowing for the concurrent or contemporaneous inspection of both the subject and the spectral information about the subject. From this, a diagnosis can be made and a treatment plan can be developed for the subject.

Optionally, the spectral image includes not only the visible cues representing spectral information about the subject, but also other types of information about the subject. For example, a conventional visible-light image of the subject can be obtained, and the spectral information overlaid on that conventional image in order to aid in correlation between the spectral features and the regions that generated those features. Or, for example, information can be obtained from multiple types of sensors (e.g., LIDAR, color, thermal, THz) and that information combined with the hyperspectral image, thus concurrently providing different, and potentially complementary types of information about the subject. Based on information in the hyperspectral image and/or from other types of sensors, one or more sensors or analytical parameters can be modified and new images obtained, in order to more accurately make a diagnosis.

First, an overview of methods of making a medical diagnosis will be provided. Then, a system for spectral medical imaging will be described in detail. Then, various potential applications of spectral medical imaging will be described. Lastly, some examples of other embodiments will be described. The described methods, systems, applications, and embodiments are intended to be merely exemplary, and not limiting.

1. Overview of Methods

Figure 1A:
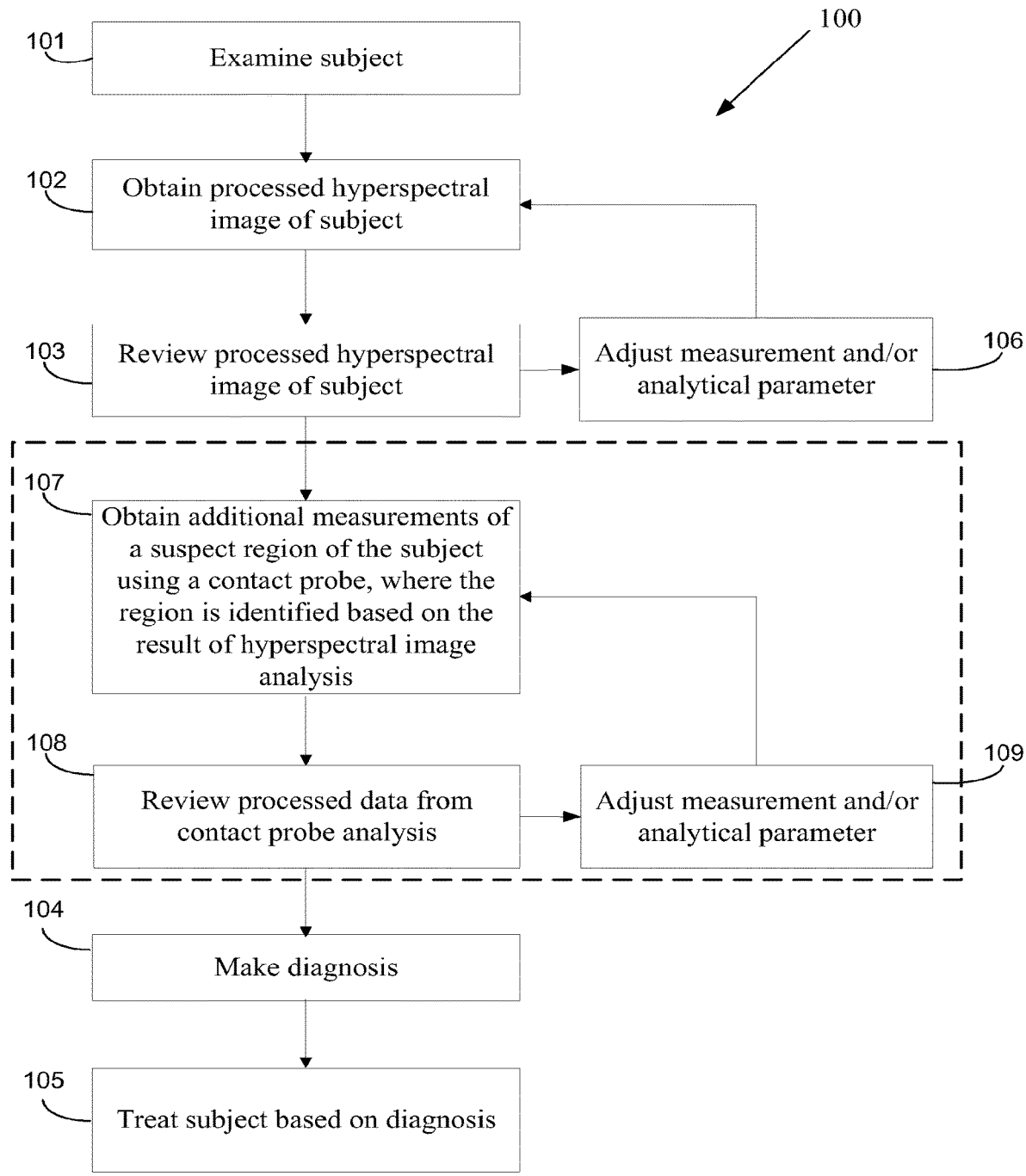
FIG. 1A illustrates a method for diagnosing a subject using spectral medical imaging, according to some embodiments. Steps in the dashed rectangle depict alternative embodiments that include use of a contact probe.

FIG. 1A illustrates an overview of a method 100 of making a medical diagnosis using medical imaging. First, a subject is examined (101). The examination can include visually observing, smelling, and/or touching the subject, as is conventionally done in medical examinations. A particular area of the subject's skin may be focused on, based on the subject's complaints and/or based on observations made of the subject.

Then, a spectral image of the subject (102) is taken, for example, an image of a particular area of the subject's skin of interest. In some embodiments, the particular area of the subject comprises several different contiguous or non-contiguous regions of the subject's skin. As described in greater detail below, in some embodiments, this image is a hyperspectral image that is obtained by irradiating the subject with light, collecting and analyzing light from the subject, and constructing a processed hyperspectral image based on the results of the analysis. Optionally, obtaining a hyperspectral image also includes obtaining other types of information about the subject, such as images in specific spectral bands (e.g., a THz image), and fusing or otherwise combining that information with the hyperspectral image.

The processed image(s) are reviewed (103), for example, to determine whether the image(s) contain any information indicating that the subject has a medical condition. Based on the results of the review, a suspect region is identified among the plurality of regions as a region with an indication that the data collected at the particular region include an indicia of a medical condition (e.g., an indicia for skin melanoma may be a particular type of a skin lesion and/or coloration that may correspond to the type of skin melanoma). Measurements from the plurality of regions may be processed according to methods such as clustering analysis, principal component analysis or any analytic methods that are suitable for processing such measurements. In some embodiments, the measurements are normalized before any analytical processing is performed.

In some embodiments, the indication for the suspect region is obtained by comparing measurements from one or more of the plurality of regions with one or more spectral signatures in a library of spectral signatures, in which each spectral signature in the library corresponds to one or more spectral characteristics of a medical condition. In some embodiments, the suspect region is identified when the comparison results in a region that most resembles a spectral signature from the spectral signature library. Results from such a comparison can be represented by a similarity metric, such as a ratio or a similarity matrix. Examples of similarity metrics are reviewed in McGill et al., 1979, "An evaluation of factors affecting document ranking by information retrieval systems," Project report, Syracuse University School of Information Studies, which is hereby incorporated herein by reference. In particular, Table 2 of McGill et at list 67 different exemplary similarity metrics that can be used to compare measurements from one or more of the plurality of regions with a spectral signature in a library of spectral signatures. If the similarity metrics is above a certain value, the corresponding region will be identified as the suspect region. For example, a region can be identified as a suspect region when the similarity metric between the region and a spectral signature for a medical condition is, e.g., a ratio of 0.4 or above, 0.5 or above, 0.6 or above, 0.7 or above, 0.8 or above, 0.9 or above, where 1.0 represents complete identity between the region and the spectral signature of the medical condition. It will be understood by one of skill of the art that the threshold for the similarity metric can differ with respect to the type of tissues under analysis. For example, it may be more difficult obtaining signals for a certain type of tissues such that the signal to noise ratio for the particular tissue may be low; thus ultimately resulting in a low similarity metrics value. In some embodiments, measurements of the plurality of regions are resolved into spectra where each spectrum corresponds to a region. The spectrum corresponding to a region is then compared to a signature spectrum corresponding to a medical condition. The signature spectrum is obtained by taking measurements of a region that is known to have the medical condition. It will be understood by one of skill in the art that any suitable analytical methods can be used for obtaining the spectral signature of the medical condition.

To compute a similarity metric (e.g., a correlation coefficient) between measurements from the plurality of regions with one or more spectral signatures in a library of spectral signatures, any number of techniques can be used. For example, a plurality of features can be calculated from the measurements of a region in the plurality of regions. These same features can be calculated from the spectral signatures. One example of the feature is an observed or recorded intensity at a particular wavelength. Another example of a feature is the ratio of one observed or recorded intensity at one particular wavelength divided by another observed or recorded intensity at another particular wavelength. Another example of a feature is some mathematical function of two or more observed or recorded intensities at unique wavelengths. Exemplary mathematical functions include, but are not limited to monomial and polynomial functions (e.g., binomial functions, quadratic functions, trinomial function, etc.) of any degree greater than zero (e.g., the linear function $f(x)=a*(x)+b$ given above where the value $\lfloor a*(x) \rfloor$ is taken for $a*(x)$), rational functions $$\left(e.g., R(x) = \frac{a_n x^n + a_{n-1} x^{n-1} + \ldots + a_1 x + a_o}{b_n x^n + b_{n-1} x^{n-1} + \ldots + b_1 x + b_o}\right),$$

exponential functions (e.g., exponential decay or exponential growth), power functions (e.g., $f(x)=ax^p$, where a and p are real numbers), power series (e.g., a power series on variable x), or any combination thereof. In this way, five or more, ten or more, twenty or more, or one hundred or more features can be calculated from each hyperspectral image. The values of these features can then be used as the basis for computing a similarity between such images.

In some embodiments, more than one spectral signature may be identified that corresponds to one medical condition. Also, more than one spectral signature may be identified that corresponds to more than one medical condition. In some embodiments, adjustments are made to the measurements and/or analytical parameters (106) that control the imaging in order to obtain (102) one or more new or modified spectral images of the subject with improved quality. The new or modified spectral images of the subject may be used to identify a suspect region for analysis by an alternative hyperspectral apparatus which comprises a contact probe module (107-109). It will be understood that a contact probe module is an apparatus to be used in conjunction with a hyperspectral module disclosed herein and that any methods of data collection and data analysis that apply the hyperspectral apparatus would also apply to the hyperspectral apparatus with a contact probe module. In some embodiments, more than one suspect region is identified and subjected to subsequent analyses. As shown in FIG. 1A, it will be understood that an exemplary embodiment as outlined in steps 107-109 is additional and optional to the main hyperspectral imaging process.

In some alternative embodiments, the suspect region is identified in a previous spectral analysis such that only measurements of the suspect region will be taken using the contact probes disclosed herein.

In alternative embodiments, after a suspect region is identified, a contact probe module is used to obtain additional data of the suspect region (107). In some alternative embodiments, the contact probe provides the same type of characterization of the suspect region as the original hyperspectral image analysis, but at a higher resolution or with improved signal quality. In some alternative embodiments, the contact probe provides one or more different types of characterizations of the suspect region such that an additional different type of data measurement is obtained. The additional data is processed at step 108. In some embodiments, information obtained from the additional data is used to modify the previously obtained hyperspectral images. In some alternative embodiments, information obtained from the additional data is used to augment the previously obtained hyperspectral images. It is understood that additional procedures may be applied to the suspect region prior to collecting the additional data. For example, the suspect region may be cleaned (e.g., using rubbing alcohol) or processed (e.g., using a specific dye for detecting the presence of specific biological markers).

In some alternative embodiments, additional steps may be taken with respect to the patient or subject prior to analysis by contact probes. For example, the patient or subject may be subject to ultraviolet light or infrared light, or an agent may be injected to the suspect site that will facilitate the contact probe analysis.

In some alternative embodiments, the data obtained by contact probes at 107 is used to create a separate image. In some alternative embodiments, the separate image is then fused to the previously obtained hyperspectral image. In some embodiments, the separate image is used to augment the information obtained from the original hyperspectral image.

It will be understood that measurements obtained of the suspect region are compared with a known measurement signature which corresponds to a medical condition. Advantageously, the measurements obtained of the suspect region are processed before any comparison is made. As described hereinabove, results from such comparison can be represented by a similarity metrics. If the similarity metrics is above a certain value, the suspect region will be identified as having a certain medical condition. For example, a suspect region will be determined as having a medical condition when the similarity metric between the suspect region and a measurement signature for a medical condition is, e.g., a ratio of 0.4 or above, 0.5 or above, 0.6 or above, 0.7 or above, 0.8 or above, 0.9 or above, where 1.0 represents complete identity between measurements of the suspect region and the measurement signature of the medical condition. It will be understood by one of skill of the art that the threshold for the similarity metric can differ with respect to the type of tissues under analysis. For example, it may be more difficult obtaining signals for a certain type of tissues such that the signal to noise ratio for the particular tissue may be low; thus ultimately resulting in a low similarity metric value.

In some embodiments, a medical condition can be a skin lesion that is associated with a skin cancer, a tumor, or an internal injury. An indicator for a medical condition can be any biological or chemical marker the presence or change of which suggests the presence of a disease. For example, signals corresponding to changes of heme concentrations in the blood may be used to diagnose whether a patient has malaria or other diseases that involved changes of heme concentrations in blood. An indicia for a medical condition can be, for example, the concentration of biological or chemical marker has exceeded a threshold value, suggesting that a medical condition is present.

In the case where the image is a fusion of a hyperspectral image with another spectral source and the image indicates the presence of a medical condition, a parameter of the hyperspectral imaging process can be altered in order to attempt to observe the medical condition, e.g., by seeing what spectral features are present at wavelengths other than those originally measured, or by seeing the area or a subset of the area with different spatial and/or spectral resolutions.

In some embodiments, repeat measurements may be taken at the hyperspectral stage (102) and the data are averaged to reduce experimental errors. In alternative embodiments, repeat measurements may be taken at the contact probe stage (107) and the data are averaged to reduce experimental errors. In still alternative embodiments, repeat measurements may be taken at both the hyperspectral stage (102) and the contact probe stage (107), and the data are averaged to reduce experimental errors.

In some alternative embodiments, measurements each corresponding to a single time point are taken at either the hyperspectral stage or the contact probe stage. In some alternative embodiments, measurements at (corresponding to) a plurality of time points are taken at either the hyperspectral stage or the contact probe stage. For example, a video of hyperspectral images of a subject may be created by monitoring the patient or subject over a period of time. The video images may be taken at a time lag separated by milliseconds, seconds, minutes, hours or days so long as such time lag enables a practitioner to formulate a quality characterization of the subject or patient. Similarly, a video or video representation of measurements of the suspect region may be also created by monitoring the suspect region over a period of time. The measurements may be taken at a time lag separated by milliseconds, seconds, minutes, hours or days so long as such time lag enables a practitioner to formulate a quality characterization of the suspect region. In some alternative embodiments, the subject or the suspected region may be prepared prior to data analysis by the contact probe. For example, the subject may be dosed with a certain dose of agent or reagent to facilitate analysis by the contact probe, or alternatively, the suspect region may be cleaned to allow better data collection.

In some alternative embodiments, the same type of data is collected at the hyperspectral image stage (102) and at the contact probe stage (107) of a suspect region of the subject. In some alternative embodiments, the data collected at the contact probe stage (107) of a suspect region on the subject is different than the type of data that is collected at the hyperspectral image stage (102). For example, in one embodiment the data that is obtained at the contact probe stage (107) is the type of data disclosed in U.S. Pat. No. 5,042,494, which is hereby incorporated by reference herein in its entirety. U.S. Pat. No. 5,042,494 discloses a method and an apparatus for detecting the presence of cancerous tissue using native visible luminescence. The tissue to be examined is excited with a beam of light that causes the tissue to fluoresce over a spectrum of wavelengths. The intensity at which the excited tissue fluoresces can be measured is either over a spectrum or at a predetermined number of preselected wavelengths. One can determine the carcinomatoid status of a tissue by determining the wavelength(s) at which maximum intensity(ies) are attained for the tissue in question and by comparing these peak wavelengths, either visually or electronically, to the peak wavelength(s) derived from a known non-cancerous tissue. Alternatively, one can also determine the carcinomatoid status of a tissue by comparing the luminescence spectrum of the excited tissue with the luminescence spectrum of a known non-cancerous tissue and/or known cancerous tissue or the excitation spectra of the excited tissue with the excitation spectra of known cancerous and/or known non-cancerous tissue, one can determine the carcinomatoid status of the tissue in question.

In another example, in one alternative embodiment the data obtained at the contact probe stage (107) is the type of data disclosed in U.S. Pat. No. 5,131,398, which is also hereby incorporated by reference herein in its entirety. U.S. Pat. No. 5,131,398 discloses a method and apparatus for distinguishing cancerous tumor tissues from benign tumor tissue or normal tissue using native fluorescence. The tissue to be examined is excited with a beam of monochromatic light at 300 nanometers (nm). The intensity of the native fluorescence emitted from the tissue is measured at 340 and 440 nm. A ratio of the two intensities is then calculated and used as a basis for determining if the tissue is cancerous as opposed to benign or normal.

In some alternative embodiments, adjustments are made to measurements or analytical parameter(s) for the contact probes before additional measurements are taken of the suspect region. The additional measurements are then used to improve the result from the earlier contact probe analysis.

In some alternative embodiments, data from the contact probe analysis step 108 may lead to the conclusion that the initial hyperspectral image analysis 103 needs to be modified. Accordingly, modifications of measurements and/or analytical parameters can be made and, based on these modifications, the hyperspectral data collection 102 and/or hyperspectral image data analysis 103 and/or the additional measurements 107 coupled with contact probe analysis step 108 repeated one or more times. For example, in some embodiments, contact probe analysis step 108 may lead to redefining the suspect region. Thus, in such embodiments, the redefined suspect region may be subject to additional measurements 102 and/or 107 with the concomitant review 103 or analysis 108. In some embodiments, modification can be made to the existing suspect region such that the existing suspect region is enlarged, reduced or altered. Review step 108 may be performed using methods similar to those used in the process for identifying one or more suspect regions. For example, another indication may be identified by comparing measurements obtained of the suspect region at step 107 with a library of spectral signature library where the spectral signature library contains a plurality of spectral signatures each corresponding to a medical condition. When different types of data are collected for the plurality of regions and for the suspect region, a different type of signature library can be used during the comparison analysis for the suspect region.

In some embodiments, the additional data obtained with the contact probes are combined with data from hyperspectral analysis (e.g., a hyperspectral image) for further analysis before a diagnosis of the subject is made. In some embodiments, such analysis is carried out by comparing the data from the hyperspectral image or from the contact probe with existing signatures of signals that correspond to known illnesses or medical conditions.

It will be understood by one of ordinary skill in the art that any analytical methods known in the art may be used to process the data obtained either at the hyperspectral stage 102 or at the alternative and additional contact probe stage 107. Exemplary methods for data analysis can be found hereinbelow.

After a diagnosis of the subject is made (104) based on the first spectral image, or one or more subsequent images, the subject is subjected to a treatment plan based on that diagnosis (105). For example, if the subject is diagnosed with a cancerous lesion that is not readily apparent to the naked eye but that has boundaries observable in the hyperspectral medical image, the treatment plan may call for the excision of the lesion based on the boundaries shown in the hyperspectral medical image.

Figure 1B:
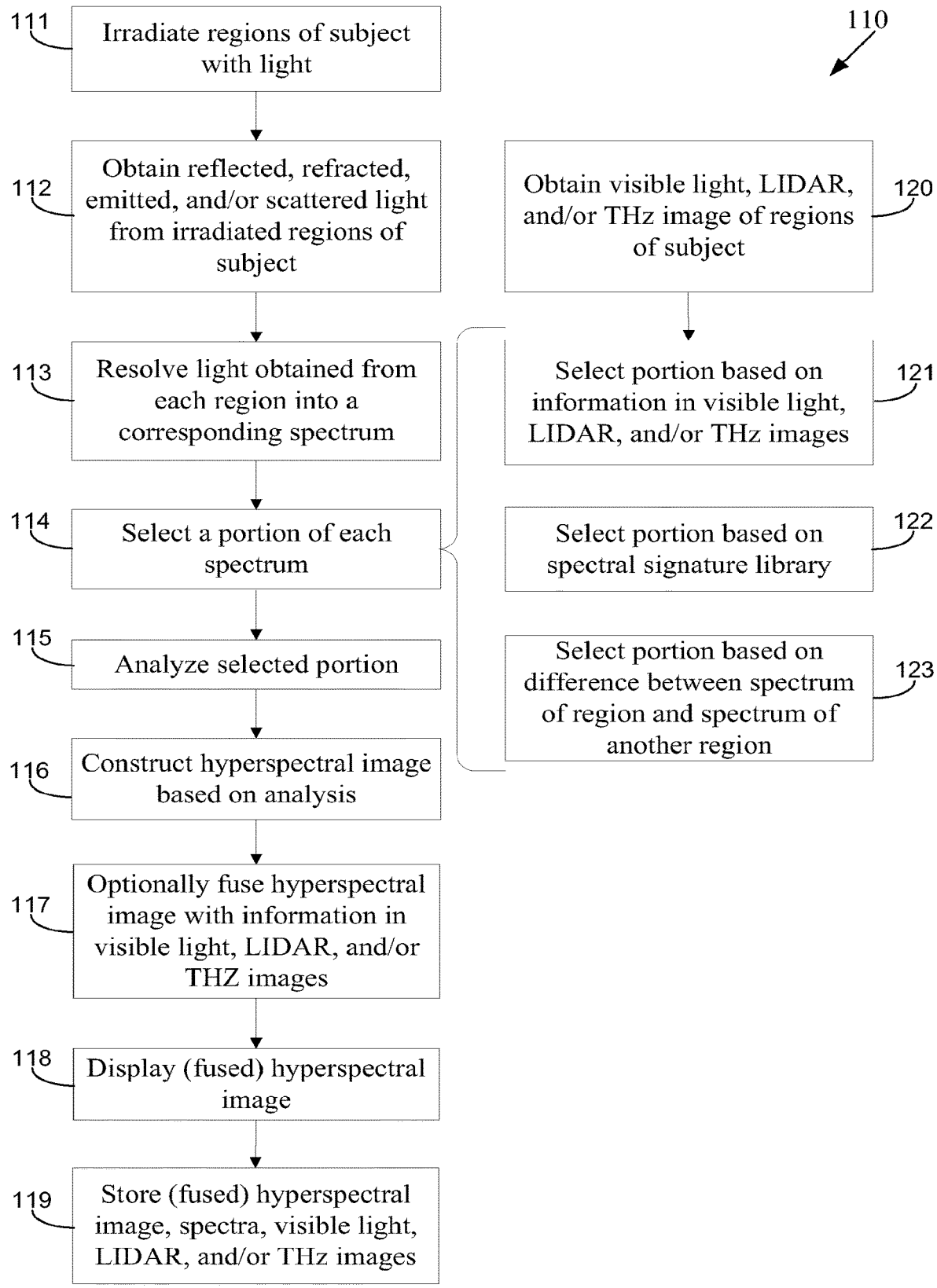
FIG. 1B illustrates a method for obtaining a spectral image of a subject, according to some embodiments.

FIG. 1B illustrates a method 110 of obtaining a hyperspectral medical image of a subject for use in diagnosis (for example, at step 103 of the method of FIG. 1A), according to some embodiments.

First, each of a plurality of regions of the subject is irradiated with light (111). The regions may collectively represent an area identified as being of interest due to the subject's complaints or by visual inspection. Collectively, the regions of the subject can include, for example, a portion of one of the subject's body parts, an entire body part, multiple body parts, or the entire subject. However, each individual region may be quite small, e.g., less than 10 centimeters in area, or less than 1 centimeter in area, or less than 100 millimeters in area, or less than 10 millimeters in area, or less than 1 millimeter in area, or less than 100 microns in area. Usefully, each individual region is sufficiently small to allow resolution of the medical feature of interest, that is, so that a specified region containing the medical feature can be distinguished from other regions that do not contain the feature. Different options for the source and spectral content of the light are described in greater detail below.

Next, light is obtained from the regions of the subject (112). Depending on the interactions between the regions of the subject and the spectrum of light with which they are irradiated, the light may be reflected, refracted, absorbed, and/or scattered from the regions of the subject. In some embodiments, one or more regions of the subject may even emit light, e.g., fluoresce or photoluminesce in response to irradiation with the light. A lens, mirror, or other suitable optical component can be used to obtain the light from the regions of the subject, as described in greater detail below.

The light obtained from each region is then resolved into a corresponding spectrum (113). For example, the light obtained from each region can be passed into a hyperspectral sensor. The hyperspectral sensor includes a diffraction grating or other dispersive optical component that generates a spatial separation between the light's component wavelengths. This spatial separation allows the relative intensities of the component wavelengths in the spectrum to be obtained and recorded, e.g., using a detector such as a charge-coupled device (CCD) or other appropriate sensor that generates a digital signal representing the spectrum. The relative intensities of the component wavelengths can be calibrated (for example, as described below) to obtain the absolute intensities of those wavelengths, which are representative of the actual physical interaction of the light with the subject. The calibrated digital signal of each spectrum can be stored, e.g., on tangible computer readable media or in tangible random access memory.

A portion of each spectrum is then selected (114). This portion selection can be based on one or more of several different types of information. For example, the portion can be selected based on a spectral signature library (122), which contains information about the spectral characteristics of one or more predetermined medical conditions, physiological features, or chemicals (e.g., pharmaceutical compounds). These spectral characteristics can include, for example, pre-determined spectral regions that are to be selected in determining whether the subject has a particular medical condition. Or, for example, the portion can be selected based on a spectral difference between the spectrum of that region and the spectrum of a different region (123). For example, a cancerous region will have a different spectrum than will a normal region, so by comparing the spectra of the two regions the presence of the cancer can be determined. The portion can also, or alternatively, be selected based on information in other types of images of the regions (121). As discussed in greater detail below, visible light, LIDAR, THz, and/or other types of images can be obtained of the regions (120). These images may include information that indicates the presence of a certain medical condition. For example, if a darkened region of skin is observed in a visible light image, the portion of the spectrum can be selected so as to include information in some or all of the visible light band. Further details on systems and methods of selecting portions of spectra, and of obtaining other types of images of the subject, are provided below.

The selected portions of the spectra are then analyzed (115), for example, to determine whether the selected portions contain spectral peaks that match those of a pre-determined medical condition. Optionally, steps 114 and 115 are performed in reverse order. For example, the spectra can be compared to that of a pre-determined medical condition, and then portions of the compared spectra selected, as described in greater detail below.

A hyperspectral image based on the selected portion of each spectrum is then constructed (116). The image includes information about the relative intensities of selected wavelengths within the various regions of the subject. The image can represent the spectral information in a variety of ways. For example, the image may include a two-dimensional map that represents the intensity of one or more selected wavelengths within each region of the subject. Such image can be monochromatic, with the intensity of the map at a given region based on the intensity of the selected wavelengths (e.g., image intensity directly proportional to light intensity at the selected wavelengths). Alternately, the image can be colorful, with the color of the map at a given region based on the intensity of the selected wavelengths, or indices deducted from the selected wavelengths (for example, a value representative of the ratio between the value of a peak in a spectrum and the value of a peak in a spectrum of a medical condition). Although the image may represent information from one or more non-visible regions of the electromagnetic spectrum (e.g., infrared), the image is visible so that it can be viewed by a physician or other interested party.

The hyperspectral image is optionally combined or "fused" with other information about the subject (117). For example, the hyperspectral image can be overlaid on a conventional visible-light image of the subject. Also, or alternatively, the image can be combined with the output of other types of sensors, such as LIDAR and/or THz sensors. Systems and methods for generating "fused" hyperspectral images are described in greater detail below.

The hyperspectral image, which is optionally fused with other information, is then displayed (118). For example, the image can be displayed on a video display and/or can be projected onto the subject, as is described in greater detail in U.S. Provisional Patent Application No. 61/052,934, filed May 13, 2008 and entitled "Systems and Methods for Hyperspectral Medical Imaging Using Real-Time Projection of Spectral Information," the entire contents of which are hereby incorporated by reference herein. In embodiments in which the image is projected onto the subject, the regions of the image corresponding to regions of the subject are projected directly, or approximately directly, onto those regions of the subject. This allows for the concurrent or contemporaneous inspection of the physical regions of the subject on the subject as well as on an imaging device such as a computer monitor. This facilitated correlation of those spectral features with physical features of the subject, thus aiding in the diagnosis and treatment of a medical condition. The delay between obtaining the light and projecting the image onto the subject and/or onto a computer display may be less than about 1 millisecond (ms), less than about 10 ms, less than about 100 ms, less than about 1 second, less than about 10 seconds, or less than about 1 minute. In some embodiments, the image is a fused image while in other embodiments the image is a hyperspectral image.

In embodiments in which the spectral image is displayed on a video display, the image can be inspected, optionally while the subject is being examined, thereby facilitating the procurement of information that is useful in diagnosing and treating a medical condition. In some embodiments, a conventional visible light image of the regions of the subject is displayed along with the image containing spectral information to aid in the correlation of the spectral features with physical features of the subject. In some embodiments, the image is both projected onto the subject and displayed on a video monitor.

In some embodiments, the hyperspectral image, the raw spectra, and any other information (such as visible light, LIDAR, and/or THz images) are stored for later processing (119). For example, storing an image of a lesion each time the subject is examined can be used to track the growth of the lesion and/or its response to treatment. Storing the spectra can enable other information to be obtained from the spectra at a later time, as described in greater detail below.

2. Systems for Hyperspectral Medical Imaging

Figure 2A:
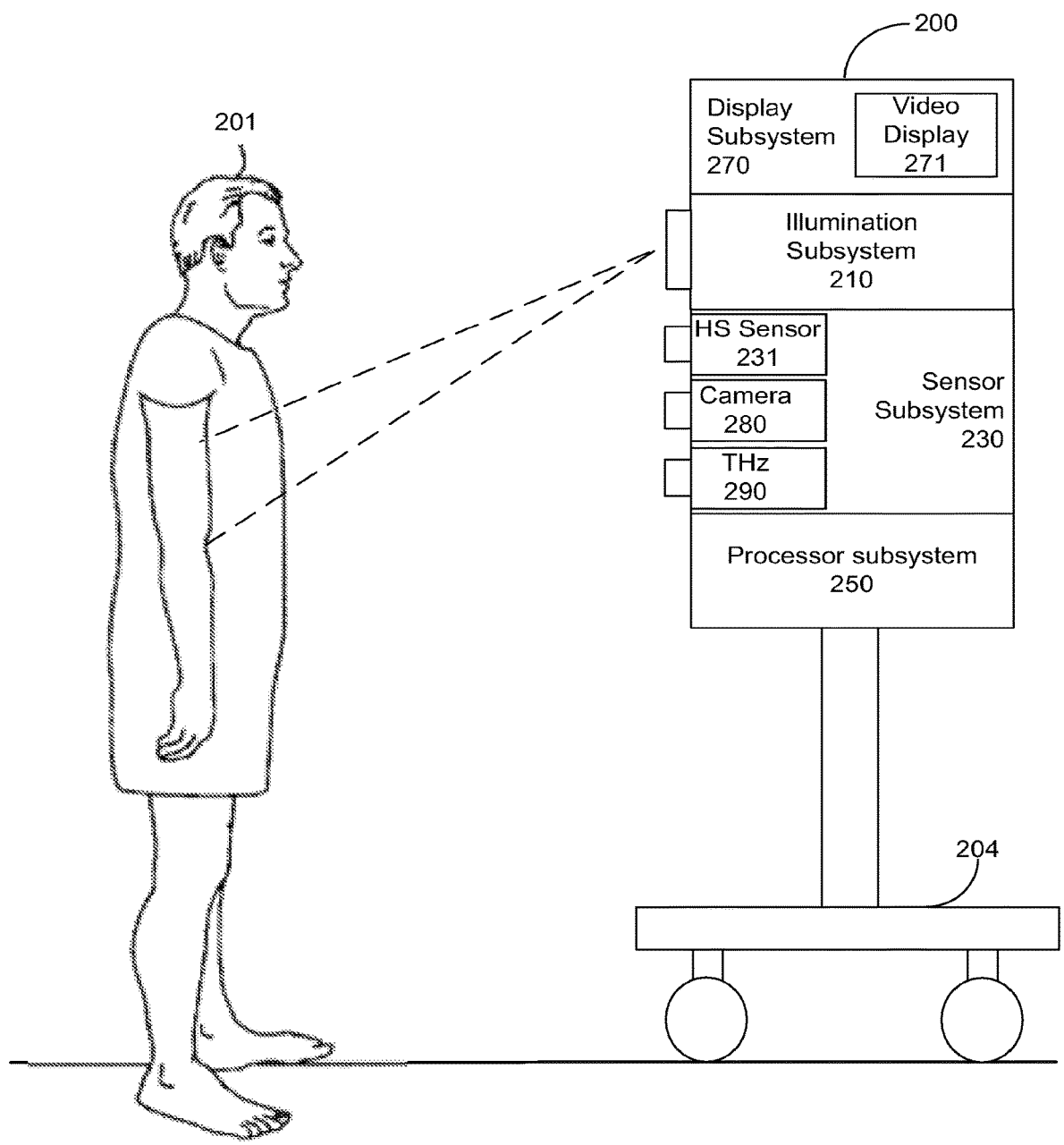
FIG. 2A schematically illustrates a system for spectral medical imaging, according to some embodiments.

FIG. 2A illustrates an exemplary embodiment of a hyperspectral medical imaging system 200 that is mounted on a cart 204. The system 200 can be mounted on the cart 204 using, for example, a tripod, a post, a rack, or can be directly mounted to the cart. The cart 204 includes wheels that allow system 200 to be readily moved relative to subject 201, thus enabling the system 200 to obtain hyperspectral images of different parts of the subject's body without requiring the subject to move. In some embodiments, the system 200 can be moved closer to the subject 201 in order to obtain more detailed images of parts of the subject's body (e.g., for diagnostic purposes), and can be moved further away from the subject 201 in order to obtain a wider view of the subject's body (e.g., for screening purposes). Alternatively, the system 200 includes zooming optics that enable closer or wider views of the subject 201 to be imaged without requiring the system to be physically moved closer to or away from the subject. In another embodiment (not shown), the sensor is fixed in place (e.g., is mounted on a tripod), but includes rotatable mirrors and/or can itself be rotated, enabling different parts of the subject 201 to be imaged without moving the sensor relative to the subject, and zooming optics for varying how close a view of the subject is imaged.

The subject 201 is illustrated as standing, but the subject could generally be in any suitable position, for example, lying down, sitting, bending over, etc. In some embodiments, the system 200 is instead mounted on a scanning bed and/or on an articulated arm. Alternatively, the system 200 can be handheld and include fiber optics that are manually moved to obtain reflected light from different portions of the subject.

The system 200 includes an illumination subsystem 210 for irradiating the subject 201 with light (illustrated as dashed lines); a sensor subsystem 230 that includes a hyperspectral sensor (HS Sensor) 231, a camera 280, and a THz sensor 290, a processor subsystem for analyzing the outputs of the sensor subsystem 230 and generating a fused hyperspectral image, and a display subsystem 270 that includes a video display 271 for displaying the fused hyperspectral image in real-time, and optionally also includes a projector (not shown) for projecting the fused hyperspectral image onto the subject 201.

Figure 2B:
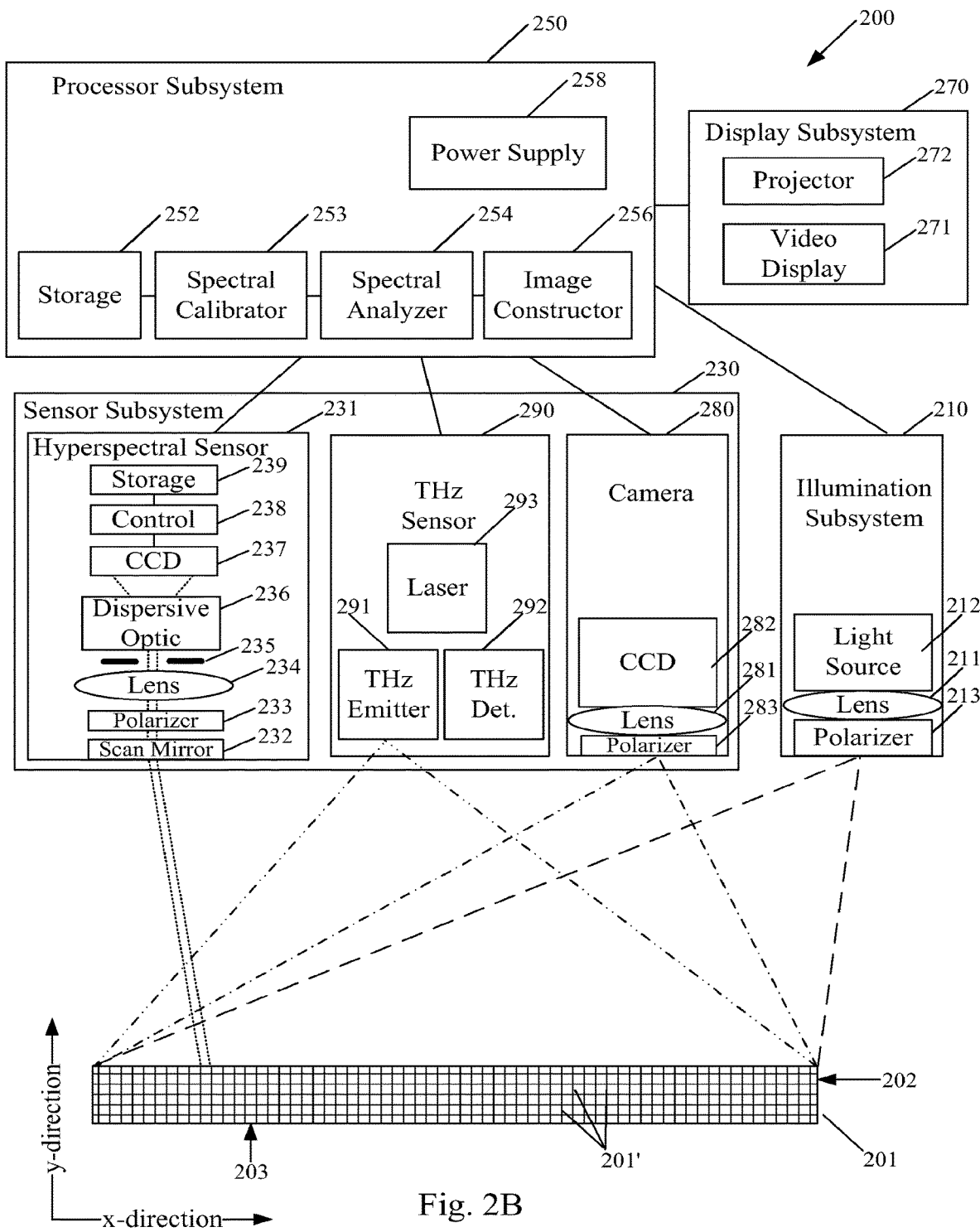
FIG. 2B schematically illustrates components of a system for spectral medical imaging, according to some embodiments.

FIG. 2B schematically illustrates the components of the hyperspectral medical imaging system 200 of FIG. 2A, according to some embodiments. In FIG. 2B, the subject is represented as an area 201 that includes a plurality of regions 201', which are illustrated as a plurality of small squares. The area 201 can be one of the subject's body parts or a portion thereof (e.g., a selected area of the subject's skin), can be multiple body parts or portions thereof, or can even be the entire subject. The plurality of regions 201' are subsets of area 201. The regions 201' need not be directly adjacent one another, and need not be square, or even regularly shaped. The regions 201' collectively represent a sampling of the area 201 that is to be characterized. In the illustrated embodiment, the regions 201' are organized into rows 202 and columns 203 of regions. The subject is, of course, not considered to be part of the imaging system.

As discussed above, the hyperspectral imaging system 200 includes an illumination subsystem 210, a sensor subsystem 230, a processor subsystem 250, and a display subsystem 270. The processor subsystem 250 is in operable communication with each of the illumination, sensor, and display subsystems, and coordinates the operations of these subsystems in order to irradiate the subject, obtain spectral information from the subject, construct an image based on the spectral information, and display the image. Specifically the illumination subsystem 210 irradiates with light each region 201' within area 201 of the subject, which light is represented by the dashed lines. The light interacts with the plurality of regions 201' of the subject. The sensor subsystem 230 collects light from each region of the plurality of regions 201' of the subject, which light is represented by the dotted lines. The hyperspectral sensor 231 within sensor subsystem 230 resolves the light from each region 201' into a corresponding spectrum, and generates a digital signal representing the spectra from all the regions 201'. The processor subsystem 250 obtains the digital signal from the sensor subsystem 230, and processes the digital signal to generate a hyperspectral image based on selected portions of the spectra that the digital signal represents. The processor optionally fuses the hyperspectral image with information obtained from the camera 280 (which collects light illustrated as dash-dot lines) and/or the THz sensor 290 (which collects light illustrated as dash-dot-dot lines) The processor subsystem 250 then passes that image to projection subsystem 270, which displays the image.

Each of the subsystems 210, 230, 250, and 270 will now be described in greater detail.

A. Illumination Subsystem

Illumination subsystem 210 includes a light source 212, a lens 211, and polarizer 213.

The light source 212 generates light having a spectrum that includes a plurality of component wavelengths. The spectrum can include component wavelengths in the X-ray band (in the range of about 0.01 nm to about 10 nm); ultraviolet (UV) band (in the range of about 10 nm to about 400 nm); visible band (in the range of about 400 nm to about 700 nm); near infrared (NIR) band (in the range of about 700 nm to about 2500 nm); mid-wave infrared (MWIR) band (in the range of about 2500 nm to about 10 µm); long-wave infrared (LWIR) band (in the range of about 10 µm to about 100 µm); terahertz (THz) band (in the range of about 100 µm to about 1 mm); or millimeter-wave band (also referred to as the microwave band) in the range of about 1 mm to about 300 mm, among others. The NIR, MWIR, and LWIR are collectively referred to herein as the infrared (IR) band. The light can include a plurality of component wavelengths within one of the bands, e.g., a plurality of wavelengths in the NIR band, or in the THz. Alternately, the light can include one or more component wavelengths in one band, and one or more component wavelengths in a different band, e.g., some wavelengths in the visible, and some wavelengths in the IR. Light with wavelengths in both the visible and NIR bands is referred to herein as "VNIR." Other useful ranges may include the region 1,000-2,500 nm (shortwave infrared, or SWIR).

The light source 212 includes one or more discrete light sources. For example, the light source 212 can include a single broadband light source, a single narrowband light source, a plurality of narrowband light sources, or a combination of one or more broadband light source and one or more narrowband light source. By "broadband" it is meant light that includes component wavelengths over a substantial portion of at least one band, e.g., over at least 20%, or at least 30%, or at least 40%, or at least 50%, or at least 60%, or at least 70%, or at least 80%, or at least 90%, or at least 95% of the band, or even the entire band, and optionally includes component wavelengths within one or more other bands. A "white light source" is considered to be broadband, because it extends over a substantial portion of at least the visible band. By "narrowband" it is meant light that includes components over only a narrow spectral region, e.g., less than 20%, or less than 15%, or less than 10%, or less than 5%, or less than 2%, or less than 1%, or less than 0.5% of a single band. Narrowband light sources need not be confined to a single band, but can include wavelengths in multiple bands. A plurality of narrowband light sources may each individually generate light within only a small portion of a single band, but together may generate light that covers a substantial portion of one or more bands, e.g., may together constitute a broadband light source.

One example of a suitable light source 212 is a diffused lighting source that uses a halogen lamp, such as the Lowel Pro-Light Focus Flood Light. A halogen lamp produces an intense broad-band white light which is a close replication of daylight spectrum. Other suitable light sources 212 include a xenon lamp, a hydrargyrum medium-arc iodide lamp, and/or a light-emitting diode. In some embodiments, the light source 212 is tunable. Other types of light sources are also suitable. In some embodiments, a standard or custom filter is used to balance the light intensities at different wavelengths to raise the signal level of certain wavelength. For examples, a blue filter can be used to increase the relative intensity of blue lights for which the sensor has a low sensitivity. Such filters could also be used with a foreoptic (e.g., the lens) of the hyperspectral sensor.

Depending on the particular light source 212 used, the relative intensities of the light's component wavelengths are uniform (e.g., are substantially the same across the spectrum), or vary smoothly as a function of wavelength, or are irregular (e.g., in which some wavelengths have significantly higher intensities than slightly longer or shorter wavelengths), and/or can have gaps. Alternatively, the light can include one or more narrow-band spectra in regions of the electromagnetic spectrum that do not overlap with each other.

The light from light source 212 passes through lens 211, which modifies the focal properties of the light (illustrated as dashed lines) so that it illuminates regions 201' of the subject. In some embodiments, lens 211 is selected such that illumination subsystem 210 substantially uniformly irradiates regions 201' with light. That is, the intensity of light at one region 201' is substantially the same as the intensity of light at another region 201'. In other embodiments, the intensity of the light varies from one region 201' to the next.

The light then passes through optional polarizer 213, which removes any light that does not have a selected polarization. Polarizer 213 can be, for example, a polarizing beamsplitter or a thin film polarizer. The polarization can be selected, for example, by rotating polarizer 213 appropriately.

Illumination subsystem 210 irradiates regions 201' with light of sufficient intensity to enable sensor subsystem 230 to obtain sufficiently high quality spectra from those regions 201', that is, that a spectrum with a sufficient signal-to-noise ratio can be obtained from each region 201' to be able to obtain medical information about each region 201'. However, in some embodiments, ambient light, such as fluorescent, halogen, or incandescent light in the room, or even sunlight, is a satisfactory source of light. In such embodiments, the illumination subsystem 210 is not activated, or the system may not even include illumination system 210. Sources of ambient light typically do not communicate with the processing subsystem 250, but instead operate independently of system 200.

The light from illumination subsystem 210 (illustrated as the dashed lines in FIG. 2B) interacts with the plurality of regions 201' within area 201. The interaction between the light and each region 201' depends on the particular physiological structure and characteristics of that region. The particular interactions between the light and each individual irradiated region of the subject impart a spectral signature onto the light obtained from that region. This spectral signature can be used to obtain medical information about the subject. Specifically, different regions interact differently with the light depending on the presence of, for example, a medical condition in the region, the physiological structure of the region, and/or the presence of a chemical in the region. For example, fat, skin, blood, and flesh all interact with various wavelengths of light differently from one another. Similarly, a given type of cancerous lesion interacts with various wavelengths of light differently from normal skin, from non-cancerous lesions, and from other types of cancerous lesions. A given chemical that is present (e.g., in the blood, or on the skin) interacts with various wavelengths of light differently from other types of chemicals. Thus, the light obtained from each irradiated region of the subject has a spectral signature based on the characteristics of the region, which signature contains medical information about that region.

For example, the structure of skin, while complex, can be approximated as two separate and structurally different layers, namely the epidermis and dermis. These two layers have very different scattering and absorption properties due to differences of composition. The epidermis is the outer layer of skin. It has specialized cells called melanocytes that produce melanin pigments. Light is primarily absorbed in the epidermis, while scattering in the epidermis is considered negligible. For further details, see G. H. Findlay, "Blue Skin," British Journal of Dermatology 83(1), 127-134 (1970), the entire contents of which are hereby incorporated by reference herein.

The dermis has a dense collection of collagen fibers and blood vessels, and its optical properties are very different from that of the epidermis. Absorption of light of a bloodless dermis is negligible. However, blood-borne pigments like oxy- and deoxy-hemoglobin and water are major absorbers of light in the dermis. Scattering by the collagen fibers and absorption due to chromophores in the dermis determine the depth of penetration of light through skin.

In the visible and near-infrared (VNIR) spectral range and at low intensity irradiance, and when thermal effects are negligible, major light-tissue interactions include reflection, refraction, scattering and absorption. For normal collimated incident radiation, the regular reflection of the skin at the air-tissue interface is typically only around 4%-7% in the 250-3000 nanometer (nm) wavelength range. For further details, see R. R. Anderson and J. A. Parrish, "The optics of human skin," Journal of Investigative Dermatology 77(1), 13-19 (1981), the entire contents of which are hereby incorporated by reference herein. When neglecting the air-tissue interface reflection and assuming total diffusion of incident light after the stratum corneum layer, the steady state VNIR skin reflectance can be modeled as the light that first survives the absorption of the epidermis, then reflects back toward the epidermis layer due the isotropic scattering in the dermis layer, and then finally emerges out of the skin after going through the epidermis layer again.

Using a two-layer optical model of skin, the overall reflectance can be modeled as:

$$R(\lambda) = T_E^2(\lambda) R_D(\lambda),$$

where $T_E(\lambda)$ is the transmittance of epidermis and $R_D(\lambda)$ is the reflectance of dermis. The transmittance due to the epidermis is squared because the light passes through it twice before emerging out of skin. Assuming the absorption of the epidermis is mainly due to the melanin concentration, the transmittance of the epidermis can be modeled as:

$$T_E(\lambda) = \exp(d_E c_m m(\lambda)),$$

where $d_E$ is the depth of the epidermis, $c_m$ is the melanin concentration and $m(\lambda)$ is the absorption coefficient function for melanin. For further details, see S. L. Jacques, "Skin optics," Oregon Medical Laser Center News Etc. (1988), the entire contents of which are hereby incorporated by reference herein.

The dermis layer can be modeled as a semi-infinite homogeneous medium. The *diffuse* reflectance from the surface of dermis layer can be modeled as:

$$R_D(\lambda) = \exp\left(\frac{-A}{\sqrt{3(1+\mu_s(\lambda)/\mu_a(\lambda))}}\right),$$

where constant A is approximately 7-8 for most soft tissues, and $\mu_a(\lambda)$ is the overall absorption coefficient function of the dermis layer. For further details, see S. L. Jacques, "*Diffuse reflectance from a semi-infinite medium*," Oregon Medical Laser News Etc. (1999), the entire contents of which are hereby incorporated by reference herein.

The term $\mu_a(\lambda)$ can be approximated as:

$$\mu_a(\lambda)=c_o o(\lambda)+c_h h(\lambda)+c_w w(\lambda),$$

where $c_o$, $c_h$, and $c_w$ are the concentrations of oxy-hemoglobin, deoxy-hemoglobin and water, respectively, while $o(\lambda)$, $h(\lambda)$, and $w(\lambda)$ are the absorption coefficient functions of oxy-hemoglobin, deoxy-hemoglobin, and water, respectively. For further details, see S. Wray et al., "Characterization of the near infrared absorption spectra of cytochrome aa3 and haemoglobin for the non-invasive monitoring of cerebral oxygenation," Biochimica et Biophysica Acta 933 (1), 184-192 (1988), the entire contents of which are hereby incorporated by reference herein.

The scattering coefficient function for soft tissue can be modeled as:

$$\mu_s(\lambda)=a\lambda^{-b},$$

where a and b depend on the individual subject and are based, in part, on the size and density of collagen fibers and blood vessels in the subject's dermis layer.

From the above equations, for a fixed depth of epidermis layer, the skin reflectance $R(\lambda)$ can be modeled as a function f of seven parameters:

$$R(\lambda)=f(a,b,c_m,c_o,c_h,c_w,\lambda)$$

where a, b, $c_m$, $c_o$, $c_h$, and $c_w$, are as described above. The skin reflectance $R(\lambda)$ may also depend on other variables not listed here. For example, long wavelengths (e.g., in the MWIR, FIR, or THz bands) may interact weakly with the surface of the skin and interact strongly with fat, flesh, and/or bone underlying the skin, and therefore variables other than those discussed above may be relevant.

The value of the skin's reflectance as a function of wavelength, $R(\lambda)$, can be used to obtain medical information about the skin and its underlying structures. For example, when skin cancers like basal cell carcinoma (BCC), squamous cell carcinoma (SCC), and malignant melanoma (MM) grow in the skin, the molecular structure of the affected skin changes. Malignant melanoma is a cancer that begins in the melanocytes present in the epidermis layer. For further details, see "Melanoma Skin Cancer," American Cancer Society (2005), the entire contents of which are hereby incorporated by reference herein. Most melanoma cells produce melanin that in turn changes the reflectance characteristics as a function of wavelength $R(\lambda)$ of the affected skin. Squamous and basal cells are also present in the epidermis layer. The outermost layer of the epidermis is called the stratum corneum. Below it are layers of squamous cells. The lowest part of the epidermis, the basal layer, is formed by basal cells. Both squamous and basal cell carcinomas produce certain viral proteins that interact with the growth-regulating proteins of normal skin cells. The abnormal cell growth then changes the epidermis optical scattering characteristics and consequently the skin reflectance properties as a function of wavelength $R(\lambda)$. Thus, information about different skin conditions (e.g., normal skin, benign skin lesions and skin cancers) can be obtained by characterizing the reflectance $R(\lambda)$ from the skin. This can be done, for example, using the sensor subsystem 230 and processor subsystem 250, as described in greater detail below.

B. Sensor Subsystem

As illustrated in FIG. 2B, the sensor subsystem 230 includes a hyperspectral sensor 231 that obtains light from each region 201' and resolves that light into a corresponding spectrum; a THz sensor 290 that obtains THz light from each region 201' and generates an intensity map representing the intensity of THz light reflected from each region 201'; and a camera 280 that obtains visible light from each region 201' and generates an intensity map representing the intensity of visible light from each region 201' (e.g., a conventional photographic image). The hyperspectral sensor 231, THz sensor 290, and camera 280 will each be discussed in turn.

It should be understood that the THz sensor and camera are optional features of the sensor subsystem 230, and that the sensor subsystem 230 may also or alternatively include other types of sensors, such as a LIDAR sensor (laser detection and ranging), a thermal imaging sensor, a millimeter-wave (microwave) sensor, a color sensor, an X-ray sensor, a UV (ultraviolet) sensor, a NIR (near infrared) sensor, a SWIR (short wave infrared) sensor, a MWIR (mid wave infrared) sensor, or a LWIR (long wave infrared) sensor. Other types of sensors can also be included in sensor subsystem 230, such as sensors capable of making non-optical measurements (e.g., molecular resonance imaging, nuclear magnetic resonance, a dynamic biomechanical skin measurement probe). Some sensors may obtain information in multiple spectral bands. In some embodiments, one or more sensors included in the sensor subsystem 230 are characterized by producing an intensity map of a particular type of radiation from the regions 201', as opposed to producing a spectrum from each region 201', as does the hyperspectral sensor 231. In some embodiments, one or more sensors included in the sensor subsystem 230 in addition to the hyperspectral sensor produce a spectrum that can be analyzed.

In one example, a LIDAR sensor can obtain 3D relief and digitized renderings of the regions 201', which can augment lesion analysis. Physicians conventionally touch a subject's skin while developing their diagnosis, e.g., to determine the physical extent of a lesion based on its thickness. A LIDAR sensor, if used, records the topography of a lesion with an accuracy far exceeding that possible with manual touching. A LIDAR sensor functions by scanning a pulsed laser beam over a surface, and measuring the time delay for the laser pulses to return to the sensor, for each point on the surface. The time delay is related to the topographical features of the surface. For medical imaging, the intensity and color of the laser beam used in the LIDAR sensor is selected so that it does not injure the subject. Conventionally, LIDAR is performed at a relatively large distance from the object being scanned. For example, LIDAR systems can be mounted in an airplane and the topology of the earth measured as the airplane passes over it. While LIDAR sensors that operate at close ranges suitable for medical environments are still in development, it is contemplated that such a sensor can readily be incorporated into sensor subsystem 230. Some examples of sensors suitable for producing 3D topological images of a subject include, but are not limited to, the VIVID 9i or 910 Non-Contact 3D Digitizers available from Konica Minolta Holdings, Inc., Tokyo, Japan, and the Comet IV, Comet 5, T-Scan, and T-Scan 2 scanners available from Steinbichler Optotechnik GmbH, Neubeuern, Germany.

i. Hyperspectral Sensor

Referring to FIG. 2B, the hyperspectral sensor 231 includes a scan mirror 232, a polarizer 233, a lens 234, a slit 235, a dispersive optic 236, a charge-coupled device (CCD) 237, a sensor control subsystem 238, and a storage device 239. It should be understood that the optics can be differently arranged than as illustrated in FIG. 2B (e.g., the optics can be in a different order than shown, optics can be eliminated, and/or additional optics provided).

The scan mirror 232 obtains light from one row 202 of the regions 201' at a time (illustrated as dotted lines in FIG. 2B), and directs that light toward the other optics in the sensor 231 for spectral analysis. After obtaining light from one row 202, the scan mirror 232 then rotates or otherwise moves in order to obtain light from a different row 202. The scan mirror 232 continues this rotation until light has been sequentially obtained from each row 202. Mechanisms other than scan mirrors can be used to scan sequential rows of regions 201' of the subject, such as the focal plane scanner described in Yang et al., "A CCD Camera-based Hyperspectral Imaging System of Stationary and Airborne Applications," Geocarto International, Vol. 18, No. 2, June 2003, the entire contents of which are incorporated by reference herein. In some embodiments (not shown), the hyperspectral sensor 231 instead sequentially obtains light from rows 202 by moving relative the subject, or by the subject moving relative to the sensor.

The light then passes through optional polarizer 233, which removes any light that does not have a selected polarization. Polarizer 233 can be, for example, a polarizing beamsplitter or a thin film polarizer, with a polarization selected, for example, by rotating polarizer 233 appropriately. The polarization selected by polarizer 233 can have the same polarization, or a different polarization, than the polarization selected by polarizer 213. For example, the polarization selected by polarizer 233 can be orthogonal (or "crossed") to the polarization selected by polarizer 213. Crossing polarizers 213 and 233 can eliminate signal contributions from light that does not spectrally interact with the subject (and thus does not carry medical information about the subject), but instead undergoes a simple specular reflection from the subject. Specifically, the specularly reflected light maintains the polarization determined by polarizer 213 upon reflection from the subject, and therefore will be blocked by crossed polarizer 233 (which is orthogonal to polarizer 213). In contrast, the light that spectrally interacts with the subject becomes randomly depolarized during this interaction, and therefore will have some component that passes through crossed polarizer 233. Reducing or eliminating the amount of specularly reflected light that enters the hyperspectral sensor 231 can improve the quality of spectra obtained from the light that spectrally interacted with the subject and thus carries medical information.

In crossed-polarizer embodiments, the intensity of the light that passes through polarizer 233 (namely, the light that becomes depolarized through interaction with the subject) has somewhat lower intensity than it would if polarizers were excluded from the system. The light can be brought up to a satisfactory intensity, for example, by increasing the intensity of light from illumination subsystem 210, by increasing the exposure time of CCD 237, or by increasing the aperture of lens 234. In an alternative embodiment, polarizers 213 and 233 are not used, and specular reflection from the subject is reduced or eliminated by using a "diffuse" light source, which generates substantially uniform light from multiple angles around the subject. An example of a diffuse light source is described in U.S. Pat. No. 6,556,858, entitled "Diffuse Infrared Light Imaging System," the entire contents of which are incorporated by reference herein.

The lens 234 obtains light from polarizer 233, and suitably modifies the light's focal properties for subsequent spectral analysis.

The optional slit 235 then selects a portion of the light from the lens 234. For example, if the scan mirror 232 obtains light from more than one row 202 of regions 201' at a time, and the slit 235 can eliminate light from rows other than a single row of interest 202.

The light is then directed onto dispersive optic 236. The dispersive optic 236 can be, for example, a diffractive optic such as transmission grating (e.g., a phase grating or an amplitude grating) or reflective grating, prism, or other suitable dispersive optic. The dispersive optic 236 spatially separates the different component wavelengths of the obtained light, allowing the intensity of each of the component wavelengths (the spectrum) to be obtained for each region 201' of the selected row 202.

Figure 3A:
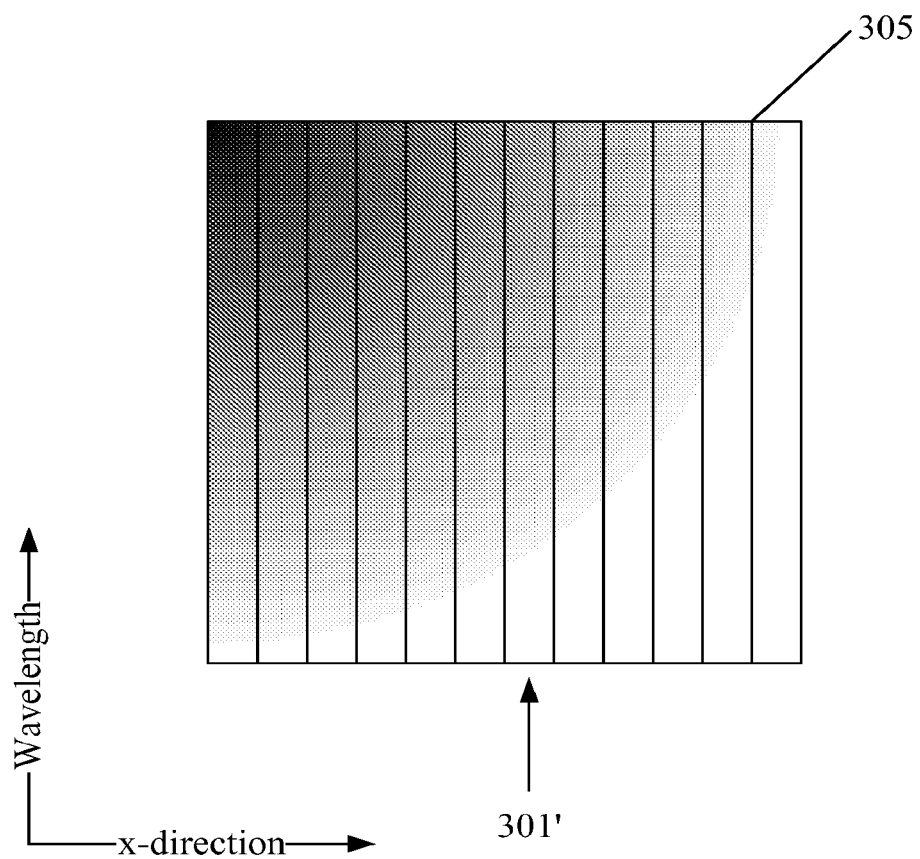
FIG. 3A schematically illustrates a hyperspectral data "plane" including medical information about a subject, according to some embodiments.

FIG. 3A schematically illustrates the resolution of the spectrum of each region 201' in a row 202 into an exemplary "hyperspectral data plane" 305. The plane 305 includes a plurality of columns 301', each of which includes the spectrum of a corresponding region 201'. As FIG. 3A illustrates, the intensity of the spectrum within each column 301' varies as a function of wavelength. This intensity variation is a result of the light's wavelength-dependent interaction with the corresponding region 201' of the subject, and thus contains medical information about that region 201'. For example, using the model described above, the spectrum can be modeled as a wavelength-dependent reflectance $R(\lambda)$ that is a function of several variables, e.g., the concentrations of melanin, oxy-hemoglobin, deoxy-hemoglobin and water. In the illustrated embodiment, a dark color at a given wavelength means less reflection of light from the region 201' (e.g., strong absorption of that wavelength by the region 201', such as due to a high concentration of melanin) and a light color at a given wavelength means more reflection of light from the region 201' (e.g., weak absorption of that wavelength by the region 201', such as due to a low concentration of melanin) Thus, in FIG. 3A the plane 305 indicates that the left-most columns 301' had a relatively high reflection at long wavelengths, which reflects the fact that the left-most regions 201' of row 202 contain different medical information than the right-most regions 201 of row 202.

Under control of the sensor control subsystem 238, the CCD 237 senses and records the intensity of each of the component wavelengths (the spectrum) from each region 201' of row 202 the form of a digital signal, such as a hyperspectral data plane. In some embodiments, the sensor control subsystem 238 stores the plane in storage device 239. Storage device 239 can be volatile (e.g., RAM) or non-volatile (e.g., a hard disk drive). The hyperspectral sensor 231 then sequentially obtains additional planes 305 for the other rows 202, and storing the corresponding planes 305 in storage 239.

Figure 3B:
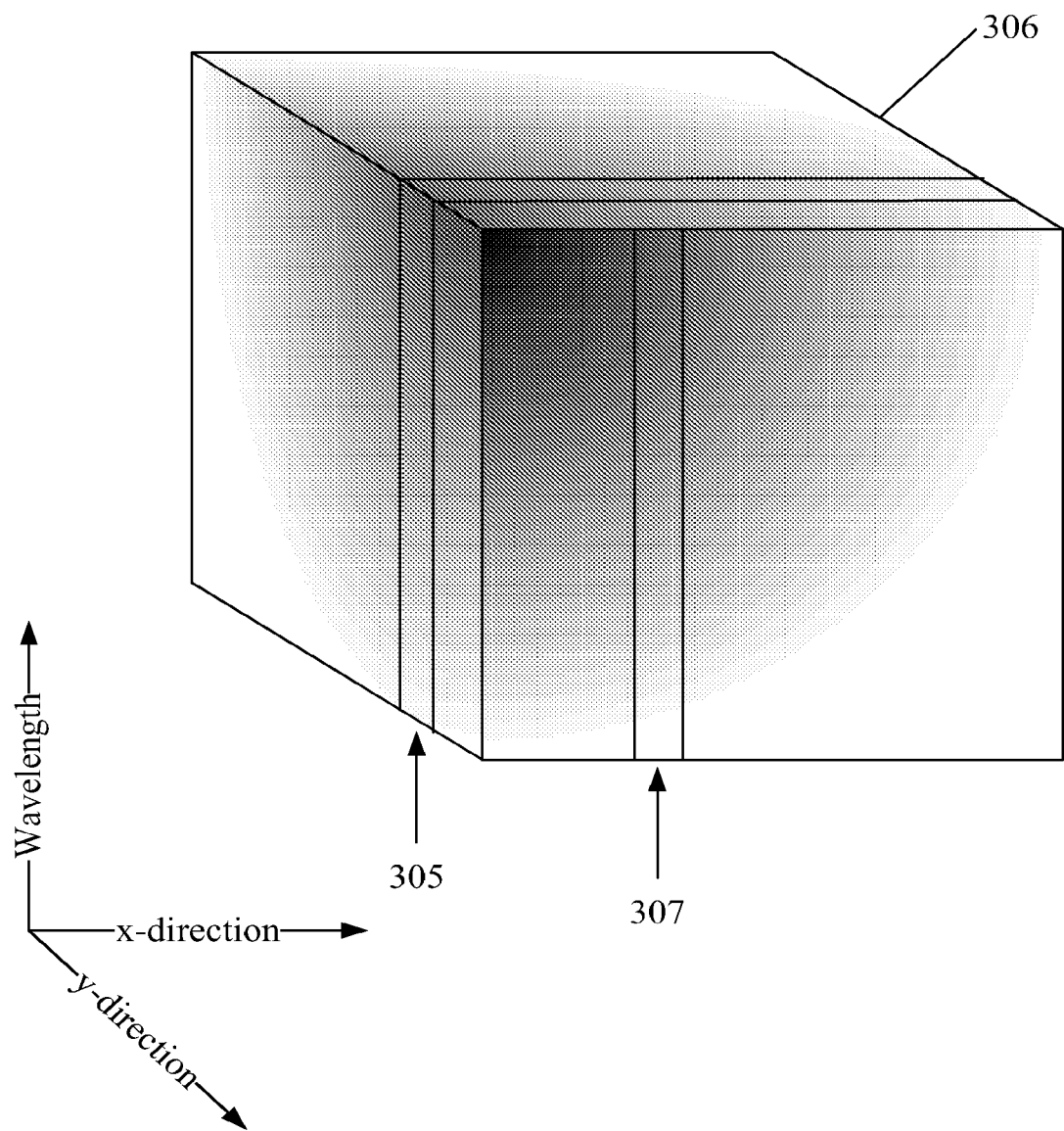
FIG. 3B schematically illustrates a hyperspectral data "cube" including medical information about a subject, according to some embodiments.

FIG. 3B illustrates a "hyperspectral data cube" 306 that the hyperspectral sensor 231 constructs using the planes 305 obtained for each of the rows 202 within area 201. The cube 306 includes a spectrum 307 corresponding to each region 201'. The spectra are stored within a three-dimensional volume, in which two of the axes represent the x- and y-coordinates of the regions 201', and the third axis represents the wavelengths within the corresponding spectra. The intensity at a particular point within the cube 306 represents the intensity of a particular wavelength (λ) at a particular region 201' having coordinates (x, y).

The hyperspectral sensor 231 stores cube 306 in storage device 239, and then passes the cube 306 to processor subsystem 250. In other embodiments, the sensor control subsystem 238 provides hyperspectral data planes to the processor subsystem 250, which then constructs, stores, and processes the hyperspectral data cubes 306. The spectra corresponding to the regions 201' can, of course, be stored in any other suitable format, or at any other suitable location (e.g., stored remotely).

The CCD can include, but is not limited to, a Si CCD, a InGaAs detector, and a HgCdTe detector. Suitable spectral ranges in some embodiments is 0.3 microns to 1 micron, 0.4 micron to 1 micron, 1 micron to 1.7 microns, or 1.3 microns to 2.5 microns. In some embodiments the detector contains between 320 and 1600 spatial pixels. In other embodiments, the CCD has more or less spatial pixels. In some embodiments, the detector has a field of view between 14 degrees and 18.4 degrees. In some embodiments the CCD 237 samples at a rate of between 3 nm and 10 nm. In some embodiments, the CCD samples between 64 and 256 spectral bands. Of course, it is expected over time that improved CCDs or other types of suitable detectors will be devised and any such improved detector can be used.

Within hyperspectral sensor 231, the CCD 237 is arranged at a fixed distance from the dispersive optic 236. The distance between the CCD 237 and the dispersive optic 236, together with the size of the sensor elements that make up the CCD 236, determines (in part) the spectral resolution of the hyperspectral sensor 231. The spectral resolution, which is the width (e.g., full width at half maximum, or FWHM) of the component wavelengths collected by the sensor element, is selected so as to be sufficiently small to capture spectral features of medical conditions of interest. The sensed intensity of component wavelengths depends on many factors, including the light source intensity, the sensor element sensitivity at each particular component wavelength, the reflectance or transmittance of different sensor components such as scan mirror, polarizer, lens, and dispersive optic, and the exposure time of the sensor element to the component wavelength. These factors are selected such that the sensor subsystem 230 is capable of sufficiently determining the intensity of component wavelengths that it can distinguish the spectral features of medical conditions of interest.

The sensor control subsystem 238 can be integrated with the CCD 237, or can be in operable communication with the CCD 237. Collectively, the dispersive optic 236 and CCD 237 form an imaging spectrometer (which can also include other components). Note that the efficiency of a dispersive optic and the sensitivity of a CCD can be wavelength-dependent. Thus, the dispersive optic and CCD can be selected so as to have satisfactory performance at all of the wavelengths of interest to the measurement (e.g., so that together the dispersive optic and CCD allow a sufficient amount of light to be recorded from which a satisfactory spectrum can be obtained).

One example of a suitable hyperspectral sensor 231 is the AISA hyperspectral sensor, which is an advanced imaging spectrometer manufactured by Specim (Finland). The AISA sensor measures electromagnetic energy over the visible and NIR spectral bands, specifically from 430 nm to 910 nm. The AISA sensor includes a "push broom" type of sensor, meaning that it scans a single line at a time, and has a spectral resolution of 2.9 nm and a 20 degree field of vision. An AISA hyperspectral sensor does not include an integrated polarizer 233 as is illustrated in FIG. 2B, but such a polarizer can optionally be included external to the AISA hyperspectral sensor.

Other types of sensors can also be used, that collect light from the regions 201' in other orders. For example, light can be obtained and/or spectrally resolved concurrently from all regions 201'. Or, for example, the light from each individual region 201' can be obtained separately. Or, for example, the light from a subset of the regions can be obtained concurrently, but at a different time from light from other subsets of the regions. Or, for example, a portion of the light from all the regions can be obtained concurrently, but at a different time from other portions of the light from all the regions (for example, the intensity of a particular wavelength from all regions can be measured concurrently, and then the intensity of a different wavelength from all regions can be measured concurrently). In some embodiments, light is obtained from a single row 202 at a time, or a single column 203 at a time.

For example, some embodiments include a liquid crystal tunable filter (LCTF) based hyperspectral sensor. An LCTF-based sensor obtains light from all regions 201' at a time, within a single narrow spectral band at a time. The LCTF-based sensor selects the single band by applying an appropriate voltage to the liquid crystal tunable filter, and recording a map of the reflected intensity of the regions 201' at that band. The LCTF-based sensor then sequentially selects different spectral bands by appropriately adjusting the applied voltage, and recording corresponding maps of the reflected intensity of the regions 201' at those bands. Another suitable type of sensor is a "whisk-broom" sensor that concurrently collects spectra from both columns and rows of regions 201' in a pre-defined pattern. Not all systems use a scan mirror 232 in order to obtain light from the subject. For example, an LCTF-based sensor concurrently obtains light from all regions 201' at a time, so scanning the subject is not necessary.

Suitable modifications for adapting the embodiments described herein for use with other types of hyperspectral sensing schemes will be apparent to those skilled in the art.

ii. Camera

As FIG. 2B illustrates, the sensor subsystem 230 also includes a camera 280. The camera 280 can be, for example, a conventional video or digital camera that produces a conventional visible-light image of the regions 201'.

The camera 280 includes a lens 281, a CCD 282, and an optional polarizer 283. The lens 281 can be a compound lens, as is commonly used in conventional cameras, and may have optical zooming capabilities. The CCD 282 can be configured to take "still" pictures of the regions 201' with a particular frequency, or alternatively can be configured to take a live video image of the regions 201'.

The camera 280, the hyperspectral sensor 231 and/or the THz sensor 290 can be co-bore sighted with each other. By "co-bore sighted" it is meant that the center of each sensor/camera points to a common target. This common focus permits the output of each sensor/camera to be mathematically corrected so that information obtained from each particular region 201' with a particular sensor/camera can be correlated with information obtained from that particular region 201' with all of the other sensors/cameras. In one example, the camera and sensor(s) are co-bore sighted by using each camera/sensor to obtain an image of a grid (e.g., a transparent grid fastened to the subject's skin) The grid marks in each respective image can be used to mathematically correlate the different images with each other (e.g., to find a transform that allows features in one image to be mapped directly onto corresponding features in another image). For example, a hyperspectral image, which may have a relatively low spatial resolution, can be fused with a high spatial resolution visible light image, yielding a hyperspectral image of significantly higher resolution than it would have without fusion.

One example of useful medical information that can be obtained from visible-light images includes geometrical information about medical conditions, such as lesions. Lesions that have irregular shapes, and that are larger, tend to be cancerous, while lesions that have regular shapes (e.g., are round or oval), and that are smaller, tend to be benign. Geometrical information can be included as another criterion for determining whether regions of a subject contain a medical condition.

One example of a suitable camera 280 is a Nikon D300 camera, which is a single-lens reflex (SLR) digital camera with 12.3 megapixel resolution and interchangeable lenses allowing highly detailed images of the subject to be obtained.

iii. THz Sensor

The development of THz sensors for use in medical imaging is an area of much active research. Among other things, THz imaging is useful because THz radiation is not damaging to tissue, and yet is capable of detecting variations in the density and composition of tissue. For example, some frequencies of terahertz radiation can penetrate several millimeters of tissue with low water content (e.g., fatty tissue) and reflect back. Terahertz radiation can also detect differences in water content and density of a tissue. Such information can in turn be correlated with the presence of medical conditions such as lesions.

A wide variety of THz sensors exist that are suitable for use in sensor subsystem 230. In some embodiments, THz sensor 290 includes a THz emitter 291, a THz detector 292, and a laser 293. THz emitter 291 can, for example, be a semiconductor crystal with non-linear optical properties that allow pulses of light from laser 293 (e.g., pulses with wavelengths in the range of 0.3 µm to 1.5 µm) to be converted to pulses with a wavelength in the THz range, e.g., in the range of 25 GHz to 100 THz, or 50 GHz to 84 THz, or 100 GHz to 50 THz. The emitter 291 can be chosen from a wide range of materials, for example, $LiO_3$, $NH_4H_2PO_4$, ADP, $KH_2PO_4$, $KH_2AsO_4$, quartz, $AlPO_4$, ZnO, CdS, GaP, GaAs, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, DAST (4-N-methylstilbazolium), or Si. Other types of emitters can also be used, for example, photoconductive antennas that emit radiation in the desired frequency range in response to irradiation by a beam from laser 293 having a different frequency and upon the application of a bias to the antenna. In some embodiments, laser 293 is a Ti:Sapphire mode-locked laser generating ultrafast laser pulses (e.g., having temporal duration of less than about 300 fs, or less than about 100 fs) at about 800 nm.

The THz radiation emitted by emitter 291 is directed at the subject, for example, using optics specially designed for THz radiation (not illustrated). In some embodiments, the THz radiation is focused to a point at the subject, and the different regions of the subject are scanned using movable optics or by moving the subject. In other embodiments, the THz radiation irradiates multiple points of the subject at a time. The THz radiation can be broadband, e.g., having a broad range of frequencies within the THz band, or can be narrowband, e.g., having only one frequency, or a narrow range of frequencies, within the THz band. The frequency of the THz radiation is determined both by the frequency or frequencies of the laser 293 and the non-linear properties of the emitter 291.

The THz radiation that irradiates the subject (illustrated by the dash-dot-dot lines in FIG. 2B) can be reflected, refracted, absorbed, and/or scattered from the regions of the subject. THz radiation tends to penetrate deeply into tissue, and to partially reflect at interfaces between different types of tissue (which have different indices of refraction). As different portions of the THz radiation interact with different types of tissue, and reflect from different buried features under the surface of the subject's skin, those portions collect both spectral information about the composition of the tissue with which they interact, as well as structural information about the thicknesses of the different layers of tissue and the speed with which the THz radiation passed through the tissue.

The THz detector 292 detects the THz radiation from the subject. As is known in the art, conventional THz detectors can use, for example, electro-optic sampling or photoconductive detection in order to detect THz radiation. In some embodiments, the THz detector 292 includes a conventional CCD and an electro-optical component that converts that converts the THz radiation to visible or NIR radiation that can be detected by the CCD. The THz signal obtained by the THz detector 292 can be resolved in time and/or frequency in order to characterize the composition and structure of the measured regions of the subject.

Some embodiments use a pump-delayed probe configuration in order to obtain spectral and structural information from the subject. Such configurations are known in the art.

One example of a suitable THz imaging system is the T-Ray 400 TD-THz System, available from Picometrix, LLC, Ann Arbor, Mich. Another THz imaging system is the TPI Imaga 1000 available from Teraview, Cambridge, England. For a survey of other currently available systems and methods for THz imaging, see the following references, the entire contents of each of which are incorporated herein by reference: "Imaging with terahertz radiation," Chan et al., Reports on Progress in Physics 70 (2007) 1325-1379; U.S. Patent Publication No. 2006/0153262, entitled "Terahertz Quantum Cascade Layer;" U.S. Pat. No. 6,957,099, entitled "Method and Apparatus for Terahertz Imaging;" and U.S. Pat. No. 6,828,558, entitled "Three Dimensional Imaging."

In some embodiments, the THz sensor generates an intensity map of the reflection of THz radiation from the subject. In other embodiments, the THz sensor generates a THz spectral data cube, similar to the hyperspectral data cube described above, but instead containing a THz spectrum for each region of the subject. The spectra contained in such a cube can be analyzed similarly using techniques analogous to those used to analyze the hyperspectral data cube that are described herein.

C. Contact Probes

Further encompassed is a contact probe for further characterizing a subject that has been characterized by hyperspectral image techniques. For purposes of clarity, the part of the instrument that is associated with hyperspectral image data measurements is called a hyperspectral image module. Accordingly, the part of the instrument comprising one or more contact probes is called a contact probe module. It will be understood that there may be functional or structural overlap between the two types of modules. In general, a contact probe module provides further characterization of the subject in addition to any characterization by the hyperspectral image module. For example, after hyperspectral images of one or more patients are analyzed, a suspect region may be identified and subject to further analysis by a contact probe.

In some embodiments, the contact probe module provides the same type of characterization as the hyperspectral image module but at higher resolution due to a closer proximity between the contact module and the subject than the hyperspectral image module and the subject. In some embodiments, a contact probe module provides additional characterization that has not been performed by the hyperspectral image module. In some embodiments, both the hyperspectral image module and the contact probe module obtain radiometric measurements (e.g., radiance, radiant flux, or radiant intensity; including absorption and diffraction electromagnetic radiation in the visible and invisible range) and/or photometric measurements (e.g., luminance, luminous flux, or luminous intensity). For example, in some embodiments, a contact probe measures signals corresponding to any optical properties of a normal tissue and a tumor tissue, including but not limited to, a Melanin signal, a signal reflecting blood flow and oxy to deoxy hemoglobin ratios, a signal reflecting relative decrease/increase in epidermal and dermal components, a signal reflecting cellular interactions, a signal reflecting protein-based interactions and/or a signal accompanying other biochemical changes.

In some embodiments, the contact probe module may be used to measure morphological changes. For example, the three dimensional contour of a suspect region may be measured by a contact probe and compared with contour features of known types of tissues.

In some embodiments, signals other than radiometric and photometric signals are measured by the contact probe module. For example measurements of a chemical signal, an electrical signal, a magnetic signal, a thermal signal, a mechanical signal, a radiometric signal, a photometric signal, or an optical signal can be obtained. For example, native visible luminescence and/or native fluorescence signals may be used to distinguish a cancer tissue versus a non-cancer tissue. Certain native fluorophores present in virtually all tissues, e.g., tryptophan, NADH, collagen, elastin, and flavins, have been shown to optically change between malignant and non-malignant states of a tissue. The absorption and fluorescence spectral features of these fluorophores are well characterized in the art. These fluorophores are among many others with similar properties from which a selection may be made. Changes in fluorescence patterns arise from a number of these fluorophores and the efficiency to emit and absorb light at a particular wavelength. Some of these molecules are likely involved in protein synthesis, electron transport chain and production of energy in the body, e.g., tryptophan, NADH, and flavins. Collagen, for example, is manufactured in the body to patch wounds and mend broken bones. Elastin protein fibers are manufactured in the body to give muscles strength. By monitoring some of these molecules, such as tryptophan, NAPH, and flavins, one can detect changes in the underlying metabolism, electron transport, and molecular activity in malignant and non-malignant states of tissues.

In some embodiments, the contact probe is configured for measuring a plurality of types of signals associated with the suspect region. For example, a contact probe can obtain measurements of an inherent property of the suspect region, such as conductivity, internal pressure, and/or temperature. A contact probe can measure how the suspect region responds to an external perturbation; for example, how a type of tissue (e.g., skin) responds to external pressure by measuring the elasticity of the suspect region, or how a type of tissue responds to optical signals by obtaining an optical property such as a refractive index. In some embodiments, the suspect region is prepared or processed before additional measurements are taken. For example, the suspect region may be cleaned In some embodiments, the contact probe module is used to measure the suspect region at a single time point by, for example, taking a high resolution hyperspectral image of the suspect region. In some embodiments, the contact probe module is used to capture measurements of the suspect region at a plurality of time points. For example, the contact probe can be a video probe that takes continuous images of the suspect region.

In some embodiments, the contact probe module is a separate device that is independent and separate from the hyperspectral image module. In some embodiments, a contact probe module comprises a physical device that directly or nearly directly contacts the surface of the portion of the object that it measures. Generally, the contact probe module is physically connected to and communicates with the hyperspectral image module. In some embodiments, the connection is achieved by an electronic connection through conventional wired circuit(s) or through fiber optical connection(s). In some embodiments, the connection between the contact probe module and the hyperspectral image module disclosed herein is achieved through wireless connection. Alternatively, the contact probe module can be connected to any part of the system disclosed herein. In some embodiments, a contact probe of a handheld contact probe module can be placed directly or nearly directly on a subject. For example, a contact probe is a fiber-optic probe consisting of a first plurality of illumination fibers and a second plurality of signal collection fibers. In some embodiments, the contact probe is positioned closely to a patient without directly contacting the patient. Measurements collected from the patient are then transmitted to other components of the hyperspectral image system disclosed herein. In some embodiments, the distance between the patient and the contact probe is 1 mm or less, 2 mm or less, 5 mm or less, 10 mm or less, 20 mm or less, 50 mm or less, 100 mm or less, 250 mm or less, or 500 mm or less.

Figure 2C:
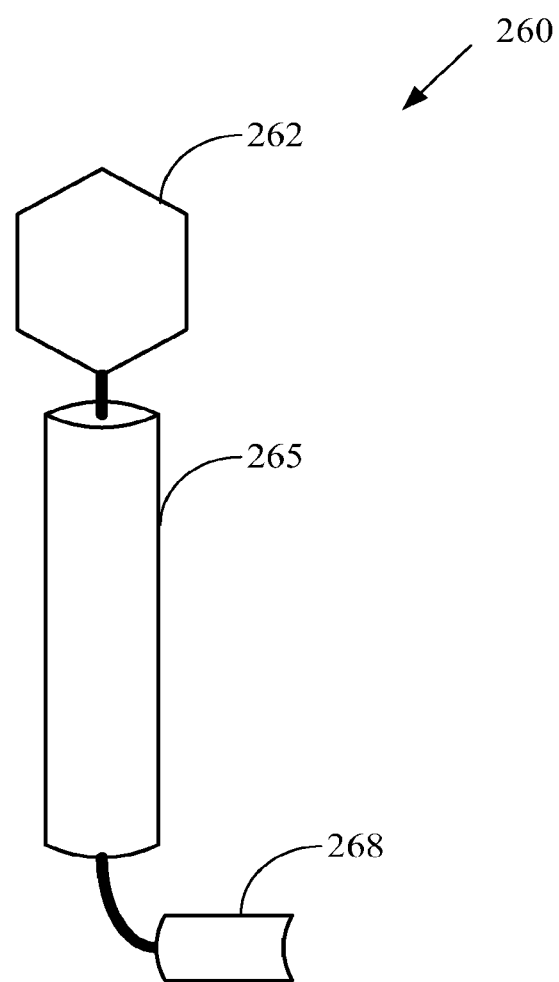
FIG. 2C depicts an exemplary contact probe module, comprising a head unit, a handle unit, and a connector unit, according to some embodiments.

As depicted in FIG. 2C, an exemplary contact probe module 260 comprises a probe head unit 262, a handle unit 265, and a connector unit 268. The probe head unit, handle unit and the connector unit may be linked together by cables and/or electrical/optical/wireless connections. It will be understood that any type of electrical/optical connectors that can enable electrical or optical communications between the contact probe module and the other parts of the hyperspectral image system disclosed herein may be used to establish such connection. In some embodiments, contact probe module 260 comprises only a probe head unit 262 and a handle unit 265. In some embodiments, a wireless connection is used to transfer signal and/or measurement data from the contact probe module to the rest of the hyperspectral image system disclosed herein.

Probe Head Unit 262.

In some embodiments, the probe head unit 262 is used to survey a suspect region of the subject that is being observed. The suspect region can be 1 $cm^2$ or smaller, 2 $cm^2$ or smaller, 5 $cm^2$ or smaller, 8 $cm^2$ or smaller, 10 $cm^2$ or smaller, 15 $cm^2$ or smaller, 20 $cm^2$ or smaller, 30 $cm^2$ or smaller, 50 $cm^2$ or smaller, 75 $cm^2$ or smaller, 100 $cm^2$ or smaller, 150 $cm^2$ or smaller, 200 $cm^2$ or smaller, or 500 $cm^2$ or smaller. For example, a hyperspectral image of a baby may suggest that the baby's left cheek needs to be further examined and accordingly a contact probe may be used to further analyze the baby's left cheek. The contact probes of the instant application may adopt different shapes and sizes when analyzing different samples. The probe head can have a surface area that is 0.25 cm$^2$ or smaller, 0.5 cm$^2$ or smaller, 1 cm$^2$ or smaller, 2 cm$^2$ or smaller, 5 cm$^2$ or smaller, 8 cm$^2$ or smaller, 10 cm$^2$ or smaller, 15 cm$^2$ or smaller, 20 cm$^2$ or smaller, 30 cm$^2$ or smaller, 50 cm$^2$ or smaller, 75 cm$^2$ or smaller, 100 cm$^2$ or smaller, 150 cm$^2$ or smaller, 200 cm$^2$ or smaller, or 500 cm$^2$ or smaller. The probe head can be round, triangular, circular, oval, tubular, or of any suitable shapes and sizes. For example, for the baby's cheek, a small flat-headed contact probe may be used to avoid damaging the delicate skin of the baby. In other embodiments, a contact probe may have a thin protruded shape such as a needle, an elongated probe, etc. Such probes may be used to measure, for example, the inside of the mouth of a patient to provide additional data information to facilitate a diagnosis.

Probes of various capacities may be used as contact probes in conjunction with the hyperspectral image device disclosed herein. A contact probe may be designed for collecting radiometric or photometric measurements. In some embodiments, a contact probe utilizes the same type of sensor device as the hyperspectral image module. The physical proximity between a contact probe and a subject allows the contact probe to collect signals that contain less interference from, for example, ambient light. A contact probe can direct the signals towards the existing sensor system of the hyperspectral image system that eventually renders a hyperspectral image of the suspect region that is at a higher resolution. In some embodiments, the contact probe even shares a sensor system with other part of the hyperspectral image system disclosed herein.

Alternatively, a contact probe that measures a different type of signals from those measured by the hyperspectral image module may be used to provide additional characterization of the suspect regions.

In some embodiments, the sensor device for qualifying the signals measured by the contact probe module is located on the contact probe module. In some embodiments, the sensor device for qualifying the signals measured by the contact probe module is bundled with the existing sensor device in the hyperspectral image component disclosed herein. Contact probe module functions as a conduit means through which signals from the suspect region are passed to the existing sensor device in the hyperspectral image module or an independent shared sensor device. The sensor device may comprise multiple types of sensors for all types of signals obtained by both the contact probe module and the hyperspectral image component.

Types of probes that may be used in the probe head unit include, but are not limited to, an optical probe for visible light, ultra violet light, or infra red light such as a fiber-optic probe; an electrical probe such as a voltmeter probe, an oscilloscope probe, a passive scope probe, a $Z_0$ probe, an active scope probe, a differential probe, a current probe, a near-field probe; a temperature probe, or any type of probe that is capable of receiving, detecting, or recording signals from the suspect region.

In some embodiments, fiber-optic probes may be used. A typical fiber-optic probe comprises a plurality of illumination fibers and a plurality of signal collection fibers. In various embodiments there can be 5 or more illumination fibers, 10 or more each illumination fibers, 15 or more each illumination fibers, 20 or more each illumination fibers, 30 or more each illumination fibers, 50 or more each illumination fibers, or 100 or more each illumination fibers in a fiber-optic probe. Similarly, a fiber-optic probe may have 5 or more signal collection fibers, 10 or more each signal collection fibers, 15 or more each signal collection fibers, 20 or more each signal collection fibers, 30 or more each signal collection fibers, 50 or more each signal collection fibers, or 100 or more each signal collection fibers. It will be understood by one skilled in the art that, there can be any combination of illumination fibers and signal collection fibers. The number of the different types of optic-fibers may be related to the physical design (e.g., shape and size) of the contact probe, or the functional design (e.g., surface or deep tissue detection) of the probe. An exemplary fiber-optic probe design that can be used as a contact probe is described in Tumeh et al., 2007, "Differentiation of Vascular and Non-Vascular Skin Spectral Signatures Using in vivo Hyperspectral Radiometric Imaging," *Cancer Biology & Therapy* 6:3, 447-453, which is hereby incorporated by reference herein in its entirety. In another example, a fiber-optic based probe is employed to direct ultraviolet illumination onto a tissue specimen and to collect the fluorescent response radiation. The response radiation is observed at multiple wavelengths. The intensities of different wavelength can be normalized and used to determine a score using the ratios in a linear discriminant analysis (LDA). See U.S. Pat. No. 7,127,282 to Nordstrom et al. issued on Oct. 24, 2006 (optical methods and systems for rapid screening of the cervix), which is hereby incorporated by reference herein in its entirety.

Additional exemplary types of contact probes that can be used include, but are not limited to, those described, for example, in U.S. Pat. No. 5,413,108 (Method and Apparatus for Mapping a Tissue Sample for and Distinguishing Different Regions Thereof Based on Luminescence Measurements of Cancer-Indicative Native Fluorophore); U.S. Pat. No. 5,036,853 (Physiological Probe); U.S. Pat. No. 5,792,053 (Hybrid Probe for Tissue Type Recognition); U.S. Pat. No. 5,830,146 (Sheathed Probes for Tissue type Recognition); U.S. Pat. No. 5,842,995 (Spectroscopic Probe for In vivo Measurement of Raman Signals); U.S. Pat. No. 5,941,834 (Sheath for a Side View Probe); U.S. Pat. No. 5,953,306 (Micro Needle Probe Apparatus having Probes Cantilevered Over Respective Electronic Circuits, Moving Medium Memory Device Including Same and Method of Making Same); U.S. Pat. No. 6,477,132 (Probe and Information Recording/Reproduction Apparatus Using the Same); U.S. Pat. No. 7,185,440 (Sensing Contact Probe); U.S. Pat. No. 7,310,547 (Fluorescent Fiberoptic Probe for Tissue Health Discrimination) each of which is hereby incorporated by reference herein in its entirety, as well as United States Patent Publication Nos. 20030215791 A120050254709 A1, each of which is hereby incorporated by reference herein in its entirety.

It will be understood by one of ordinary skill in the art that the probe head unit 262 may be designed to incorporate interchangeability such that multiple types of probe head units may be interchangeably attached to the handle unit 265 such that more than one type of signals may be obtained and measured for further analyses.

In addition to the native fluorophores that are inherent to the human body, synthetic and exogenous fluorophores may be temporarily administered to a subject in order to facilitate data collection. Such administration can be, for example, through oral means, injection or simply by rubbing the reagent onto the suspect region.

More on additional devices that may be used for data collection by contact probes. For example, additional light source, additional reagents, additional equipment for temporary or permanently storing measurements collected from the suspect region.

Handle Unit 265.

Preferably, a contact probe module is a handheld device. In some embodiments, the handle unit 265 has an elongated shape to fit the hand of a user operating the contact probe module. The handle unit 265 may be cylindrical or tubular. In some embodiments, handle unit 265 has a hollow space that along one of its dimensions (e.g., the longest dimension) such that cables or wires for electrical and/or optical connection between the probe head unit 262 and the hand unit 265 may be accommodated in the hollow space. In some embodiments, adaptor motif (such as a screw-type adaptor or a magnet-type adaptor) is found at one or both ends of the hollow space for connecting the handle unit 265 to the probe head unit 262 and to the connector unit 268. In some embodiments, the adaptor motif for the probe head unit 262 is designed to receive multiple types of probe head units. Any type or number of contact probes discussed hereinabove may be attached to the probe head.

In other embodiments, the handle unit 265 comprises a groove-like structure for accommodating the cables or wires for electrical and/or optical connection between the probe head unit 262 and the hand unit 265. The groove-like structure may be embedded inside the handle unit 265 or on the surface of in the handle unit 265.

In some embodiments, the handle unit 265 is ergonomically designed such that it conveniently and comfortably fits the hand of an operator of the contact probe module. In some embodiments, the handle unit 265 is made of rigid materials such as plastic, wood, metal, stainless steel, aluminum or an aluminum alloy. In other embodiments, the handle unit 265 is made of flexible materials such as a rubberlike material, a rubber derivative, silicone rubber, or an elastomer, natural rubber, vulcanized rubber, a butadiene-styrene polymer such as GR-S, neoprene, nitrile rubbers, butyl, polysulfide rubber, ethylene-propylene rubber, polyurethane rubber, silicone rubber, gutta-percha, and/or balata. In still other embodiments, the handle unit 265 is made of rigid and flexible material, for example, a rigid tubular structure coated with a flexible rubber-like material for comfort and easy gripping.

Connector Unit 268.

In preferred embodiments, connector unit 268 links the contact probe module with the rest of the disclosed hyperspectral image apparatus. In some embodiments, the contact probe is an integrated part of the sensor device described herein above. For example, a handheld contact probe module is permanently attached to some embodiments of the disclosed the hyperspectral image device. Alternatively, a handheld contact probe can operate as a separate and removable module that may be transferred from one image device to another image device. Such transferable portability can be enabled by standard connection through a connector unit 268. For example, connector unit 268 can be a standard electrical/optical connector plug which can be plugged into a receiving outlet on any part of the hyperspectral medical imaging system 200.

In addition to the units described above, there may be additional units in the contact probe module including but not limited to an additional light source, an additional display device, a data window, or an optional memory device for storing data.

Data transfer between the contact probe module and the other part of the system occurs through wired connection or wirelessly. It is possible that the data collected by the contact probe unit may be stored temporarily on the contact probe unit (e.g. in a USB memory key, plug in device, etc.) before being transferred to the hyperspectral data processing module for further processing.

D. Processor Subsystem

Referring to FIG. 2B, the processor subsystem 250 includes a storage device 252, a spectral calibrator 253, a spectral analyzer 254, an image constructor 256, and a power supply 258. The processor subsystem is in operable communication with the illumination subsystem 210, the sensor subsystem 230, and the display subsystem 270.

The processor subsystem 210 instructs illumination subsystem 210 to irradiate the regions 201' of the subject. Optionally, the processor subsystem 210 controls the polarization selected by polarizer 213, e.g., by instructing illumination subsystem 210 to rotate polarizer 213 to a particular angle corresponding to a selected polarization.

The processor subsystem 250 instructs hyperspectral sensor 231, in the sensor subsystem 230, to obtain spectra of the regions 201'. The processor subsystem 250 can provide the hyperspectral sensor 231 with instructions of a variety of parameter settings in order to obtain spectra appropriately for the desired application. These parameters include exposure settings, frame rates, and integration rates for the collection of spectral information by hyperspectral sensor 231. Optionally, the processor subsystem 250 also controls the polarization selected by polarizer 233, e.g., by instructing hyperspectral sensor 231 to rotate polarizer 233 to a particular angle corresponding to a selected polarization.

The processor subsystem 250 then obtains from hyperspectral sensor 231 the spectra, which may be arranged in a hyperspectral data plane or cube. The processor subsystem 250 also obtains from sensor subsystem 230 information from any other sensors, e.g., camera 280 and THz sensor 290. The processor subsystem 250 stores the spectra and the information from the other sensors in storage device 252, which can be volatile (e.g., RAM) or non-volatile (e.g., a hard disk drive).

The spectral calibrator 253 then calibrates the spectra stored in the hyperspectral data cube, and optionally the images obtained from other sensors in sensor subsystem 230, using a spectral calibration standard and techniques known in the art. In some instances the spectral calibration standard comprises a spatially uniform coating that diffusely reflects a known percentage of light (e.g., any percentage in the range between 1% or less of light up through and including 99% or more of light). In some embodiments, the output of a sensor can be calibrated by obtaining an image of the spectral calibration standard using that sensor. Because the percentage of light reflected from the standard is known for each wavelength, the responsiveness of the sensor at each wavelength can be accurately determined (e.g., the sensor can be calibrated) by comparing the measured reflection of light from the standard to the expected reflection of light from the standard. This allows the illumination-independent and wavelength-dependent reflectance of the subject to be measured far more accurately than if a spectral calibration standard had not been used. In other embodiments, when the light intensity of the light source and the sensitivity of the hyperspectral sensor are known, the reflectance of the subject can be directly calculated without help of a spectral calibration standard.

As described in greater detail below, the spectral analyzer 254 then analyzes selected portions of the spectra, and then the image constructor 256 constructs a hyperspectral image based on the analyzed spectra. Optionally, the image constructor 256 fuses the hyperspectral image with other information about the subject, e.g., images obtained using camera 280 and/or THz sensor 290.

The power supply 258 provides power to the processor subsystem 250, and optionally also provides power to one or more other components of hyperspectral imaging system 200. The other components of the hyperspectral imaging system 200 can alternately have their own power supplies. In some embodiments, for example where imaging system 200 is intended to be portable (e.g., can be carried by hand and/or is usable outside of a building), the power supply 258 and/or other power supplies in the system 200 can be batteries. In other embodiments, for example where imaging system 200 is fixed in place, or where imaging system is intended to be used inside of a building, the power supply 258 and/or other power supplies in the system 200 can obtain their power from a conventional AC electrical outlet.

The spectral analyzer 254 and the image constructor 256 will now be described in greater detail. Then, an exemplary computer architecture for processor subsystem 250 will be described.

i. Spectral Analyzer

In some embodiments, the spectral analyzer 254 analyzes the spectra obtained from storage 252 by comparing the spectral characteristics of a pre-determined medical condition to the subject's spectra within defined spectral ranges. Performing such a comparison only within defined spectral ranges can both improve the accuracy of the characterization and reduce the computational power needed to perform such a characterization.

The spectral characteristics of a medical condition, such as particular lesion type, can be determined, for example, by first identifying an actual skin lesion of that type on another subject, for example using conventional visual examination and biopsy, and then obtaining the wavelength-dependent reflectance $R_{SL}(\lambda)$ of a representative region of that skin lesion. The skin lesion's reflectance $R_{SL}(\lambda)$ can then be spectrally compared to the wavelength-dependent reflectance of that subject's normal skin in the same area of the lesion, $R_{NS}(\lambda)$, by normalizing the reflectance of the skin lesion against the reflectance of normal skin as follows:

$$R_{SL,N}(\lambda)=R_{SL}(\lambda)/R_{NS}(\lambda),$$

where $R_{SL,N}(\lambda)$ is the normalized reflectance of the skin lesion. In other embodiments, $R_{SL,N}(\lambda)$ is instead determined by taking the difference between $R_{SL}(\lambda)$ and $R_{NS}(\lambda)$, or by calculating $R_{SL,N}(\lambda)=[R_{SL}(\lambda)-R_{NS}(\lambda)]/[R_{SL}(\lambda)+R_{NS}(\lambda)]$. Other types of normalization are possible. Note that if there are multiple representative regions of one skin lesion, there will be as many normalized reflectances of the skin lesion. These normalized reflectances can be averaged together, thus accounting for the natural spectral variation among different regions of the lesion. Note also that because of the natural variation in characteristics of normal skin among individuals, as well the potential variation in characteristics of a particular type of lesion among individuals, it can be useful to base the model of the normalized skin lesion reflectance $R_{SL,N}(\lambda)$ on the average of the reflectances $R_{SL}(\lambda)$ of many different skin lesions of the same type, as well as on the average of the reflectances $R_{NS}(\lambda)$ of many different types of normal skin (e.g., by obtaining $R_{SL,N}(\lambda)$ for many different subjects having that lesion type, and averaging the results across the different subjects).

In one embodiment, in order to determine whether the subject has the type of skin lesion characterized by $R_{SL,N}(\lambda)$, the spectral analyzer 254 obtains the skin reflectance of each region 201', $R_{region}(\lambda)$, from hyperspectral sensor 231 (e.g., in the form of a hyperspectral data plane or cube). The spectral analyzer 254 then normalizes the reflectance $R_{region}(\lambda)$ from that region against the wavelength-dependent reflectance of the subject's normal skin in the same area, $R_{NS, Subject}(\lambda)$, as follows:

$$R_{region,N}(\lambda)=R_{region}(\lambda)/R_{NS,Subject}(\lambda),$$

where $R_{region,N}(\lambda)$ is the normalized reflectance of the region. Other types of normalization are possible.

In some embodiments, the spectral analyzer 254 analyzes the subjects' spectra by comparing $R_{region,N}(\lambda)$ to $R_{SL,N}(\lambda)$. In one simple example, the comparison is done by taking the ratio $R_{region,N}(\lambda)/R_{SL,N}(\lambda)$, or the difference $R_{SL,N}(\lambda)-R_{region,N}(\lambda)$. The magnitude of the ratio or difference indicates whether any region has spectral characteristics that match that of the lesion. However, while ratios and differences are simple calculations, the result of such a calculation is complex and requires further analysis before a diagnosis can be made. Specifically, the ratio or subtraction of two spectra, each of which has many peaks, generates a calculated spectrum that also has many peaks. Some peaks in the calculated spectrum may be particularly strong (e.g., if the subject has the medical condition characterized by $R_{SL,N}(\lambda)$), but other peaks may also be present (e.g., due to noise, or due to some particular characteristic of the subject). A physician in the examination room would typically find significantly more utility in a simple "yes/no" answer as to whether the subject has a medical condition, than he would in a complex spectrum. One method of obtaining a "yes/no" answer is to calculate whether a peak in the calculated spectrum has a magnitude that is above or below a predetermined threshold and is present at a wavelength that would be expected for that medical condition.

Another way to obtain a "yes/no" answer is to treat $R_{region,N}(\lambda)$ and $R_{SL,N}(\lambda)$ as vectors, and to determine the "angle" between the vectors. The angle represents the degree of overlap between the vectors, and thus represents how likely it is that the subject has the medical condition. If the angle is smaller than a threshold value, the subject is deemed have the medical condition; if the angle does not exceed a threshold value, the subject is deemed not to have the medical condition. Alternately, based on the value of the angle between the vectors, a probability that the subject has the medical condition can be determined.

While hyperspectral imaging can obtain spectra across broad ranges of wavelengths (e.g., from 400 nm to 2000 nm), and such breadth allows a vast amount of medical information to be collected about the subject, most of the spectrum does not contain information relevant to a single, particular medical condition. For example, skin lesion type "A" may only generate a single spectral peak centered at 1000 nm with 50 nm full width at half maximum (FWHM). Of course, most medical conditions generate considerably more complex spectral features. The rest of the peaks in the spectrum do not contain information about lesion type "A." Even though they may contain information about many other types of medical conditions, these peaks are extraneous to the characterization of lesion type "A" and can, in some circumstances, make it more difficult to determine whether the subject has lesion type "A."

In some embodiments, the spectral analyzer 254 reduces or eliminates this extraneous information by comparing $R_{region,N}(\lambda)$ to $R_{SL,N}(\lambda)$ only within specified spectral regions that have been identified as being relevant to that particular type of skin lesion. Using the example above, where lesion type "A" only generates a single peak at 1000 nm with 50 nm FWHM, the spectral analyzer 254 compares $R_{region,N}(\lambda)$ to $R_{SL,N}(\lambda)$ only at a narrow spectral region centered at 1000 nm (e.g., a 50 nm FWHM band centered at 1000 nm). For medical conditions that generate more complex spectral features, the spectral analyzer 254 can compare $R_{region,N}(\lambda)$ to $R_{SL,N}(\lambda)$ within other spectral regions of appropriate width. Such bands can be determined by statistically identifying which spectral features correlate particularly strongly with the medical condition as compared with other spectral features that also correlate with the medical condition. For example, when calculating the angle between vectors $R_{region,N}(\lambda)$ and $R_{SL,N}(\lambda)$, the extraneous information can reduce the angle between the vectors, thus suggesting a higher correlation between $R_{region,N}(\lambda)$ and $R_{SL,N}(\lambda)$ than there actually is for lesion type "A."

In one example, a particular medical condition has identifiable spectral characteristics within a narrow, contiguous wavelength range $\lambda_1$-$\lambda_2$ (e.g., 850-900 nm). The bounds of this range are stored in storage 252, along with the spectral characteristics of the condition within that range. To compare the condition's spectral characteristics to those of the subject, the spectral analyzer 254 can first select portions of the subject's hyperspectral data cube that fall within the desired wavelength range $\lambda_1$-$\lambda_2$. Multiple spectral regions can also be selected, and need not be contiguous with one another. The unused spectral portions need not be discarded, but can be saved in storage 252 for later use, as described in greater detail below.

Figure 4A:
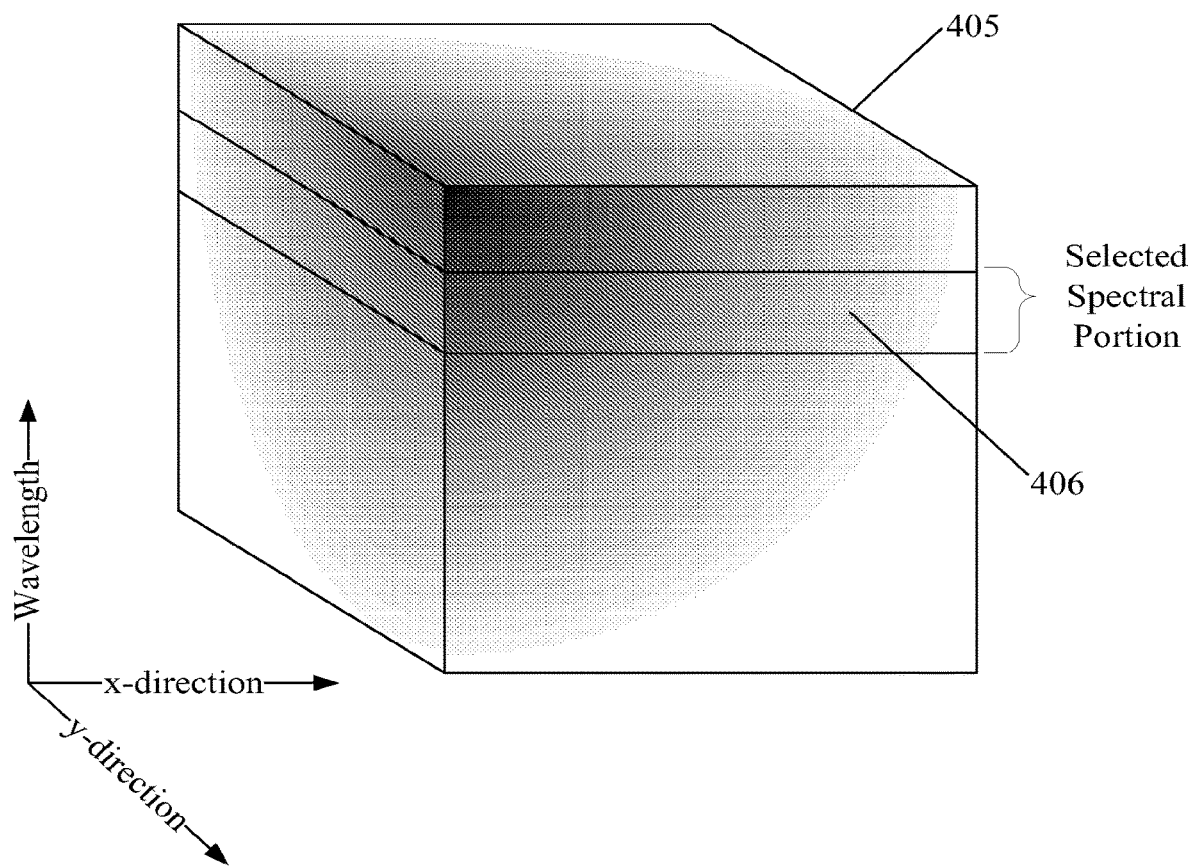
FIG. 4A schematically illustrates selection of a portion of a hyperspectral data "cube" including medical information about a subject, according to some embodiments.
Figure 4B:
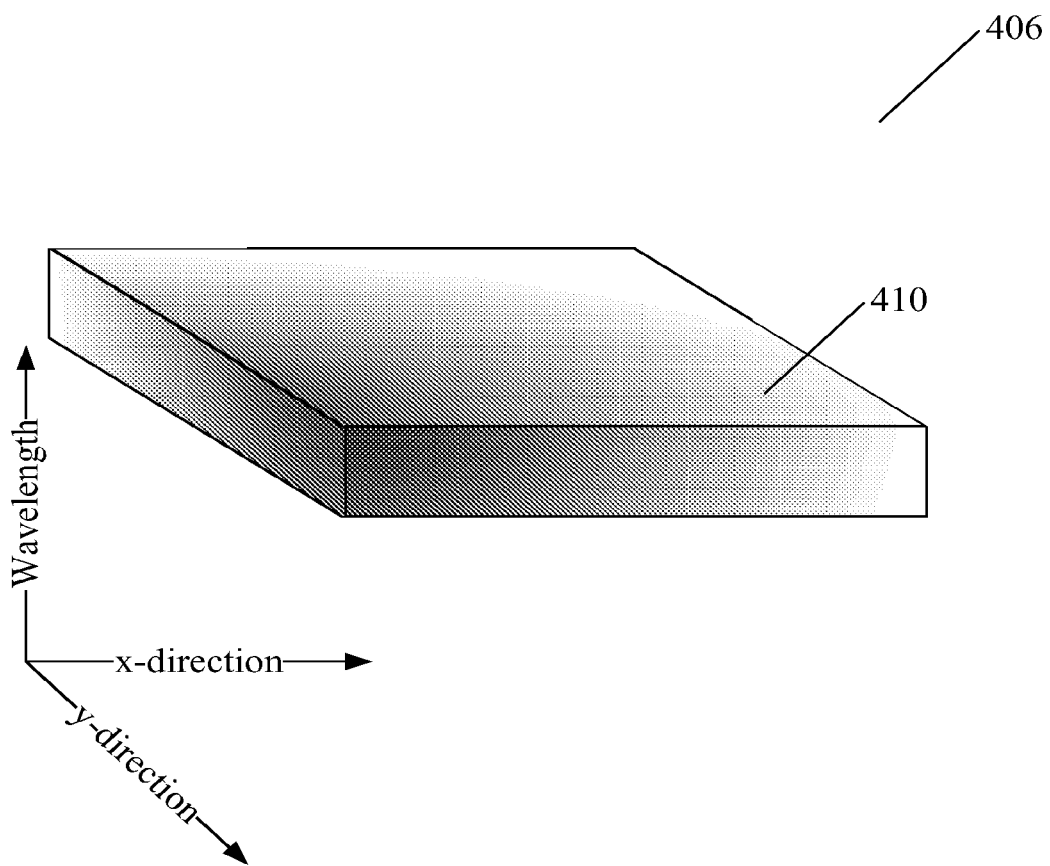
FIG. 4B schematically illustrates a selected portion of a hyperspectral data "cube" including medical information about a subject, according to some embodiments.

Following the same example, FIG. 4A illustrates the spectral analyzer's selection of a volume 406 from the subject's hyperspectral data cube 405 within the wavelength range $\lambda_1$-$\lambda_2$ characteristic of the medical condition. The boundaries of volume 406 are defined by the x- and y-dimensions of area 201 and by wavelength range $\lambda_1$-$\lambda_2$. FIG. 4B illustrates a selected volume 406. The intensity distribution at the top face 410 of the volume corresponds to the spectral intensity at wavelength $\lambda_1$ of each region 201' within the area 201, while the intensity distribution at the bottom face (not shown) of the volume corresponds to the spectral intensity at wavelength $\lambda_2$. Thus it can be seen that regions in the lower left corner of the area 201 strongly interacted with light at wavelength $\lambda_1$, while regions in the upper right corner of the area 201 weakly interacted with light at wavelength $\lambda_1$. This indicates that the medical condition is present in the regions in the lower left corner of area 201, but not in the regions in the upper right corner of area 201. While the volume 406 is illustrated as contiguous, the selected volume of the hyperspectral cube could instead be a combination of multiple sub-volumes that are not adjacent to each other. Within the selected spectral region(s), $R_{region,N}(\lambda)$ can be calculated and then compared to $R_{SL,N}(\lambda)$ using the methods described above, or any other suitable method.

There are several other different ways to perform such comparisons only within selected spectral regions. For example, for an angle analysis, the vectors $R_{Region}(\lambda)$ and $R_{SL,N}(\lambda)$ can be reduced in size to eliminate values corresponding to wavelengths outside of the selected spectral regions, and the angle analysis performed as above. Or, for example, values in the vectors $R_{Region}(\lambda)$ and $R_{SL,N}(\lambda)$ that fall outside of the selected spectral regions can be set to zero, and the angle analysis performed as above. For other types of comparisons, for example, ratios or differences, the ratio or difference values that fall outside of the selected spectral regions can simply be ignored.

In other embodiments, the vectors $R_{SL,N}(\lambda)$ or multiple lesions of the same medical condition are used to train a classifier using certain pattern recognition methods as explained in detail later, and the vector $R_{Region}(\lambda)$ of an un-identified lesion can be input into the classifier to see the medical condition is present.

The selection scheme illustrated in FIGS. 4A and 4B is a simple example based on the characteristics of a single medical condition stored in a spectral signature library. More complicated schemes can also be used. For example, multiple spectral regions can be selected in parallel or in sequence based on the spectral characteristics of multiple pre-determined conditions. For example, as noted above, a physician may not be able to determine through visual inspection whether a lesion is benign or cancerous. Thus it can be useful for the spectral analyzer 254 to select spectral regions based on the spectral characteristics of a wide variety of potential conditions.

The skin lesion example is intended to be merely illustrative. Similar procedures can be used to obtain a wavelength-dependent reflectance $R(\lambda)$ for a wide variety of medical conditions and/or physiological features and/or chemicals. For example, the $R(\lambda)$ of a subject having that condition/feature/chemical can be obtained and then normalized against the $R(\lambda)$ of a subject lacking that condition/feature/chemical. Spectral regions particularly relevant to that condition/feature/chemical can be identified and used during the comparison of the condition's reflectance $R(\lambda)$ to the subject's reflectance, e.g., as described above.

Regardless of the particular form in which the spectral information about the medical condition is stored, in some embodiments the processor subsystem 250 can access a library of spectral information about multiple medical conditions, that can be used to determine whether the subject has one or more of those conditions. The library can also include information about each condition, for example, other indicia of the condition, possible treatments of the condition, potential complications, etc.

The library can also store biological information about each condition that may be useful in determining whether a subject has the condition. For example, skin pigmentation naturally varies from subject to subject, which causes variations in the wavelength-dependent reflectance between those individuals. These variations can complicate the determination of whether a particular individual has a condition. The library can include information that enhances the ability of processor subsystem 250 to identify whether subjects having a particular skin pigmentation have a condition. Portions of the library can be stored locally (e.g., in storage 252) and/or remotely (e.g., on or accessible by the Internet).

In still other embodiments, portions of spectra are selected based on information in other images obtained of the regions 201', e.g., based on information in a visible-light image, a LIDAR image, and/or a THz image of the regions 201'.

The spectral analyzer 254 can operate on an automated, manual, or semi-manual basis. For example, in an automatic mode, the spectral analyzer 254 can fully search the spectral library for conditions having spectral characteristics that potentially match those of one or more of the regions 201'. In a semi-manual mode, a sub-class of conditions can be identified, or even a single condition, of interest, and the spectral analyzer can analyze the subject's spectra based on the spectral characteristics of that condition or conditions. Or, in a manual mode, the spectral analyzer can operate wholly under the control of a human. In some embodiments, "automated" means without human intervention, and "manual" means with human intervention.

ii. Image Constructor

After the spectral analyzer 254 analyzes the spectra, the image constructor 256 constructs an image based on the analyzed spectra. Specifically, the image constructor 256 creates a representation (e.g., a 2D or 3D representation) of information within the spectra. In one example, the image constructor 256 constructs a two-dimensional intensity map in which the spatially-varying intensity of one or more particular wavelengths (or wavelength ranges) within the spectra is represented by a corresponding spatially varying intensity of a visible marker.

Figure 5:
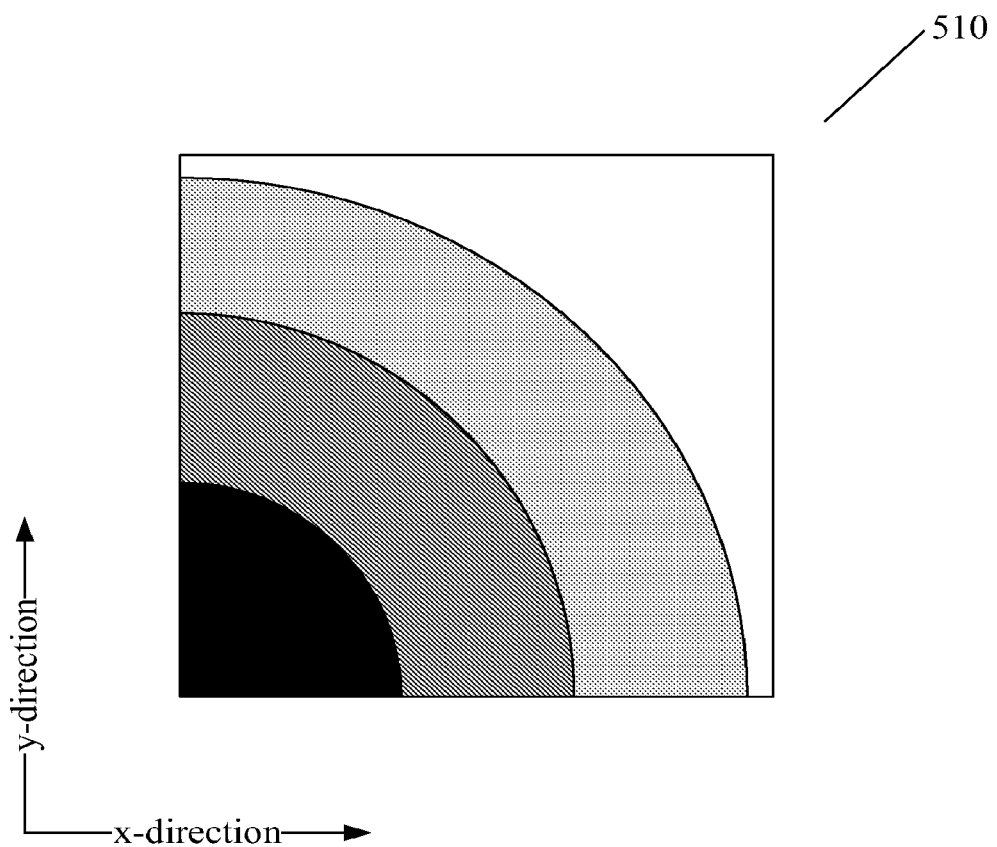
FIG. 5 schematically illustrates an image based on a portion of a spectrum, according to some embodiments.

FIG. 5 illustrates an image 510 that is based on the spatial variations in intensity at wavelength $\lambda_1$ that are illustrated in FIG. 4B. The image 510 includes regions 511, 512, and 513 of increasing intensity, respectively, which represent the magnitude of interaction of different regions 201' with light at wavelength $\lambda_4$. While FIG. 5 is monochromatic, false colors can also be assigned to represent different intensities or other information. For example, in embodiments in which multiple spectral portions corresponding to multiple potential conditions are selected, spectral portions corresponding to one condition can be assigned one color, and spectral portions corresponding to another condition can be assigned a different color, thus allowing areas affected by the different conditions to be distinguished.

Figure 7A:
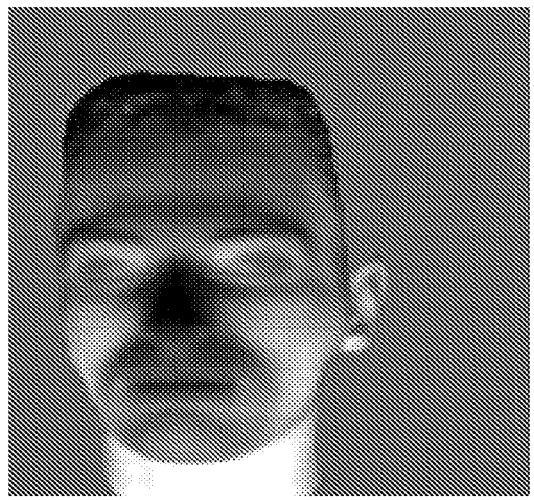
FIGS. 7A-7C illustrate exemplary images from different spectral bands that contain different medical information about a subject, according to some embodiments.
Figure 7B:
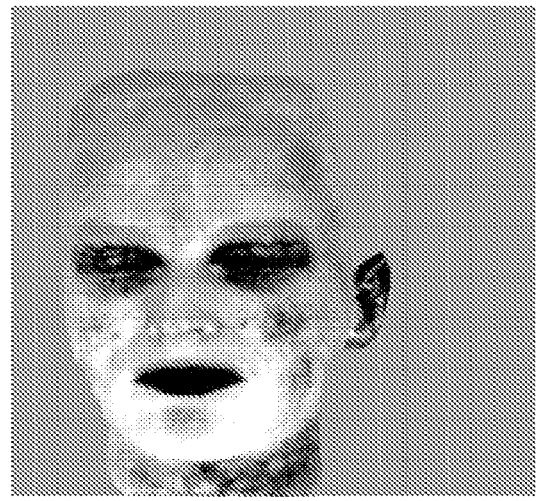
Figure 7C:
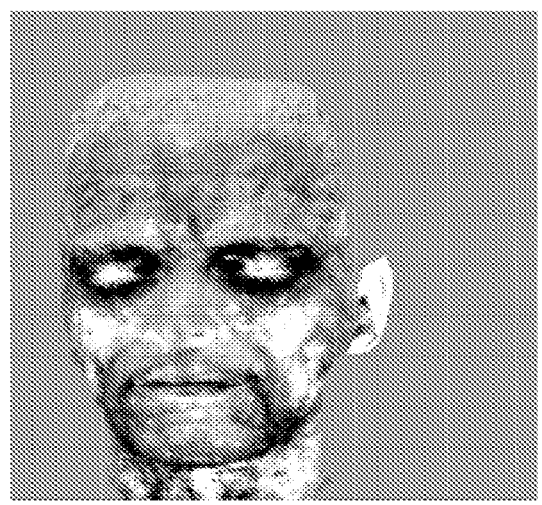

In some embodiments, the image constructor 256 fuses the hyperspectral image with information obtained from one or more other sensors in sensor subsystem 230. For example, as illustrated in FIGS. 7A-7C, different regions of the electromagnetic spectrum contain significantly different information about a subject. FIG. 7A is an image of a subject obtained in the visible portion of the spectrum (e.g., is a conventional video or photographic image of the subject). FIG. 7B is an image of the same subject, but obtained in the thermal portion of the spectrum (e.g., SWIR to MIR). FIG. 7C is another image of the same subject but obtained in still another portion of the spectrum. The different images were obtained with appropriate conventional sensors that are known in the art, and highlight different aspects of the medical condition of the subject. By obtaining relevant information in the appropriate electromagnetic band(s), and combining that information with an image representing spectral information about the subject such as that described herein, images can be generated that provide significantly more detailed information than an image that represents only a single type of information.

Information from different sensors can be fused with the hyperspectral image in many different ways. For example, the hyperspectral image can be scaled to a grey scale or color, and data from another sensor is topographically scaled to form a topographical or contour map. In such embodiments, the topographical or contour map can be colored based on the grey scale or color scaled hyperspectral image. Of course, the reverse is also true, where the hyperspectral image is converted to a topographical or contour map and the data from another sensor is normalized to a color scale or a grey scale which is then used to color the topographical or contour map. Usefully, such a combined map can emphasize skin abnormalities that may not be apparent from any one sensor. For example, if one sensor flags a particular region of the screen with a "red" result, where red represents one end of the dynamic range of the sensor, and another sensor assigns a dense peak to this same region, where the peak represents the limits of the dynamic range of this independent sensor, the combined image from the two sensors will show a peak that is colored red. This can aid in pinpointing a region of interest.

Information from one or more sensors can be fused with the hyperspectral image. In some embodiments, information from two or more, three or more, four or more, five or more sensors are fused with the hyperspectral image into a single image.

In some embodiments, images obtained using different sensors are taken concurrently, so that the register of such images with respect to the skin of the subject and to each other is known. In some embodiments, such images are taken sequentially but near in time with the assurance that the subject has not moved during the sequential measurements so that the images can be readily combined. In some embodiments, a skin registry technique is used that allows for the images from different sensors to be taken at different times and then merged together.

Concurrently using different types of sensors provides a powerful way of obtaining rich information about the subject. Specific types of sensors and/or data fusion methods can be used to analyze different types of targets. For example, in remote sensing analysis, a sensor specific for submerged aquatic vegetation (SAV) has been employed. Furthermore, normalized difference vegetation index (NDVI) is also developed for better representation. Similarly, in medical imaging, specific sensors may be used to detect changes in specific types of tissues, substances, or organs. Indices similar to NDVI can also be developed to normalize certain types of tissues, substances, or organs, either to enhance their presence or to reduce unnecessary background noise.

The information obtained by multi-sensor analysis can be integrated using data fusion methods in order to enhance image quality and/or to add additional information that is missing in the individual images. In the following section on data fusion methods, the term "sensor" means any sensor in sensor subsystem 230, including hyperspectral sensor 231, THz sensor 290, and camera 280, or any other type of sensor that is used in sensor subsystem 230.

In some embodiments, information from different sensors are displayed in complementary (orthogonal) ways, e.g., in a colorful topographical map. In some embodiments, the information from different sensors is combined using statistical techniques such as principal component analysis. In some embodiments, the information from different sensors is combined in an additive manner, e.g., by simply adding together the corresponding pixel values of images generated by two different sensors. Any such pixel by pixel based combination of the output of different sensors can be used.

Image fusion methods can be broadly classified into two categories: 1) visual display transforms; and 2) statistical or numerical transforms based on channel statistics. Visual display transforms involve modifying the color composition of an image, e.g., modifying the intensities of the bands forming the image, such as red-green-blue (RGB) or other information about the image, such as intensity-hue-saturation (IHS). Statistical or numerical transforms based on channel statistics include, for example, principal component analysis (PCA). Some non-limiting examples of suitable image fusion methods are described below.

Band Overlay.

band overlay (also known as band substitution) is a simple image fusion technique that does not change or enhance the radiometric qualities of the data. Band overlay can be used, for example, when the output from two (or more) sensors is highly correlated, e.g., when the sensors are co-bore sighted and the output from each is obtained at approximately the same time. One example of band overlay is panchromatic sharpening, which involves the substitution of a panchromatic band from one sensor for the multi-spectral band from another sensor, in the same region. The generation of color composite images is limited to the display of only three bands corresponding to the color guns of the display device (red-green-blue). As the panchromatic band has a spectral range covering both the green and red channels (PAN 0.50-0.75 mm; green 0.52-0.59 mm; red 0.62-0.68 mm), the panchromatic band can be used as a substitute for either of those bands.

High-Pass Filtering Method (HPF).

The HPF fusion method is a specific application of arithmetic techniques used to fuse images, e.g., using arithmetic operations such as addition, subtraction, multiplication and division. HPF applies a spatial enhancement filter to an image from a first sensor, before merging that image with an image from another sensor on a pixel-by-pixel basis. The HPF fusion can combine both spatial and spectral information using the band-addition approach. It has been found that when compared to the IHS and PCA (more below), the HPF method exhibits less distortion in the spectral characteristics of the data, making distortions difficult to detect. This conclusion is based on statistical, visual and graphical analysis of the spectral characteristics of the data.

Intensity-Hue-Saturation (IHS).

IHS transformation is a widely used method for merging complementary, multi-sensor data sets. The IHS transform provides an effective alternative to describing colors by the red-green-blue display coordinate system. The possible range of digital numbers (DNs) for each color component is 0 to 255 for 8-bit data. Each pixel is represented by a three-dimensional coordinate position within the color cube. Pixels having equal components of red, green and blue lie on the grey line, a line from the cube to the opposite corner. The IHS transform is defined by three separate and orthogonal attributes, namely intensity, hue, and saturation. Intensity represents the total energy or brightness in an image and defines the vertical axis of the cylinder. Hue is the dominant or average wavelength of the color inputs and defines the circumferential angle of the cylinder. It ranges from blue (0/360°) through green, yellow, red, purple, and then back to blue (360/0°). Saturation is the purity of a color or the amount of white light in the image and defines the radius of the cylinder.

The IHS method tends to distort spectral characteristics, and should be used with caution if detailed radiometric analysis is to be performed. Although IRS 1C LISS III acquires data in four bands, only three bands are used for the study, neglecting the fourth due to poor spatial resolution. IHS transform can be more successful in panchromatic sharpening with true color composites than when the color composites include near or mid-infrared bands.

Principal Component Analysis (PCA).

PCA is a commonly used tool for image enhancement and the data compression. The original inter-correlated data are mathematically transformed into new, uncorrelated images called components or axes. The procedure involves a linear transformation so that the original brightness values are re-projected onto a new set of orthogonal axes. PCA is useful for merging images because of it includes reducing the dimensionality of the original data from n to 2 or 3 transformed principal component images, which contains the majority of the information from the original sensors. For example, PCA can be used to merge several bands of multispectral data with one high spatial resolution band.

Image fusion can be done in two ways using the PCA. The first method is similar to IHS transformation. The second method involves a forward transformation that is performed on all image channels from the different sensors combined to form one single image file.

Discrete Wavelet Transform (DWT).

The DWT method involves wavelet decomposition where wavelet transformation converts the images into different resolutions. Wavelet representation has both spatial and frequency components. Exemplary approaches for wavelet decomposition includes the Mallat algorithm, which can use a wavelet function such as the Daubechies functions (db1, db2, . . . ), and the a Trous algorithm, which merges dyadic wavelet and non-dyadic data in a simple and efficient procedure.

Two approaches for image fusion based on wavelet decomposition are the substitution method and the additive method. In the substitution method, after the wavelet coefficients of images from different sensors are obtained, some wavelet coefficients of one image are substituted with wavelet coefficients of the other image, followed by an inverse wavelet transform. In the additive method, wavelet planes of one image are produced and added to the other image directly, or are added or to an intensity component extracted from the other image. Some embodiments may include a transformation step.

For further details on exemplary image fusion techniques, see the following references, the entire contents of each of which is hereby incorporated by reference herein: H arris et al., 1990, "IHS transform for the integration of radar imagery with other remotely sensed data," Photogrammetric Engineering and Remote Sensing, 56(12), 1631-1641; Phol and van Genderen, 1998, "Multisensor image fusion in remote sensing: concepts, methods and applications," International Journal of Remote Sensing, 19(5), 823-854; Chavez et al., 1991, "Comparison of three different methods to merge multi-resolution and multi-sectoral data: Landsat™ and SPOT Panchromatic," Photogrammetric Engineering and Remote Sensing, 57(3), 295-303; Pellemans et al., 1993, "Merging multispectral and panchromatic SPOT images with respect to radiometric properties of the sensor," Photogrammetric Engineering and Remote Sensing, 59(1), 81-87; Nunez et al., 1999, "Multiresolution based image fusion with additive wavelet decomposition," IEEE Transactions on Geoscience and Remote Sensing, 37(3), 1204-1211; Steinnocher, 1997, "Applications of adaptive filters for multisensoral image fusion," Proceedings of the International Geoscience and Remote Sensing Symposium (IGARASS '97), Singapore, August 1997, 910-912; and Chavez and Kwarteng, 1989, "Extracting spectral contrast in Landsat Thematic Mapper image data using selective principal component analysis," Photogrammetric Engineering and Remote Sensing, 55(3), 339-348.

iii. Processor Subsystem Architecture

Figure 6:
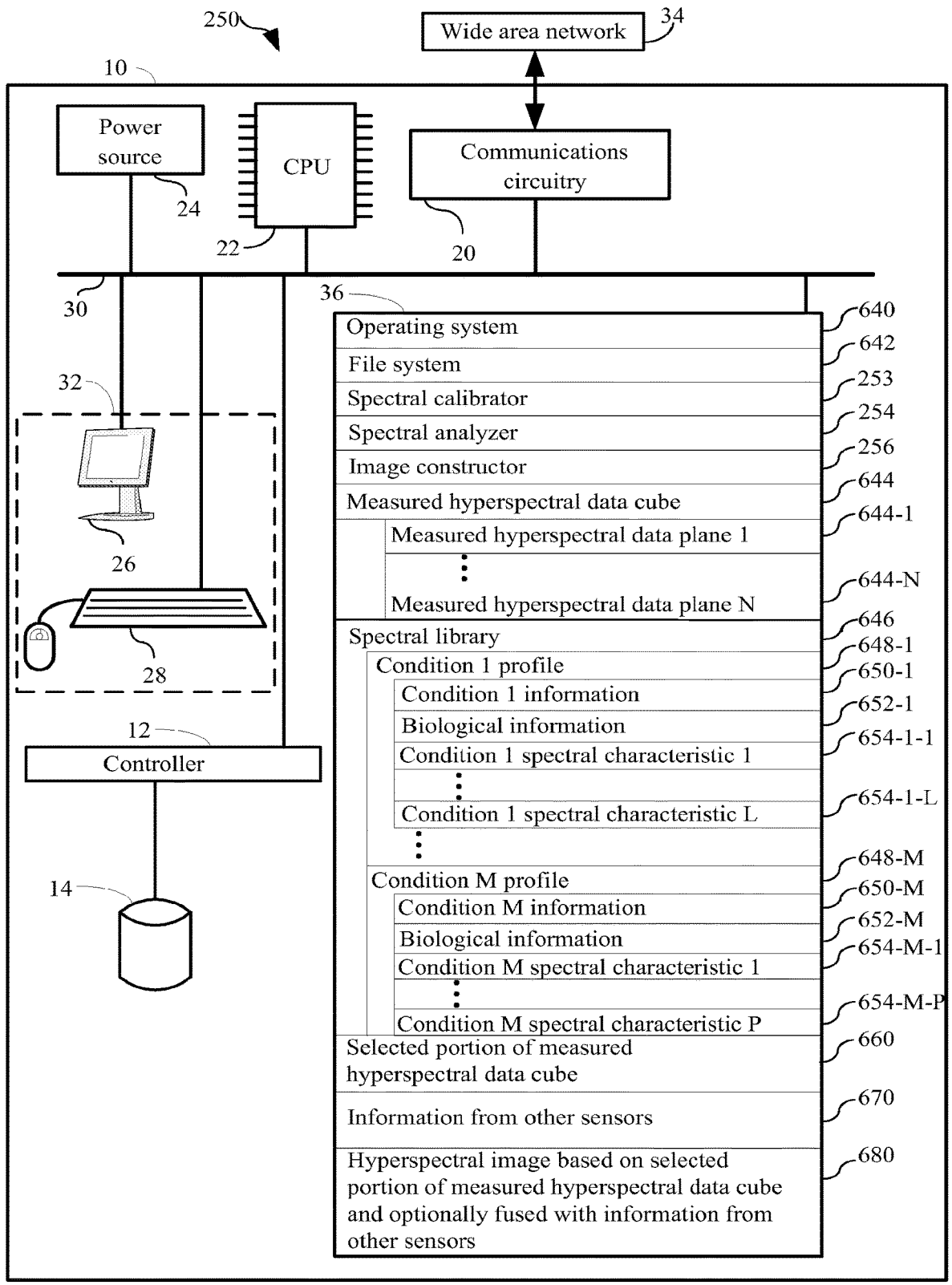
FIG. 6 schematically illustrates an embodiment of a processing subsystem, according to some embodiments.

FIG. 6 schematically illustrates an exemplary embodiment of processor subsystem 250. The subsystem 250 includes a computer system 10 having:

a central processing unit 22;

a main non-volatile storage unit 14, for example a hard disk drive, for storing software and data, the storage unit 14 controlled by storage controller 12;

a system memory 36, preferably high speed random-access memory (RAM), for storing system control programs, data, and application programs, including programs and data loaded from non-volatile storage unit 14; system memory 36 may also include read-only memory (ROM);

a user interface 32, including one or more input devices (e.g., keyboard 28, a mouse) and a display 26 or other output device;

a network interface card 20 (communications circuitry) for connecting to any wired or wireless communication network 34 (e.g., a wide area network such as the Internet);

a power source 24 to power the aforementioned elements; and an internal bus 30 for interconnecting the aforementioned elements of the system.

Operation of computer 10 is controlled primarily by operating system (control software) 640, which is executed by central processing unit 22. Operating system (control software) 640 can be stored in system memory 36. In some embodiments, system memory 36 also includes:

a file system 642 for controlling access to the various files and data structures used herein;

the spectral calibrator 253 described above, including calibration information;

the spectral analyzer 254 described above;

the image constructor 256 described above;

the measured hyperspectral cube 644, which includes a plurality of measured hyperspectral data planes;

a spectral library 646;

the selected portion of the measured hyperspectral data cube 660;

information from one or more other sensors 670; and the hyperspectral image based on the selected portion of the measured hyperspectral data cube and optionally fused with information from other sensors 680.

The measured hyperspectral cube 644, spectral library 646, selected portion 660, information from other sensors, and the (fused) hyperspectral image can be stored in a storage module in system memory 36. The measured hyperspectral data cube 644, the portion selected thereof 660, the information from other sensors 670, and the hyperspectral image need not all be concurrently present, depending on which stages of the analysis that processor subsystem 250 has performed.

The system memory 36 optionally also includes one or more of the following modules, which are not illustrated in FIG. 6:

a fusion module for fusing a hyperspectral image with information from other sensors;

a trained data analysis algorithm for identifying a region of the subject's skin of biological interest using an image obtained by the system; for characterizing a region of the subject's skin of biological interest using an image obtained by the apparatus; and/or for determining a portion of a hyperspectral data cube that contains information about a biological insult in the subject's skin; and a communications module for transmitting "outline" or "shape" files to a third party, e.g., using network interface card 20.

As illustrated in FIG. 6, computer 10 includes a spectral library 646, which includes profiles 648 for a plurality of medical conditions, "Condition 1" through "Condition M." The profile 648 for each condition includes a set of spectral characteristics 654 that the spectral analyzer 254 can use to determine whether the region corresponding to the measured hyperspectral data cube 644 has condition 1. Each profile 648 also includes information about that condition 650, e.g., information about whether the condition is malignant or benign, options for treatment, etc. Each profile 648 also includes biological information 652, e.g., information that can be used to modify the detection conditions for subjects of different skin types. In some embodiments, the spectral library 646 is stored in a single database. In other embodiments, such data is instead stored in a plurality of databases that may or may not all be hosted by the same computer 10. In such embodiments, some of the data illustrated in FIG. 6 as being stored in memory 36 is stored on computer systems that are not illustrated by FIG. 6 but that are addressable by wide area network 34.

In some embodiments, the data illustrated in memory 36 of computer 10 is on a single computer (e.g., computer 10) and in other embodiments the data illustrated in memory 36 of computer 10 is hosted by several computers (not shown). In fact, all possible arrangements of storing the data illustrated in memory 36 of computer 10 on one or more computers can be used so long as these components are addressable with respect to each other across computer network 34 or by other electronic means. Thus, a broad range of computer systems can be used.

While examining a subject and viewing hyperspectral images of the subject, the physician can optionally provide input to processor subsystem 250 that modifies one or more parameters upon which the hyperspectral image is based. This input can be provided using input device 28. Among other things, processor subsystem 250 can be instructed to modify the spectral portion selected by spectral analyzer 254 (for example, to modify a threshold of analytical sensitivity) or to modify the appearance of the image generated by image constructor 256 (for example, to switch from an intensity map to a topological rendering). The processor subsystem 250 can be instructed to communicate instructions to illumination subsystem 210 to modify a property of the light used irradiate the subject (for example, a spectral characteristic, an intensity, or a polarization). The processor subsystem 250 can be instructed to communicate instructions to sensor subsystem 230 to modify the sensing properties of one of the sensors (for example, an exposure setting, a frame rate, an integration rate, or a wavelength to be detected). Other parameters can also be modified. For example, the processor subsystem 250 can be instructed to obtain a wide-view image of the subject for screening purposes, or to obtain a close-in image of a particular region of interest.

E. Display Subsystem

The display subsystem 270 obtains the hyperspectral image (which is optionally fused with information from other sensors) from the image constructor 256, and displays the image. In some embodiments, the display subsystem 270 includes a video display 271 for displaying the image and/or a projector 272 for projecting the image onto the subject. In embodiments including a project, the image can be projected such that representations of spectral features are projected directly onto, or approximately onto, the conditions or physiological structures that generated those spectral features.

For further details, see U.S. Provisional Patent Application No. 61/052,934, filed May 13, 2008 and entitled "Systems and Methods for Hyperspectral Medical Imaging Using Real-Time Projection of Spectral Information."

Optionally, the display subsystem 270 also displays a legend that contains additional information. For example, the legend can display information indicating the probability that a region has a particular medical condition, a category of the condition, a probable age of the condition, the boundary of the condition, information about treatment of the condition, information indicating possible new areas of interest for examination, and/or information indicating possible new information that could be useful to obtain a diagnosis, e.g., another test or another spectral area that could be analyzed.

3. Applications of Hyperspectral Medical Imaging

A hyperspectral image can be used to make a diagnosis while the subject is being examined, or any time after the image is obtained. However, there are many other potential applications of hyperspectral imaging, some of which are described below.

A. Personalized Database of Spectral Information

As described above, a hyperspectral image is generated by obtaining spectra from the subject, as well as by optionally obtaining the output of one or more additional sensors. These spectra, the hyperspectral image, and the output of other sensors constitute a personalized database of spectral information for a subject. Additional information can be added to the database over time, as the subject is subsequently examined using hyperspectral imaging and the results stored in the database.

Among other things, the database can be used to determine spectral changes in the subject over time. For example, during a first examination, a region of the subject's skin may have a particular spectral characteristic. During a later examination, the region may have a different spectral characteristic, representing a change in the medical condition of the skin. It may be that the skin was normal when it was first examined (e.g., lacked any noteworthy medical conditions) but obtained a medical condition that was observed during the later examination. Alternately, it may be that the skin had a medical condition when it was first examined, but the medical condition underwent a change that was observed during the subsequent examination, or a new medical condition occurred. The changes to the skin itself may be imperceptible to a physician's eyes, but can be made apparent through appropriate hyperspectral analysis. Thus, hyperspectral imaging using the subject's own skin as a baseline can allow for significantly earlier detection of medical conditions than would be possible using other examination techniques.

Figure 8A:
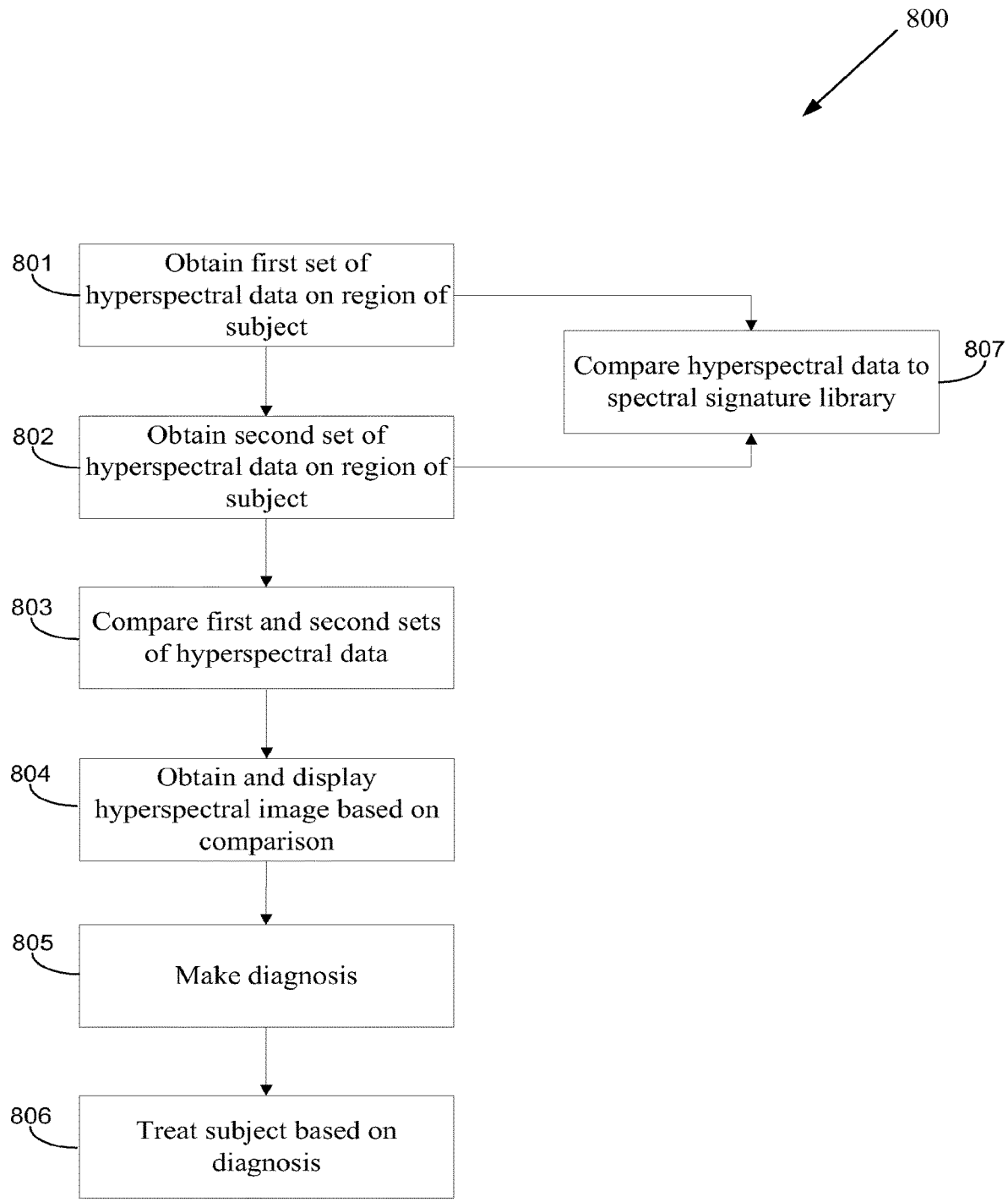
FIG. 8A illustrates a method of using a personalized database of spectral information for a subject, according to some embodiments.

FIG. 8A illustrates a method 800 of using a personalized database of hyperspectral information for a subject, according to some embodiments. First, a first set of hyperspectral data on a region of the subject is obtained (801), e.g., using the methods described herein. By "set of hyperspectral data" it is meant spectra, hyperspectral images, and sensor outputs relating to a particular region of skin. The first set of hyperspectral data can be stored in the personalized database of hyperspectral information for the subject. Optionally, the database also includes hyperspectral information for other subjects.

At some later time, a second set of hyperspectral data on a region of the subject is obtained (802). This second set can also be stored in the personalized database of hyperspectral information for the subject.

The second set of hyperspectral data is then compared to the first set of hyperspectral data (803). For example, selected portions of the first set of hyperspectral data can be compared to corresponding selected portions of the second set of hyperspectral data. As discussed above, differences between spectra of a particular region can represent a change in the medical condition of the region. Optionally, the first and/or second sets of hyperspectral data are also compared to a spectral signature library (806) in order to independently determine whether either of the sets includes information about a medical condition.

A hyperspectral image of the region is then generated based on the comparison (804), a diagnosis made based on the hyperspectral image (805), and the subject treated appropriately based on the diagnosis (806).

FIG. 8B illustrates one possible format for a database of hyperspectral information. Hyperspectral database 844 includes a plurality of subject records 846. There is no limit on the number of subject records 846 that can be held in hyperspectral database 844. Database 844 can hold as few as one subject record 846. More typically, database 844 holds between 1 and 100 subject records, more than 100 subject records, more than a thousand subject records, more than ten thousand subject records, more than 100 thousand subject records, or between 1 subject record and one million subject records.

Each subject record 846 preferably includes a subject identifier 848. As those skilled in the database arts will appreciate, a subject identifier 848 need not be explicitly enumerated in certain database systems. For instance, in some systems, a subject identifier 848 can simply be a subject record 846 identifier. However, in some embodiments, a subject identifier 48 can be a number that uniquely identifies a subject within a health care program.

Each subject record 846 optionally includes a demographic characterization 850 of respective subjects. In some embodiments, relevant portions of the demographic characterization 850 can be used in conjunction with the diagnosis to select a treatment regimen for a subject and/or can be used to characterize features that statistically correlate with the development of a medical condition (more below). The demographic characterization for a respective subject can include, for example, the following features of the subject: gender, marital status, ethnicity, primary language spoken, eye color, hair color, height, weight, social security number, name, date of birth, educational status, identity of the primary physician, name of a referring physician, a referral source, an indication as to whether the subject is disabled and a description of the disability, an indication as to whether the subject is a smoker, an indication as to whether the subject consumes alcohol, a residential address of the subject, and/or a telephone number of the subject. In addition, the demographic characterization 850 can include a name of an insurance carrier for an insurance policy held by the subject and/or a member identifier number for an insurance policy held by the subject. In some embodiments, the demographic characterization 850 also includes a family medical history, which can be used when diagnosing and/or treating the subject. The family medical history can include, for example, data such as whether or not a member of the subject's family has a particular medical condition.

Subject records 846 also include outputs from sensor subsystem 230 from different times the subject was examined. For example, subject records 846 can include hyperspectral data cubes 852, THz sensor outputs 854, and/or conventional images 856, or the outputs of any other sensors in sensor subsystem 230. Subject records 846 also include hyperspectral images 858, which may or may not be fused with information from other sensors/cameras.

Subject records 846 also include clinical characterizations 860. In some embodiments, clinical characterizations 860 include observations made by a subject's physician on a particular date. In some instances, the observations made by a physician include a code from the International Classification of Diseases, 9th Revision, prepared by the Department of Health and Human Services (ICD-9 codes), or an equivalent, and dates such observations were made. Clinical characterizations 860 complement information found within the hyperspectral data cubes 852, THz sensor outputs 854, conventional images 856, and/or hyperspectral images 858. The clinical characterizations 860 can include laboratory test results (e.g., cholesterol level, high density lipoprotein/low density lipoprotein ratios, triglyceride levels, etc.), statements made by the subject about their health, x-rays, biopsy results, and any other medical information typically relied upon by a doctor to make a diagnosis of the subject.

Subject records 846 further include diagnosis fields 862. Diagnosis fields 862 represents the diagnosis for the subject on a particular date, which can be based upon an analysis of the subject's hyperspectral data cubes 852, THz sensor outputs 854, conventional images 856, hyperspectral images 858, and/or the clinical characterizations 860 of the subject.

Subject data records 846 further include a subject treatment history 864. Treatment history 864 indicates the treatment given to a subject and when such treatment was given. Treatment history 864 includes all prescriptions given to the subject and all medical procedures undergone on the subject. In some embodiments, the medical procedures include Current Procedural Terminology (CPT) codes developed by the American Medical Association for the procedures performed on the subject, and a date such procedures were performed on the subject.

In some embodiments, a subject data record 846 can also include other data 866 such as pathology data (e.g., world health organization (classification, tumor, nodes, metastases staging, images), radiographic images (e.g., raw, processed, cat scans, positron emission tomography), laboratory data, Cerner electronic medical record data (hospital based data), risk factor data, access to a clinical reporting and data system, reference to vaccine production data/quality assurance, reference to a clinical data manager (e.g., OPTX), and/or reference to a cancer registry such as a research specimen banking database.

B. Temporal "Reachback"

The compilation of hyperspectral databases of one or more subjects can also be useful in characterizing the development over time of medical conditions. Among other things, as physicians learn new information about a condition, previously collected hyperspectral data can be re-analyzed to determine if that data contains information about that condition. For example, a physician in 2010 may discover and spectrally characterize a new medical condition. The physician can analyze previously collected hyperspectral data in a hyperspectral database (e.g., data from one or more subjects between 2008-2010), to determine whether that data includes information on the new medical condition. If the physician identifies that a subject in the database had the condition, even though the condition had not been recognized or characterized when the data was collected, the subject's data can be analyzed to characterize changes over time of the medical condition (e.g., using the method in FIG. 8A). The more subjects that have information in the hyperspectral database, and the greater amount of time that their information is compiled in the database, the greater the chance that the database will include information not only about a particular medical condition, but also its development over time and its characteristics in different types of subjects. The hyperspectral database can, for example, have the format illustrated in FIG. 8B.

Figure 9:
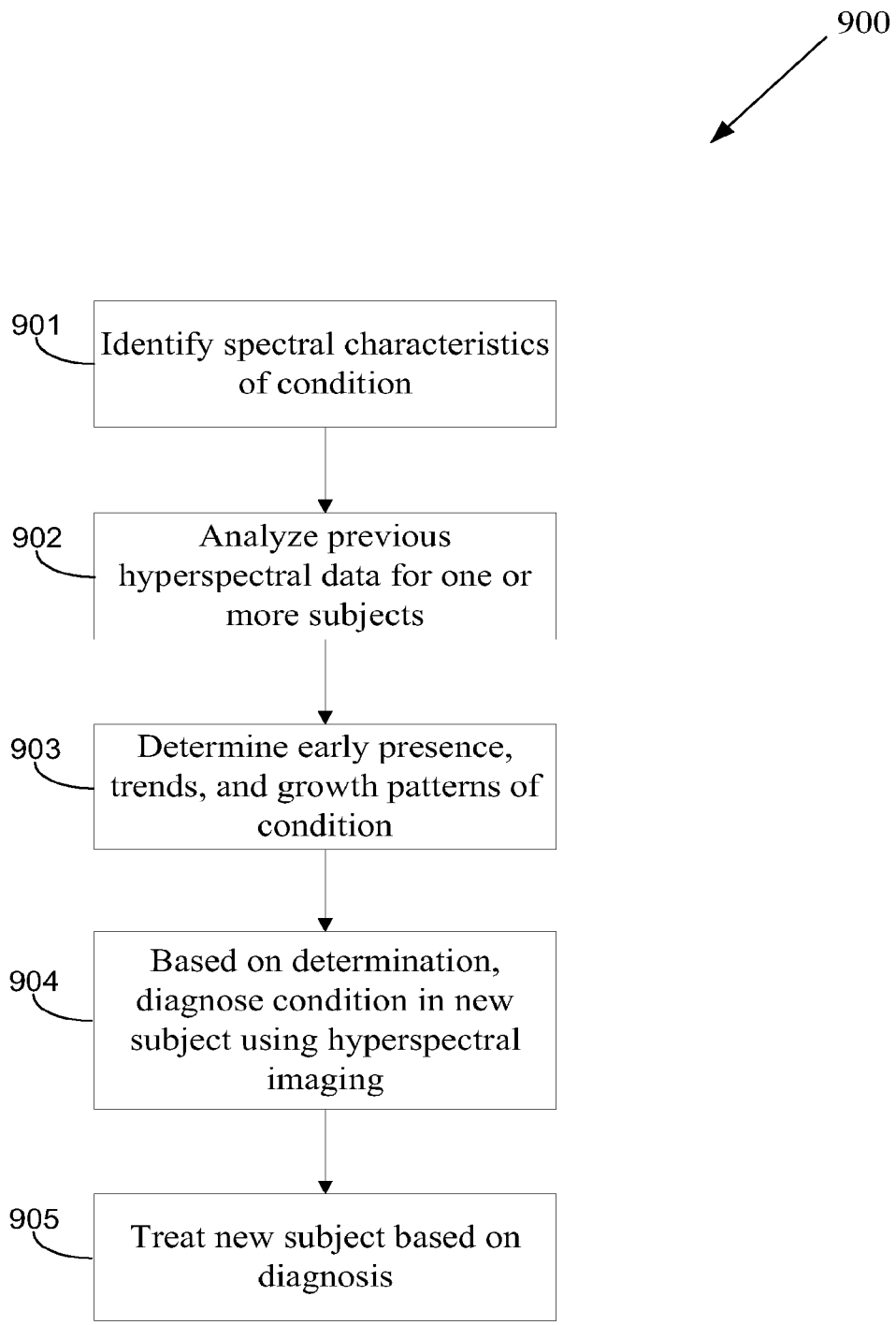
FIG. 9 illustrates a method of obtaining temporal information about a condition, according to some embodiments.

FIG. 9 illustrates a method 900 of obtaining temporal information about a condition, according to some embodiments. First, the spectral characteristics of a condition are identified (901), for example, using techniques described herein.

Then, previously collected hyperspectral data for one or more subjects is analyzed to determine whether any of those subjects had that condition, even though it may not have been recognized that they had the condition at the time the data was collected (902). The previously collected hyperspectral data can be stored in a hyperspectral database.

The hyperspectral data for each subject having the condition is then further analyzed to determine spectral characteristics associated with development of the condition (903). For example, characteristics of the early presence of the condition, trends of growth among different subjects, and patterns of growth within a given subject can all be characterized.

Based on the determination of the spectral characteristics of the condition in varying stages of growth over time, the condition can then be diagnosed in a new subject using hyperspectral imaging (904). The new subject can then be treated appropriately.

C. Use of Pattern Classification Techniques

Systems and methods for obtaining high resolution images of patient skin have been disclosed. Such systems and methods include the generation and storage of images taken using hyperspectral imaging, digital photography, LIDAR, and/or terahertz imaging, to name of few possible techniques. As discussed herein and in related U.S. Patent Application 61/052,934, filed May 13, 2008 and entitled "Systems and Methods for Hyperspectral Medical Imaging Using Real-Time Projection of Spectral Information," which is hereby incorporated by reference herein, the data obtained from a subject, particularly the subject's skin, can be fused images from any of a number of spectral sources (e.g., hyperspectral imaging, digital photography, LIDAR, and/or terahertz imaging, etc.), or unfused images taken from a single source.

Clearly, the amount of data that is taken from a subject is vast. For instance, in the case of hyperspectral imaging, a complete three-dimensional data cube containing several megabytes of data and representing a portion of the subject's skin, is generated. Much work is needed to analyze such spectral data regardless of whether such spectral data is from discrete spectral sources and represents the fusion of spectral data from two or more spectral sources. In such analysis, what is of interest is the identification of regions of the subject's skin that may have potential biological insult. Examples of biological insult are skin lesions. Of further interest is the characterization of such biological insults. Of further interest is the progression of such biological insults over time. Advantageously, as disclosed below in more detail, systems and methods that assist in such analysis are provided.

First, databases storing any of the data observed and measured using the methods disclosed herein may be electronically stored and recalled. Such stored images enable the identification and characterization of a subject's skin, and any biological insults thereon, over time.

Second, a wide variety of pattern classification techniques and/or statistical techniques can be used in accordance with the present disclosure to help in the analysis. For instance, such pattern classification techniques and/or statistical techniques can be used to (i) assist in identifying biological insults on a subject's skin, (ii) assist in characterizing such biological insults, and (iii) assist in analyzing the progression of such biological insults (e.g., detect significant changes in such lesions over time).

In one embodiment a database of spectral information, which may collected over time and/or for many different subjects is constructed. This database contains a wealth of information about medical conditions. In the example provided above, a physician is able to obtain information about a newly characterized medical condition, from a previously obtained set of spectral data. However, in some circumstances, indications of a medical condition may simply go unrecognized by physicians. Pattern classification is used to mine the database of spectral information in order to identify and characterize medical conditions (biological insults) that are characterized by observables. In some examples, such observables are values of specific pixels in an image of a subject's skin, patterns of values of specific groups of pixels in an image of a subject's skin, values of specific measured wavelengths or any other form of observable data that is directly present in the spectral data and/or that can be derived from the spectral data taken of a subject's skin. In some embodiments, pattern classification techniques such as artificial intelligence are used to analyze hyperspectral data cubes, the output of other sensors or cameras, and/or hyperspectral images themselves (which may or may not be fused with other information).

Figure 10:
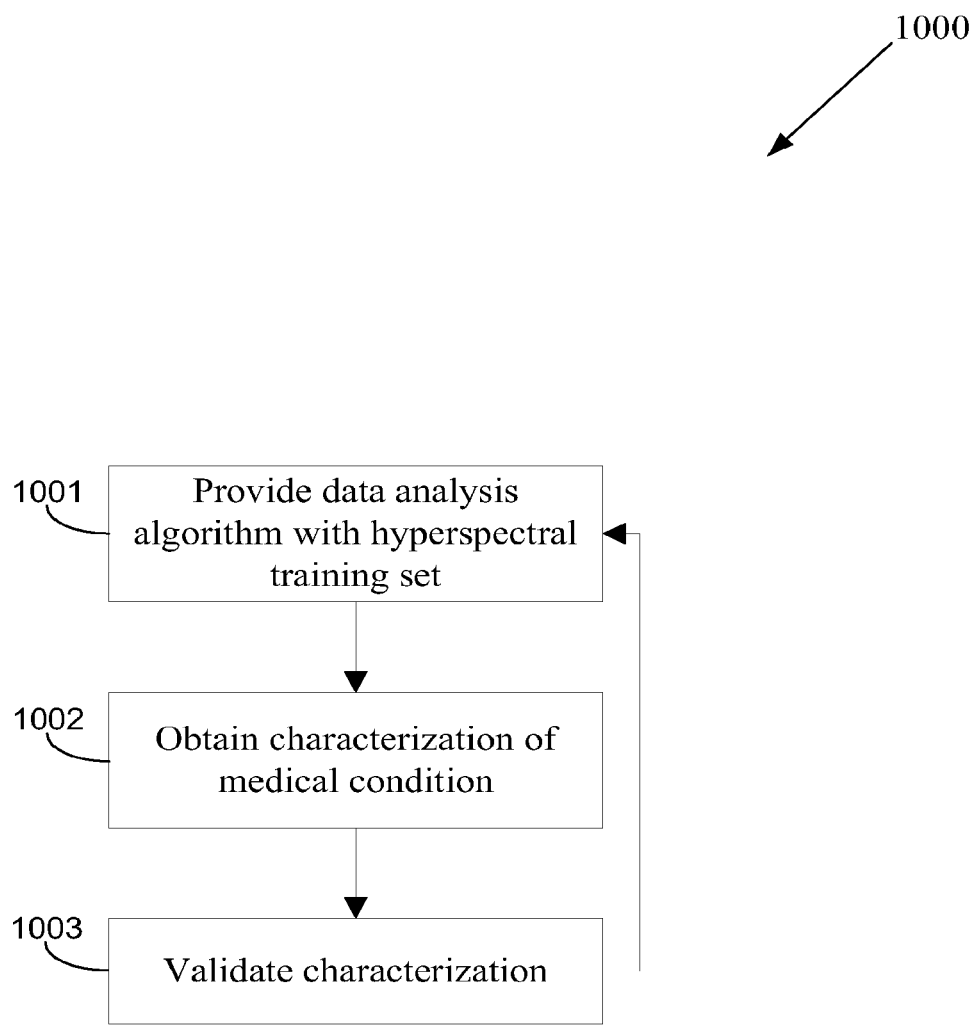
FIG. 10 illustrates a method of using pattern classification techniques, according to some embodiments.

FIG. 10 illustrates a method of using a database of spectral information from subject having known phenotypes to train a pattern classification technique or a statistical algorithm, referred to herein as a "data analysis algorithm." The trained data analysis algorithm can then be used to diagnose subjects with unknown phenotypes. The data analysis algorithm is provided with a spectral training set (1001). Exemplary data analysis algorithms are described below. The spectral training set is a set of spectral information (e.g., hyperspectral data cubes, the output of other sensors or cameras, and/or hyperspectral images) which may or may not be fused, which contains characterized information). For instance, in one example, the spectral data includes information from a single sensor (e.g., solely a hyperspectral sensor), discrete information from multiple sensors, and/or fused information from multiple sensors from subjects that have a known medical condition.

As is known in the pattern classification arts, such training information includes at least two types of data, for instance data from subjects that have one medical condition and data from subjects that have another medical condition. See, for example, Golub et al., 1999, Science 531, pp. 531-537, which is hereby incorporated by reference herein, in which several different classifiers were built using a training set of 38 bone marrow samples, 27 of which were acute lymphoblastic leukemia and 11 of which were acute myeloid leukemia. Once trained, a data analysis algorithm can be used to classify new subjects. For instance in the case of Golub et al., the trained data analysis algorithm can be used to determine whether a subject has acute lymphoblastic leukemia or acute myeloid leukemia. In the present disclosure, a data analysis algorithm can be trained to identify, characterize, or discover a change in a specific medical condition, such as a biological insult in the subject's skin. Based on the spectral training set stored, for example in a database, the data analysis algorithm develops a model for identifying a medical condition such as lesion, characterizing a medical condition such as a lesion, or detecting a significant change in the medical condition.

In some embodiments, the trained data analysis algorithm analyzes spectral information in a subject, in order to identify, characterize, or discover a significant change in a specific medical condition. Based on the result of the analysis, the trained data analysis algorithm obtains a characterization of a medical condition (1002) in a subject in need of characterization. The characterization is then validated (1003), for example, by verifying that the subject has the medical condition identified by the trained data analysis algorithm using independent verification methods such as follow up tests or human inspection. In cases where the characterization identified by the trained data analysis algorithm is incorrectly called (e.g., the characterization provides a false positive or a false negative), the trained data analysis algorithm can be retrained with another training set so that the data analysis algorithm can be improved.

As described in greater detail below, a model for recognizing a medical condition can be developed by (i) training a decision rule using spectral data from a training set and (ii) applying the trained decision rule to subjects having unknown biological characterization. If the trained decision rule is found to be accurate, the trained decision rule can be used to determine whether any other set of spectral data contains information indicative of a medical condition. The input to the disclosed decision rules is application dependent. In some instances, the input is raw digital feed from any of the spectral sources disclosed herein, either singly or in fused fashion. In some instances, the input to the disclosed decision rules is stored digital feed from any of the spectral sources disclosed herein, either singly or in fused fashion, taken from a database of such stored data. In some embodiment, the input to a decision rule is an entire cube of hyperspectral data and the output is one or more portions of the cube that are of the most significant interest.

For further details on the existing body of pattern recognition and prediction algorithms for use in data analysis algorithms for constructing decision rules, see, for example, National Research Council; Panel on Discriminant Analysis Classification and Clustering, Discriminant Analysis and Clustering, Washington, D.C.: National Academy Press, the entire contents of which are hereby incorporated by reference herein. Furthermore, the techniques described in Dudoit et al., 2002, "Comparison of discrimination methods for the classification of tumors using gene expression data." JASA 97; 77-87, the entire contents of which are hereby incorporated by reference herein, can be used to develop such decision rules.

Relevant algorithms for decision rule include, but are not limited to: discriminant analysis including linear, logistic, and more flexible discrimination techniques (see, e.g., Gnanadesikan, 1977, *Methods for Statistical Data Analysis of Multivariate Observations*, New York: Wiley 1977; tree-based algorithms such as classification and regression trees (CART) and variants (see, e.g., Breiman, 1984, *Classification and Regression Trees*, Belmont, Calif.: Wadsworth International Group; generalized additive models (see, e.g., Tibshirani, 1990, *Generalized Additive Models*, London: Chapman and Hall; neural networks (see, e.g., Neal, 1996, *Bayesian Learning for Neural Networks*, New York: Springer-Verlag; and Insua, 1998, Feedforward neural networks for nonparametric regression In: *Practical Nonparametric and Semiparametric Bayesian Statistics*, pp. 181-194, New York: Springer, the entire contents of each of which are hereby incorporated by reference herein. Other suitable data analysis algorithms for decision rules include, but are not limited to, logistic regression, or a nonparametric algorithm that detects differences in the distribution of feature values (e.g., a Wilcoxon Signed Rank Test (unadjusted and adjusted)).

The decision rule can be based upon two, three, four, five, 10, 20 or more measured values, corresponding to measured observables from one, two, three, four, five, 10, 20 or more spectral data sets. In one embodiment, the decision rule is based on hundreds of observables or more. Observables in the spectral data sets are, for example, values of specific pixels, patterns of values of specific groups of pixels, values of specific measured wavelengths or any other form of observable data that is directly present in the spectral data and/or that can be derived from the spectral data. Decision rules may also be built using a classification tree algorithm. For example, each spectral data set from a training population can include at least three observables, where the observables are predictors in a classification tree algorithm (more below). In some embodiments, a decision rule predicts membership within a population (or class) with an accuracy of at least about at least about 70%, of at least about 75%, of at least about 80%, of at least about 85%, of at least about 90%, of at least about 95%, of at least about 97%, of at least about 98%, of at least about 99%, or about 100%.

Additional suitable data analysis algorithms are known in the art, some of which are reviewed in Hastie et al., supra. Examples of data analysis algorithms include, but are not limited to: Classification and Regression Tree (CART), Multiple Additive Regression Tree (MART), Prediction Analysis for Microarrays (PAM), and Random Forest analysis. Such algorithms classify complex spectra and/or other information in order to distinguish subjects as normal or as having a particular medical condition. Other examples of data analysis algorithms include, but are not limited to, ANOVA and nonparametric equivalents, linear discriminant analysis, logistic regression analysis, nearest neighbor classifier analysis, neural networks, principal component analysis, quadratic discriminant analysis, regression classifiers and support vector machines. Such algorithms may be used to construct a decision rule and/or increase the speed and efficiency of the application of the decision rule and to avoid investigator bias, one of ordinary skill in the art will realize that computer-based algorithms are not required to carry out the disclosed methods.

I. Decision Trees

One type of decision rule that can be constructed using spectral data is a decision tree. Here, the "data analysis algorithm" is any technique that can build the decision tree, whereas the final "decision tree" is the decision rule. A decision tree is constructed using a training population and specific data analysis algorithms. Decision trees are described generally by Duda, 2001, Pattern Classification, John Wiley & Sons, Inc., New York. pp. 395-396, which is hereby incorporated by reference herein. Tree-based methods partition the feature space into a set of rectangles, and then fit a model (like a constant) in each one.

The training population data includes observables associated with a medical condition. Exemplary observables are values of specific pixels, patterns of values of specific groups of pixels, values of specific measured wavelengths or any other form of observable data that is directly present in the spectral data and/or that can be derived from the spectral data. One specific algorithm that can be used to construct a decision tree is a classification and regression tree (CART). Other specific decision tree algorithms include, but are not limited to, ID3, C4.5, MART, and Random Forests. CART, ID3, and C4.5 are described in Duda, 2001, Pattern Classification, John Wiley & Sons, Inc., New York. pp. 396-408 and pp. 411-412, the entire contents of which are hereby incorporated by reference herein. CART, MART, and C4.5 are described in Hastie et al., 2001, The Elements of Statistical Learning, Springer-Verlag, New York, Chapter 9, the entire contents of which are hereby incorporated by reference herein. Random Forests are described in Breiman, 1999, "Random Forests-Random Features," Technical Report 567, Statistics Department, U.C. Berkeley, September 1999, the entire contents of which are hereby incorporated by reference herein.

In some embodiments, decision trees are used to classify subjects using spectral data sets. Decision tree algorithms belong to the class of supervised learning algorithms. The aim of a decision tree is to induce a classifier (a tree) from real-world example data. This tree can be used to classify unseen examples that have not been used to derive the decision tree. As such, a decision tree is derived from training data. Exemplary training data contains spectral data for a plurality of subjects (the training population), each of which has the medical condition. The following algorithm describes an exemplary decision tree derivation:

```
Tree(Examples,Class,Features)
    Create a root node
    If all Examples have the same Class value, give the root this label
    Else if Features is empty label the root according to the most common
        value
    Else begin
        Calculate the information gain for each Feature
            Select the Feature A with highest information gain and
        make this the root Feature
            For each possible value, v, of this Feature
                Add a new branch below the root, corresponding to
                    A = v
                Let Examples(v) be those examples with A = v
                    If Examples(v) is empty, make the new branch a
                        leaf node
            labeled with the most common value among Examples
                    Else let the new branch be the tree created by
            Tree(Examples(v),Class,Features - {A})
    End
```

In general, there are a number of different decision tree algorithms, many of which are described in Duda, Pattern Classification, Second Edition, 2001, John Wiley & Sons, Inc. Decision tree algorithms often require consideration of feature processing, impurity measure, stopping criterion, and pruning Specific decision tree algorithms include, but are not limited to classification and regression trees (CART), multivariate decision trees, ID3, and C4.5.

In one approach, when a decision tree is used, the members of the training population are randomly divided into a training set and a test set. For example, in one embodiment, two thirds of the members of the training population are placed in the training set and one third of the members of the training population are placed in the test set. The spectral data of the training set is used to construct the decision tree. Then, the ability for the decision tree to correctly classify members in the test set is determined. In some embodiments, this computation is performed several times for a given combination of spectral data. In each computational iteration, the members of the training population are randomly assigned to the training set and the test set. Then, the quality of the spectral data is taken as the average of each such iteration of the decision tree computation.

In addition to univariate decision trees in which each split is based on a feature value for a corresponding phenotype represented by the spectral data set, or the relative values of two such observables, multivariate decision trees can be implemented as a decision rule. In such multivariate decision trees, some or all of the decisions actually include a linear combination of feature values for a plurality of observables. Such a linear combination can be trained using known techniques such as gradient descent on a classification or by the use of a sum-squared-error criterion. To illustrate such a decision tree, consider the expression:

$$0.04x_1 + 0.16x_2 < 500$$

Here, $x_1$ and $x_2$ refer to two different values for two different observables in the spectral data set. Such observables in the spectral data set can be, for example, values of specific pixels, patterns of values of specific groups of pixels, values of specific measured wavelengths or any other form of observable data that is directly present in the spectral data and/or that can be derived from the spectral data. To poll the decision rule, the values for $x_1$ and $x_2$ are obtained from the measurements obtained from the spectra of unclassified subject. These values are then inserted into the equation. If a value of less than 500 is computed, then a first branch in the decision tree is taken. Otherwise, a second branch in the decision tree is taken. Multivariate decision trees are described in Duda, 2001, *Pattern Classification*, John Wiley & Sons, Inc., New York, pp. 408-409, which is hereby incorporated by reference herein.

Another approach that can be used is multivariate adaptive regression splines (MARS). MARS is an adaptive procedure for regression, and is well suited for the high-dimensional problems involved with the analysis of spectral data. MARS can be viewed as a generalization of stepwise linear regression or a modification of the CART method to improve the performance of CART in the regression setting. MARS is described in Hastie et al., 2001, *The Elements of Statistical Learning*, Springer-Verlag, New York, pp. 283-295, which is hereby incorporated by reference in its entirety.

II. Predictive Analysis of Microarrays (PAM)

One approach to developing a decision rule using values for observables in the spectral data is the nearest centroid classifier. Such a technique computes, for each biological class (e.g., has lesion, does not have lesion), a centroid given by the average values of observable from specimens in the biological class, and then assigns new samples to the class whose centroid is nearest. This approach is similar to k-means clustering except clusters are replaced by known classes. This algorithm can be sensitive to noise when a large number of observables are used. One enhancement to the technique uses shrinkage: for each observable, differences between class centroids are set to zero if they are deemed likely to be due to chance. This approach is implemented in the Prediction Analysis of Microarray, or PAM. See, for example, Tibshirani et al., 2002, *Proceedings of the National Academy of Science USA* 99; 6567-6572, which is hereby incorporated by reference herein in its entirety. Shrinkage is controlled by a threshold below which differences are considered noise. Observables that show no difference above the noise level are removed. A threshold can be chosen by cross-validation. As the threshold is decreased, more observables are included and estimated classification errors decrease, until they reach a bottom and start climbing again as a result of noise observables—a phenomenon known as overfitting.

III. Bagging, Boosting, and the Random Subspace Method

Bagging, boosting, the random subspace method, and additive trees are data analysis algorithms known as combining techniques that can be used to improve weak decision rules. These techniques are designed for, and usually applied to, decision trees, such as the decision trees described above. In addition, such techniques can also be useful in decision rules developed using other types of data analysis algorithms such as linear discriminant analysis.

In bagging, one samples the training set, generating random independent bootstrap replicates, constructs the decision rule on each of these, and aggregates them by a simple majority vote in the final decision rule. See, for example, Breiman, 1996, Machine Learning 24, 123-140; and Efron & Tibshirani, *An Introduction to Boostrap*, Chapman & Hall, New York, 1993, the entire contents of which are hereby incorporated by reference herein.

In boosting, decision rules are constructed on weighted versions of the training set, which are dependent on previous classification results. Initially, all features under consideration have equal weights, and the first decision rule is constructed on this data set. Then, weights are changed according to the performance of the decision rule. Erroneously classified biological samples get larger weights, and the next decision rule is boosted on the reweighted training set. In this way, a sequence of training sets and decision rules is obtained, which is then combined by simple majority voting or by weighted majority voting in the final decision rule. See, for example, Freund & Schapire, "Experiments with a new boosting algorithm," Proceedings 13th International Conference on Machine Learning, 1996, 148-156, the entire contents of which are hereby incorporated by reference herein.

To illustrate boosting, consider the case where there are two phenotypes exhibited by the population under study, phenotype 1 (e.g., sick), and phenotype 2 (e.g., healthy). Given a vector of predictor observables (e.g., a vector of values that represent such observables) from the training set data, a decision rule G(X) produces a prediction taking one of the type values in the two value set: {phenotype 1, phenotype 2}. The error rate on the training sample is $$\overline{err} = \frac{1}{N}\sum_{i=1}^{N} I(y_i \neq G(x_i))$$

where N is the number of subjects in the training set (the sum total of the subjects that have either phenotype 1 or phenotype 2). For example, if there are 49 subjects that are sick and 72 subjects that are healthy, N is 121. A weak decision rule is one whose error rate is only slightly better than random guessing. In the boosting algorithm, the weak decision rule is repeatedly applied to modified versions of the data, thereby producing a sequence of weak decision rules $G_m(x)$, m=1, 2, . . . , M. The predictions from all of the decision rules in this sequence are then combined through a weighted majority vote to produce the final decision rule:

$$G(x) = \text{sign}\left(\sum_{m=1}^{M} \alpha_m G_m(x)\right)$$

Here $\alpha_1, \alpha_2, \ldots, \alpha_M$ are computed by the boosting algorithm and their purpose is to weigh the contribution of each respective decision rule Gm(x). Their effect is to give higher influence to the more accurate decision rules in the sequence.

The data modifications at each boosting step consist of applying weights $w_1, w_2, \ldots, w_n$ to each of the training observations $(x_i, y_i)$, i=1, 2, ..., N. Initially all the weights are set to $w_i=1/N$, so that the first step simply trains the decision rule on the data in the usual manner. For each successive iteration m=2, 3, ..., M the observation weights are individually modified and the decision rule is reapplied to the weighted observations. At step m, those observations that were misclassified by the decision rule $G_m-1$ (x) induced at the previous step have their weights increased, whereas the weights are decreased for those that were classified correctly. Thus as iterations proceed, observations that are difficult to correctly classify receive ever-increasing influence. Each successive decision rule is thereby forced to concentrate on those training observations that are missed by previous ones in the sequence.

The exemplary boosting algorithm is summarized as follows:
1. Initialize the observation weights $w_i=1/N$, i=1, 2, ..., N.
2. For m=1 to M:
   (a) Fit a decision rule $G_m(x)$ to the training set using weights $w_i$.
   (b) Compute $$err_m = \frac{\sum_{i=1}^{N} w_i I(y_i \neq G_m(x_i))}{\sum_{i=1}^{N} w_i}$$

(c) Compute $\alpha_m = \log((1-err_m)/err_m)$.
   (d) Set $w_i \leftarrow w_i \cdot \exp[\alpha_m \cdot I(y_i \neq G_m(x_i))]$, i=1, 2, ..., N.
3. Output $G(x) = \text{sign}[\sum_{m=1}^{M} \alpha_m G_m(x)]$ In one embodiment in accordance with this algorithm, each object is, in fact, an observable. Furthermore, in the algorithm, the current decision rule $G_m(x)$ is induced on the weighted observations at line 2a. The resulting weighted error rate is computed at line 2b. Line 2c calculates the weight $\alpha_m$ given to $G_m(x)$ in producing the final classifier G(x) (line 3). The individual weights of each of the observations are updated for the next iteration at line 2d. Observations misclassified by $G_m(x)$ have their weights scaled by a factor $\exp(a_m)$, increasing their relative influence for inducing the next classifier $G_m+1(x)$ in the sequence. In some embodiments, modifications are used of the boosting methods in Freund and Schapire, 1997, Journal of Computer and System Sciences 55, pp. 119-139, the entire contents of which are hereby incorporated by reference herein. See, for example, Hasti et al., *The Elements of Statistical Learning*, 2001, Springer, New York, Chapter 10, the entire contents of which are hereby incorporated by reference herein.

For example, in some embodiments, observable preselection is performed using a technique such as the nonparametric scoring methods of Park et al., 2002, Pac. Symp. Biocomput. 6, 52-63, the entire contents of which are hereby incorporated by reference herein. Observable preselection is a form of dimensionality reduction in which the observables that discriminate between phenotypic classifications the best are selected for use in the classifier. Examples of observables include, but are not limited to, values of specific pixels, patterns of values of specific groups of pixels, values of specific measured wavelengths or any other form of observable data that is directly present in the spectral data and/or that can be derived from the spectral data. Next, the Logit-Boost procedure introduced by Friedman et al., 2000, Ann Stat 28, 337-407, the entire contents of which are hereby incorporated by reference herein, is used rather than the boosting procedure of Freund and Schapire. In some embodiments, the boosting and other classification methods of Ben-Dor et al., 2000, Journal of Computational Biology 7, 559-583, hereby incorporated by reference in its entirety, are used. In some embodiments, the boosting and other classification methods of Freund and Schapire, 1997, Journal of Computer and System Sciences 55, 119-139, the entire contents of which are hereby incorporated by reference herein, are used.

In the random subspace method, decision rules are constructed in random subspaces of the data feature space. These decision rules are usually combined by simple majority voting in the final decision rule. See, for example, Ho, "The Random subspace method for constructing decision forests," IEEE Trans Pattern Analysis and Machine Intelligence, 1998; 20(8): 832-844, the entire contents of which are incorporated by reference herein.

IV. Multiple Additive Regression Trees

Multiple additive regression trees (MART) represent another way to construct a decision rule. A generic algorithm for MART is:
1. Initialize $f_0(x) = \arg \min \gamma \Sigma_{i=1}^{N} L(y_i, \gamma)$.
2. For m=1 to M:
   (a) For i=1, 2, ..., N compute $$r_{im} = -\left[\frac{\partial L(y_i, f(x_i))}{\partial f(x_i)}\right]_{f=f_{m-1}}$$

(b) Fit a regression tree to the targets $r_{im}$ giving terminal regions $R_{jm}$, j=1, 2, ..., $J_m$.
   (c) For j=1, 2, ..., $J_m$ compute $$\gamma_{jm} = \arg\min_{\gamma} \sum_{x_i \in R_{jm}} L(y_i, f_{m-1}(x_i) + \gamma).$$

(d) Update $f_m(x) = f_{m-1}(x) + \Sigma_{j=1}^{J_m} \gamma_{jm} I(x \in R_{jm})$
3. Output $\hat{f}(x) = f_M(x)$.

Specific algorithms are obtained by inserting different loss criteria L(y,f(x)). The first line of the algorithm initializes to the optimal constant model, which is just a single terminal node tree. The components of the negative gradient computed in line 2(a) are referred to as generalized pseudo residuals, r. Gradients for commonly used loss functions are summarized in Table 10.2, of Hastie et al., 2001, *The Elements of Statistical Learning*, Springer-Verlag, New York, p. 321, the entire contents of which are hereby incorporated by reference herein. The algorithm for classification is similar and is described in Hastie et al., Chapter 10, the entire contents of which are hereby incorporated by reference herein. Tuning parameters associated with the MART procedure are the number of iterations M and the sizes of each of the constituent trees $J_m$, m=1, 2, ..., M.

V. Decision Rules Derived by Regression

In some embodiments, a decision rule used to classify subjects is built using regression. In such embodiments, the decision rule can be characterized as a regression classifier, such as a logistic regression classifier. Such a regression classifier includes a coefficient for a plurality of observables from the spectral training data that is used to construct the classifier. Examples of such observables in the spectral training set include, but are not limited to values of specific pixels, patterns of values of specific groups of pixels, values of specific measured wavelengths or any other form of observable data that is directly present in the spectral data and/or that can be derived from the spectral data. In such embodiments, the coefficients for the regression classifier are computed using, for example, a maximum likelihood approach.

In one specific embodiment, the training population includes a plurality of trait subgroups (e.g., three or more trait subgroups, four or more specific trait subgroups, etc.). These multiple trait subgroups can correspond to discrete stages of a biological insult such as a lesion. In this specific embodiment, a generalization of the logistic regression model that handles multicategory responses can be used to develop a decision that discriminates between the various trait subgroups found in the training population. For example, measured data for selected observables can be applied to any of the multi-category logit models described in Agresti, *An Introduction to Categorical Data Analysis*, 1996, John Wiley & Sons, Inc., New York, Chapter 8, the entire contents of which are hereby incorporated by reference herein, in order to develop a classifier capable of discriminating between any of a plurality of trait subgroups represented in a training population.

VI. Neural Networks

In some embodiments, spectral data training sets can be used to train a neural network. A neural network is a two-stage regression or classification decision rule. A neural network has a layered structure that includes a layer of input units (and the bias) connected by a layer of weights to a layer of output units. For regression, the layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et al., 2001, *Pattern Classification*, Second Edition, John Wiley & Sons, Inc., New York; and Hastie et al., 2001, *The Elements of Statistical Learning*, Springer-Verlag, New York, the entire contents of each of which are hereby incorporated by reference herein. Neural networks are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, N.Y., the entire contents of each of which are incorporated by reference herein. What are disclosed below is some exemplary forms of neural networks.

One basic approach to the use of neural networks is to start with an untrained network, present a training pattern to the input layer, and to pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. For regression, this error can be sum-of-squared errors. For classification, this error can be either squared error or cross-entropy (deviation). See, e.g., Hastie et al., 2001, *The Elements of Statistical Learning*, Springer-Verlag, New York, the entire contents of which are hereby incorporated by reference herein.

Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the classifier defined by the network topology. In batch training, all patterns are presented to the network before learning takes place. Typically, in batch training, several passes are made through the training data. In online training, each pattern is presented once and only once to the net.

In some embodiments, consideration is given to starting values for weights. If the weights are near zero, then the operative part of the sigmoid commonly used in the hidden layer of a neural network (see, e.g., Hastie et al., 2001, *The Elements of Statistical Learning*, Springer-Verlag, New York, the entire contents of which are hereby incorporated by reference herein) is roughly linear, and hence the neural network collapses into an approximately linear classifier. In some embodiments, starting values for weights are chosen to be random values near zero. Hence the classifier starts out nearly linear, and becomes nonlinear as the weights increase. Individual units localize to directions and introduce nonlinearities where needed. Use of exact zero weights leads to zero derivatives and perfect symmetry, and the algorithm never moves. Alternatively, starting with large weights often leads to poor solutions.

Since the scaling of inputs determines the effective scaling of weights in the bottom layer, it can have a large effect on the quality of the final solution. Thus, in some embodiments, at the outset all expression values are standardized to have mean zero and a standard deviation of one. This ensures all inputs are treated equally in the regularization process, and allows one to choose a meaningful range for the random starting weights. With standardization inputs, it is typical to take random uniform weights over the range $[-0.7, +0.7]$.

A recurrent problem in the use of three-layer networks is the optimal number of hidden units to use in the network. The number of inputs and outputs of a three-layer network are determined by the problem to be solved. In the present application, the number of inputs for a given neural network will equal the number of observables selected from the training population. Here, an observable can be, for example, measured values for specific pixels in an image, measured values for specific wavelengths in an image, where the image is from a single spectral source or from a fusion of two or more disparate spectral sources. The number of outputs for the neural network will typically be just one. However, in some embodiments, more than one output is used so that more than just two states can be defined by the network. For example, a multi-output neural network can be used to discriminate between healthy phenotypes, sick phenotypes, and various stages in between. If too many hidden units are used in a neural network, the network will have too many degrees of freedom and is trained too long, there is a danger that the network will overfit the data. If there are too few hidden units, the training set cannot be learned. Generally speaking, however, it is better to have too many hidden units than too few. With too few hidden units, the classifier might not have enough flexibility to capture the nonlinearities in the date; with too many hidden units, the extra weight can be shrunk towards zero if appropriate regularization or pruning, as described below, is used. In typical embodiments, the number of hidden units is somewhere in the range of 5 to 100, with the number increasing with the number of inputs and number of training cases.

One general approach to determining the number of hidden units to use is to apply a regularization approach. In the regularization approach, a new criterion function is constructed that depends not only on the classical training error, but also on classifier complexity. Specifically, the new criterion function penalizes highly complex classifiers; searching for the minimum in this criterion is to balance error on the training set with error on the training set plus a regularization term, which expresses constraints or desirable properties of solutions:

$$J = J_{pat} + \lambda J_{reg}.$$

The parameter $\lambda$ is adjusted to impose the regularization more or less strongly. In other words, larger values for $\lambda$ will tend to shrink weights towards zero: typically cross-validation with a validation set is used to estimate $\lambda$. This validation set can be obtained by setting aside a random subset of the training population. Other forms of penalty have been proposed, for example the weight elimination penalty (see, e.g., Hastie et al., 2001, *The Elements of Statistical Learning*, Springer-Verlag, New York, the entire contents of which are incorporated by reference herein).

Another approach to determine the number of hidden units to use is to eliminate—prune—weights that are least needed. In one approach, the weights with the smallest magnitude are eliminated (set to zero). Such magnitude-based pruning can work, but is nonoptimal; sometimes weights with small magnitudes are important for learning and training data. In some embodiments, rather than using a magnitude-based pruning approach, Wald statistics are computed. The fundamental idea in Wald Statistics is that they can be used to estimate the importance of a hidden unit (weight) in a classifier. Then, hidden units having the least importance are eliminated (by setting their input and output weights to zero). Two algorithms in this regard are the Optimal Brain Damage (OBD) and the Optimal Brain Surgeon (OBS) algorithms that use second-order approximation to predict how the training error depends upon a weight, and eliminate the weight that leads to the smallest increase in training error.

Optimal Brain Damage and Optimal Brain Surgeon share the same basic approach of training a network to local minimum error at weight w, and then pruning a weight that leads to the smallest increase in the training error. The predicted functional increase in the error for a change in full weight vector $\delta w$ is:

$$\delta J = \left(\frac{\partial J}{\partial w}\right)^t \cdot \delta w + \frac{1}{2} \delta w^t \cdot \frac{\partial^2 J}{\partial w^2} \cdot \delta w + O(\|\delta w\|^3)$$

where $$\frac{\partial^2 J}{\partial w^2}$$

is the Hessian matrix. The first term vanishes at a local minimum in error; third and higher order terms are ignored.

The general solution for minimizing this function given the constraint of deleting one weight is:

$$\delta w = -\frac{w_q}{[H^{-1}]_{qq}} H^{-1} \cdot u_q \text{ and } L_q = \frac{1}{2} - \frac{w_q^2}{[H^{-1}]_{qq}}$$

Here, $u_q$ is the unit vector along the qth direction in weight space and $L_q$ is approximation to the saliency of the weight q–the increase in training error if weight q is pruned and the other weights updated $\delta w$. These equations require the inverse of H. One method to calculate this inverse matrix is to start with a small value, $H_0^{-1} = \alpha^{-1} I$, where $\alpha$ is a small parameter—effectively a weight constant. Next the matrix is updated with each pattern according to $$H_{m+1}^{-1} = H_m^{-1} - \frac{H_m^{-1} X_{m+1} X_{m+1}^T H_m^{-1}}{\frac{n}{a_m} + X_{m+1}^T H_m^{-1} X_{m+1}} \qquad \text{(Eqn. 1)}$$

where the subscripts correspond to the pattern being presented and $a_m$ decreases with m. After the full training set has been presented, the inverse Hessian matrix is given by $H^{-1} = H_n^{-1}$. In algorithmic form, the Optimal Brain Surgeon method is:

```
begin initialize n_H, w, θ
    train a reasonably large network to minimum error
    do compute H⁻¹ by Eqn. 1 q* ← arg min w_q²/(2[H⁻¹]_qq) (saliency L_q)
              q w ← w − (w_q* / [H⁻¹]_q*q*) H⁻¹ e_q*  (saliency L_q)

until J(w) > θ
    return w
end
```

The Optimal Brain Damage method is computationally simpler because the calculation of the inverse Hessian matrix in line 3 is particularly simple for a diagonal matrix. The above algorithm terminates when the error is greater than a criterion initialized to be $\theta$. Another approach is to change line 6 to terminate when the change in J(w) due to elimination of a weight is greater than some criterion value. In some embodiments, the back-propagation neural network. See, for example Abdi, 1994, "A neural network primer," J. Biol System. 2, 247-283, the entire contents of which are incorporated by reference herein.

VII. Clustering

In some embodiments, observables in the spectral data sets such as values of specific pixels, patterns of values of specific groups of pixels, values of specific measured wavelengths or any other form of observable data that is directly present in the data or that can be derived from the data are used to cluster a training set. For example, consider the case in which ten such observables are used. Each member m of the training population will have values for each of the ten observable. Such values from a member m in the training population define the vector:

$X_{1m}\ X_{2m}\ X_{3m}\ X_{4m}\ X_{5m}\ X_{6m}\ X_{7m}\ X_{8m}\ X_{9m}\ X_{10m}$ where $X_{im}$ is the measured or derived value of the $i^{th}$ observable in a spectral data set m. If there are m spectral data sets in the training set, where each such data set corresponds to a subject having known phenotypic classification or each such data set corresponds to the same subject having known phenotypic classification but at a unique time point, selection of i observables will define m vectors. Note that there is no requirement that the measured or derived value of every single observable used in the vectors be represented in every single vector m. In other words, spectral data from a subject in which one of the $i^{th}$ observables is not found can still be used for clustering. In such instances, the missing observable is assigned either a "zero" or some other value. In some embodiments, prior to clustering, the values for the observables are normalized to have a mean value of zero and unit variance.

Those members of the training population that exhibit similar values for corresponding observables will tend to cluster together. A particular combination of observables is considered to be a good classifier when the vectors cluster into the trait groups found in the training population. For instance, if the training population includes class a: subjects that do not have the medical condition, and class b: subjects that do have the medical condition, a useful clustering classifier will cluster the population into two groups, with one cluster group uniquely representing class a and the other cluster group uniquely representing class b.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973.

More recently, Duda et al., Pattern Classification, $2^{nd}$ edition, John Wiley & Sons, Inc. New York, has been published. Pages 537-563 provide additional clustering details. More information on clustering techniques can be found in the following references, the entire contents of each of which are hereby incorporated by reference herein: Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

VIII. Principle Component Analysis

Principal component analysis (PCA) can be used to analyze observables in the spectral data sets such as values of specific pixels, patterns of values of specific groups of pixels, values of specific measured wavelengths or any other form of observable data that is directly present in the spectral data or that can be derived from the spectral data in order to construct a decision rule that discriminates subjects in the training set. Principal component analysis is a classical technique to reduce the dimensionality of a data set by transforming the data to a new set of variable (principal components) that summarize the features of the data. See, for example, Jolliffe, 1986, *Principal Component* Analysis, Springer, New York, which is hereby incorporated by reference in its entirety. Principal component analysis is also described in Draghici, 2003, *Data Analysis Tools for DNA Microarrays*, Chapman & Hall/CRC, which is hereby incorporated by reference in its entirety. What follows are some non-limiting examples of principal components analysis.

Principal components (PCs) are uncorrelated and are ordered such that the $k^{th}$ PC has the kth largest variance among PCs. The $k^{th}$ PC can be interpreted as the direction that maximizes the variation of the projections of the data points such that it is orthogonal to the first k–1 PCs. The first few PCs capture most of the variation in the data set. In contrast, the last few PCs are often assumed to capture only the residual 'noise' in the data.

PCA can also be used to create a classifier. In such an approach, vectors for selected observables can be constructed in the same manner described for clustering above. The set of vectors, where each vector represents the measured or derived values for the select observables from a particular member of the training population, can be viewed as a matrix. In some embodiments, this matrix is represented in a Free-Wilson method of qualitative binary description of monomers (Kubinyi, 1990, 3*D QSAR in drug design theory methods and applications*, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been considered.

Then, each of the vectors (where each vector represents a member of the training population, or each vector represents a member of the training population at a specific instance in time) is plotted. Many different types of plots are possible. In some embodiments, a one-dimensional plot is made. In this one-dimensional plot, the value for the first principal component from each of the members of the training population is plotted. In this form of plot, the expectation is that members of a first subgroup (e.g. those subjects that have a first type of lesion) will cluster in one range of first principal component values and members of a second subgroup (e.g., those subjects that have a second type of lesion) will cluster in a second range of first principal component values.

In one example, the training population includes two subgroups: "has lesion" and "does not have lesion." The first principal component is computed using the values of observables across the entire training population data set. Then, each member of the training set is plotted as a function of the value for the first principal component. In this example, those members of the training population in which the first principal component is positive are classified as "has lesion" and those members of the training population in which the first principal component is negative are classified as "does not have lesion."

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent subjects that have a first type of lesion and a second cluster of members in the two-dimensional plot will represent subjects that have a second type of lesion.

IX. Nearest Neighbor Analysis

Nearest neighbor classifiers are memory-based and require no classifier to be fit. Given a query point $x_0$, the k training points $x_{(r)}$, r, . . . , k closest in distance to $x_0$ are identified and then the point $x_0$ is classified using the k nearest neighbors. Ties can be broken at random. In some embodiments, Euclidean distance in feature space is used to determine distance as:

$$d_{(i)} = \|x_{(i)} - x_o\|.$$

In some embodiments, when the nearest neighbor algorithm is used, the observables in the spectral data used to compute the linear discriminant is standardized to have mean zero and variance 1.

The members of the training population can be randomly divided into a training set and a test set. For example, in one embodiment, two thirds of the members of the training population are placed in the training set and one third of the members of the training population are placed in the test set. A select combination of observables represents the feature space into which members of the test set are plotted. Observables in the spectral data include, but are not limited to values of specific pixels, patterns of values of specific groups of pixels, values of specific measured wavelengths or any other form of observable data that is directly present in the spectral data and/or that can be derived from the spectral data.

Next, the ability of the training set to correctly characterize the members of the test set is computed. In some embodiments, nearest neighbor computation is performed several times for a given combination of spectral features. In each iteration of the computation, the members of the training population are randomly assigned to the training set and the test set. Then, the quality of the combination of observables chosen to develop the classifier is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, *The Elements of Statistical Learning*, Springer, New York, each of which is hereby incorporated by reference in its entirety.

X. Linear Discriminant Analysis

Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. The feature values for selected combinations of observables across a subset of the training population serve as the requisite continuous independent variables. The trait subgroup classification of each of the members of the training population serves as the dichotomous categorical dependent variable. LDA seeks the linear combination of variables that maximizes the ratio of between-group variance and within-group variance by using the grouping information. Implicitly, the linear weights used by LDA depend on how the measured values of an observable across the training set separates in the two groups (e.g., a group a that has lesion type 1 and a group b that has lesion type b) and how these measured values correlate with the measured values of other observables. In some embodiments, LDA is applied to the data matrix of the N members in the training sample by K observables in a combination of observables. Observables in the spectral data sets are, for example, values of specific pixels, patterns of values of specific groups of pixels, values of specific measured wavelengths or any other form of observable data that is directly present in the spectral data and/or that can be derived from the spectral data. Then, the linear discriminant of each member of the training population is plotted. Ideally, those members of the training population representing a first subgroup (e.g. "sick" subjects) will cluster into one range of linear discriminant values (e.g., negative) and those member of the training population representing a second subgroup (e.g. "healthy" subjects) will cluster into a second range of linear discriminant values (e.g., positive). The LDA is considered more successful when the separation between the clusters of discriminant values is larger. For more information on linear discriminant analysis, see Duda, *Pattern Classification*, Second Edition, 2001, John Wiley & Sons, Inc; and Hastie, 2001, *The Elements of Statistical Learning*, Springer, New York; and Venables & Ripley, 1997, *Modern Applied Statistics with s-plus*, Springer, New York, each of which is hereby incorporated by reference in its entirety.

XI. Quadratic Discriminant Analysis

Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

XII. Support Vector Machines

In some embodiments, support vector machines (SVMs) are used to classify subjects using values of specific predetermined observables. Observables in the training data, include, but are not limited to values of specific pixels, patterns of values of specific groups of pixels, values of specific measured wavelengths or any other form of observable data that is directly present in the spectral data and/or that can be derived from the spectral data. SVMs are a relatively new type of learning algorithm. See, for example, Cristianini and Shawe-Taylor, 2000, *An Introduction to Support Vector Machines*, Cambridge University Press, Cambridge; Boser et al., 1992, "A training algorithm for optimal margin classifiers," in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York; Mount, 2001, *Bioinformatics: sequence and genome analysis*, Cold Spring Harbor Laboratory Press, Cold Spring Harbor, N.Y., Duda, *Pattern Classification*, Second Edition, 2001, John Wiley & Sons, Inc.; and Hastie, 2001, *The Elements of Statistical Learning*, Springer, New York; and Furey et al., 2000, Bioinformatics 16, 906-914, each of which is hereby incorporated by reference in its entirety.

When used for classification, SVMs separate a given set of binary labeled data training data with a hyper-plane that is maximally distanced from them. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

In one approach, when a SVM is used, the feature data is standardized to have mean zero and unit variance and the members of a training population are randomly divided into a training set and a test set. For example, in one embodiment, two thirds of the members of the training population are placed in the training set and one third of the members of the training population are placed in the test set. The observed values for a combination of observables in the training set are used to train the SVM. Then the ability for the trained SVM to correctly classify members in the test set is determined. In some embodiments, this computation is performed several times for a given combination of spectral features. In each iteration of the computation, the members of the training population are randomly assigned to the training set and the test set. Then, the quality of the combination of observables is taken as the average of each such iteration of the SVM computation.

XIII. Evolutionary Methods

Inspired by the process of biological evolution, evolutionary methods of decision rule design employ a stochastic search for a decision rule. In broad overview, such methods create several decision rules—a population—from a combination of observables in the training set. Observables in the training set are, for example, values of specific pixels, patterns of values of specific groups of pixels, values of specific measured wavelengths or any other form of observable data that is directly present in the spectral data and/or that can be derived from the spectral data. Each decision rule varies somewhat from the other. Next, the decision rules are scored on observable measured across the training population. In keeping with the analogy with biological evolution, the resulting (scalar) score is sometimes called the fitness. The decision rules are ranked according to their score and the best decision rules are retained (some portion of the total population of decision rules). Again, in keeping with biological terminology, this is called survival of the fittest. The decision rules are stochastically altered in the next generation—the children or offspring. Some offspring decision rules will have higher scores than their parent in the previous generation, some will have lower scores. The overall process is then repeated for the subsequent generation: the decision rules are scored and the best ones are retained, randomly altered to give yet another generation, and so on. In part, because of the ranking, each generation has, on average, a slightly higher score than the previous one. The process is halted when the single best decision rule in a generation has a score that exceeds a desired criterion value. More information on evolutionary methods is found in, for example, Duda, *Pattern Classification*, Second Edition, 2001, John Wiley & Sons, Inc, which is hereby incorporated by reference herein in its entirety.

XIV. Additional Embodiments

Additional methods for processing spectral data for use in tissue characterization may be applied either at the hyperspectral image stage 102 or at the contact probe stage 107. For example, a subset of data may be identified among the hyperspectral data from the plurality of regions measured in step 102. The subset of data may be identified because it is affected by glare, shadow, mucus, a smoke tube, and/or speculum. The regions of the subject's skin that correspond to the subset of data will also be identified. The affected subset of data will either be disregarded in future processing, or weighted for partial consideration in future processing, or fully processed like the rest of the data set. In some embodiments, the regions of skin corresponding to the affected subset of data are measured in a repeat instance of step 102 after the obstruction has been removed or treated. In some embodiments, the region of skin corresponding to the affected subset of data is measured in an instance of step 107 and/or one more repeat instances of step 107 of FIG. 1A after the obstruction has been removed or treated.

In other embodiments, the subset set of data may be identified in data collected in each region (including the suspect region) and used as control in regression analysis. In one example, a randomly selected subset set of data is not subjected to data modification and is used as an internal standard to calibrate and control the overall quality of data processing. It is also possible to spite the same region of a subject's skin into subregions and process the subsets by different methods. Results from the individual subsets can then be combined or modified in order to determine an overall result, for example, an image that corresponds to the entire region. The data splitting may also be performed randomly or based on sub-regional locations.

Additional exemplary methods for data processing include but are not limited to, for example, U.S. Pat. No. 7,282,723 to Schomacker issued on Oct. 16, 2007 (Methods and Apparatus for Processing Spectral data for use in Tissue Characterization); U.S. patent application to Garini et al., published as Publication No. 2003/0215791 A1 (Method of and System for Multiplexed Analysis by Spectral Imaging); and U.S. Pat. No. 7,219,086 B2 to Geshwind et al. issued on May 15, 2007 (System and Method for Hyper-Spectral Analysis); each of which is hereby incorporated by reference herein in its entirety.

The aforementioned methods for tissue characterization may be used individually or in a combination with each other.

D. Combining Decision Rules to Classify a Subject

In some embodiments, multiple decision rules are used to identify a feature of biological interest in a subject's skin (e.g., a lesion), to characterize such a feature (e.g., to identify a type of skin lesion), or to detect a change in a skin lesion over time. For instance, a first decision rule may be used to determine whether a subject has a skin lesion and, if the subject does have a skin lesion, a second decision rule may be used to determine whether a subject has a specific type of skin lesion. Advantageously, and as described above, in some instances such decision rules can be trained using a training data set that includes hyperspectral imaging data from subjects with known phenotype (e.g., lesions of known type). As such, in some embodiments of the present disclosure, a particular decision rule is not executed unless model preconditions associated with the decision rule have been satisfied.

For example, in some embodiments, a model precondition specifies that a first decision rule that is indicative of a broader biological sample class (e.g., a more general phenotype) than a second decision rule must be run before the second decision rule, indicative of a narrower biological sample class, is run. To illustrate, a model precondition of a second decision rule that is indicative of a particular form of skin lesion could require that a first decision rule, that is indicative of skin lesion generally, test positive prior to running the second decision rule. In some embodiments, a model precondition includes a requirement that another decision rule in a plurality of decision rules be identified as negative, positive, or indeterminate prior to testing another decision rule. A few additional examples of how preconditions can be used to arrange decision rules into hierarchies follow.

In a first example, the preconditions of decision rule B require that decision rule A have a specific result before decision rule B is run. It may well be the case that decision rule A is run, yet fails to yield the specific result required by decision rule B. In this case, decision rule B is never run. If, however, decision rule A is run and yields the specific result required by decision rule B, then decision rule B is run. This example can be denoted as:

if (A=result), then B can be run.

In a second example, the preconditions of decision rule C require that either decision rule A has a specific result or that decision rule B has a specific result prior to running decision rule C. This example can be denoted as:

if ((A=first result) or (B=second result)), then C can be run.

To illustrate, a model C can require that decision rule A be run and test positive for a skin lesion type A or that decision rule B be run and test positive for skin lesion type B, before decision rule C is run. Alternatively, the preconditions of decision rule C could require that both decision rule A and decision rule B achieve specific results:

if ((A=first result) and (B=second result)), then C can be run.

In another example, the preconditions of decision rule D require that decision rule C has a specific result before decision rule D is run. The preconditions of decision rule C, in turn, require that decision rule A has a first result and that decision rule B has a second result before decision rule C is run. This example can be denoted as:

If ((A=first result) and (B=second result)), then C can be run

If (C=third result), then D can be run.

These examples illustrate the advantages that model preconditions provide. Because of the preconditions of the present application, decision rules can be arranged into hierarchies in which specific decision rules are run before other decision rules are run. Often, the decision rules run first are designed to classify a subject into a broad biological sample class (e.g., broad phenotype). Once the subject has been broadly classified, subsequent decision rules are run to refine the preliminary classification into a narrower biological sample class (e.g., a specific skin lesion type or state).

E. Sharing Hyperspectral Images with Third Parties

Because hyperspectral data cubes and the raw output of other types of sensors/cameras can contain a tremendous amount of information, sharing such data with third parties can be impeded by finite transfer rates and/or finite storage space. However, because not all of the information in hyperspectral data cubes and/or raw sensor output is useful in characterizing a medical condition, the medical information within that data can usefully be shared with third parties in the form of "outline" or "shape" files that can be overlaid against conventional images of the subject. The "outline" files can indicate the location and boundary of the medical condition, and can include a description of the medical condition. In some embodiments, the "outline" files include an intensity map generated by the image constructor described above. A frame of reference for the file (e.g., the location on the subject's body to which the file corresponds) can also be transmitted to the third party.

4. Other Embodiments

The systems and methods described herein can be used to determine whether the subject has a wide variety of medical conditions. Some examples include, but are not limited to: abrasion, alopecia, atrophy, av malformation, battle sign, bullae, burrow, basal cell carcinoma, burn, candidal diaper dermatitis, cat-scratch disease, contact dermatitis, cutaneous larva migrans, cutis marmorata, dermatoma, ecchymosis, ephelides, erythema infectiosum, erythema multiforme, eschar, excoriation, fifth disease, folliculitis, graft vs. host disease, guttate, guttate psoriasis, hand, foot and mouth disease, Henoch-Schonlein purpura, herpes simplex, hives, id reaction, impetigo, insect bite, juvenile rheumatoid arthritis, Kawasaki disease, keloids, keratosis pilaris, Koebner phenomenon, Langerhans cell histiocytosis, leukemia, lichen *striatus*, lichenification, livedo *reticularis*, lymphangitis, measles, meningococcemia, molluscum contagiosum, neurofibromatosis, nevus, poison ivy dermatitis, psoriasis, scabies, scarlet fever, scar, seborrheic dermatitis, serum sickness, Shagreen plaque, Stevens-Johnson syndrome, strawberry tongue, swimmers' itch, telangiectasia, tinea capitis, tinea corporis, tuberous sclerosis, urticaria, varicella, varicella zoster, wheal, xanthoma, zosteriform, basal cell carcinoma, squamous cell carcinoma, malignant melanoma, dermatofibrosarcoma protuberans, Merkel cell carcinoma, and Kaposi's sarcoma.

Other examples include, but are not limited to: tissue viability (e.g., whether tissue is dead or living, and/or whether it is predicted to remain living); tissue ischemia; malignant cells or tissues (e.g., delineating malignant from benign tumors, dysplasias, precancerous tissue, metastasis); tissue infection and/or inflammation; and/or the presence of pathogens (e.g., bacterial or viral counts). Some embodiments include differentiating different types of tissue from each other, for example, differentiating bone from flesh, skin, and/or vasculature. Some embodiments exclude the characterization of vasculature.

The levels of certain chemicals in the body, which may or may not be naturally occurring in the body, can also be characterized. For example, chemicals reflective of blood flow, including oxyhemoglobin and deoxyhemoglobin, myoglobin, and deoxymyoglobin, cytochrome, pH, glucose, calcium, and any compounds that the subject may have ingested, such as illegal drugs, pharmaceutical compounds, or alcohol.

Some embodiments include a distance sensor (not shown) that facilitates positioning the subject at an appropriate distance from the sensor and/or projector. For example, the system 200 can include a laser range finder that provides a visible and/or audible signal such as a light and/or a beep or alarm, if the distance between the system and the subject is not suitable for obtaining light from and/or projecting light onto the subject. Alternately, the laser range finder may provide a visible and/or audible signal if the distance between the system and the subject is suitable.

An aspect provides a method of diagnosing a medical condition in subject, the subject having a plurality of regions. The method comprises: (A) resolving light obtained from each region of skin in the plurality of regions of skin into a corresponding spectrum, thereby constructing a plurality of spectra. The method further comprises (B) identifying a suspect region of skin in the plurality of regions of skin by obtaining a first indication that a first spectrum in the plurality of spectra that corresponds to the suspect region includes an indicia of themedical condition being present in the suspect region. The method further comprises (C) collecting, after the identifying (B), a measurement of the suspect region using a contact probe module thereby obtaining a second indication that the medical condition is present in the suspect region. The contact probe module is configured to obtain a signal from the suspect region. In some embodiments, the second indication is made based on comparison between the measurement and a stored measurement signature corresponding to the medical condition. In some embodiments the signal is an electrical signal, a magnetic signal, a thermal signal, a mechanical signal, or an optical signal. In some embodiments, the method further comprises (D) displaying an indicator representing the presence of the medical condition in the suspect region. In some alternative embodiments, the method further comprises (D) outputting an indicator representing the presence of the medical condition in the suspect region to a user, a user interface device, or a monitor; or outputting an indicator representing the presence of the medical condition in the suspect region in user readable form to a computer readable storage medium or a local or remote computer system; or displaying an indicator representing the presence of the medical condition in the suspect region.

Another aspect provides a method of diagnosing a medical condition in a subject, the subject having a plurality of regions. The method comprises (A) identifying a suspect region of skin in the plurality of regions of skin by obtaining a first indication that a first spectrum in a plurality of spectra that corresponds to the suspect region includes an indicia of a medical condition being present in the suspect region. The plurality of spectra is constructed by resolving light from each region of skin in the plurality of regions of skin into a corresponding spectrum. The first indication is made based on a comparison to the first spectrum to a stored predetermined spectral signature corresponding to the medical condition. The method further comprises (B) collecting, after the identifying (A), a measurement of the suspect region using a contact probe module thereby obtaining a second indication that the medical condition is present in the suspect region. The contact probe module is configured to obtain a signal from the suspect region. The second indication is made based on comparison between the signal and a stored measurement signature corresponding to the medical condition. In some embodiments, the signal is an electrical signal, a magnetic signal, a thermal signal, a mechanical signal, or an optical signal. In some embodiments, the method further comprises (C) displaying an indicator representing the presence of the medical condition in the suspect region. In some alternative embodiments, the method further comprises (C) outputting an indicator representing the presence of the medical condition in the suspect region to a user, a user interface device, or a monitor; or outputting an indicator representing the presence of the medical condition in the suspect region in user readable form to a computer readable storage medium or a local or remote computer system; or displaying an indicator representing the presence of the medical condition in the suspect region.

Another aspect provides a method of diagnosing a medical condition in subject, the subject having a plurality of regions. the method comprises (A) collecting a measurement of a suspect region using a contact probe module thereby obtaining an indication that a medical condition is present in the suspect region, where the suspect region is identified from the plurality of regions of skin by obtaining a first indication that a first spectrum in a plurality of spectra that corresponds to the suspect region includes an indicia of the medical condition being present in the suspect region. The plurality of spectra is constructed by resolving light from each region of skin in the plurality of regions of skin into a corresponding spectrum. The first indication is made based on a comparison to the first spectrum to a stored predetermined spectral signature corresponding to the medical condition. The contact probe module is configured to obtain a signal from the suspect region. The second indication is made based on comparison between the measurement and a stored measurement signature corresponding to the medical condition. In some embodiments, the signal is an electrical signal, a magnetic signal, a thermal signal, a mechanical signal, or an optical signal. In some embodiments, the method further comprises displaying an indicator representing the presence of the medical condition in the suspect region. In some alternative embodiments, the method further comprises outputting an indicator representing the presence of the medical condition in the suspect region to a user, a user interface device, or a monitor; or outputting an indicator representing the presence of the medical condition in the suspect region in user readable form to a computer readable storage medium or a local or remote computer system; or displaying an indicator representing the presence of the medical condition in the suspect region.

Another aspect provides a method of diagnosing a medical condition in a subject, the method comprising (A) obtaining, at a first distance from the subject, light from each region of a first plurality of regions of the subject. The method further comprises (B) resolving the light obtained from each region of the first plurality of regions into a corresponding spectrum, thereby constructing a first plurality of spectra. The method further comprises (C) determining, based on a spectral characteristic present in a subset of the first plurality of regions, a second distance from the subject allowing for closer examination of the subset. The method further comprises (D) obtaining, at a second distance from the subject, light from each region of a second plurality of regions of the subject, the second plurality of regions including the subset. The method further comprises (E) resolving the light obtained from each region of the second plurality of regions into a corresponding spectrum, thereby constructing a second plurality of spectra. The method further comprises (F) identifying a suspect region of skin in the plurality of regions of skin by obtaining a first indication and a second indication. In some instances the first indication represents that a first spectrum in the first plurality of spectra that corresponds to the suspect region includes an indicia of the medical condition being present in the suspect region. In some instance the first indication is made based on a comparison to the first spectrum to a stored predetermined spectral signature corresponding to the medical condition. In some instances, the second indication represents that a second spectrum in the second plurality of spectra that corresponds to the suspect region includes an indicia of the medical condition being present in the suspect region. In some instance, the second indication is made based on a comparison to the second spectrum to a stored predetermined spectral signature corresponding to the medical condition. The method further comprises (G) collecting, after the identifying (F), a measurement of the suspect region using a contact probe module thereby obtaining a third indication that the medical condition is present in the suspect region. In some instances, the contact probe module is configured to obtain a signal from the suspect region. In some instances, the third indication is made based on comparison between the measurement and a stored measurement signature corresponding to the medical condition. In some instances, the signal is an electrical signal, a magnetic signal, a thermal signal, a mechanical signal, or an optical signal. In some embodiments, the method further comprises (H) displaying an indicator representing the presence of the medical condition in the suspect region. In some alternative embodiments, the method further comprises (H) outputting an indicator representing the presence of the medical condition in the suspect region to a user, a user interface device, or a monitor; or outputting an indicator representing the presence of the medical condition in the suspect region in user readable form to a computer readable storage medium or a local or remote computer system; or displaying an indicator representing the presence of the medical condition in the suspect region.

Another aspect provides a method of characterizing a medical condition in a subject, the subject having a plurality of regions. The method comprises (A) resolving, at a first time, light obtained from each region of the plurality of regions into a corresponding spectrum, thereby creating a first plurality of spectra. The method further comprises (B) storing the spectra corresponding to the first time. The method further comprises (C) resolving, at a second time subsequent to the first time, light obtained from each region of the plurality of regions into a corresponding spectrum, thereby creating a second plurality of spectra. The method further comprises (D) identifying a suspect region among the plurality of regions based on a comparison of the second plurality of spectra corresponding to the second time to the first plurality of spectra corresponding to the first time. The method further comprises (E) collecting, after the identifying (D), a measurement of the suspect region using a contact probe module thereby obtaining a third indication that the medical condition is present in the suspect region. In some embodiments the contact probe module is configured to obtain a signal from the suspect region. In some embodiments the third indication is made based on comparison between the measurement and a stored measurement signature corresponding to the medical condition. In some embodiments the signal is an electrical signal, a magnetic signal, a thermal signal, a mechanical signal, or an optical signal. In some embodiments, the method further comprises (F) displaying an indicator representing the presence of the medical condition in the suspect region. In some alternative embodiments, the method further comprises (F) outputting an indicator representing the presence of the medical condition in the suspect region to a user, a user interface device, or a monitor; or outputting an indicator representing the presence of the medical condition in the suspect region in user readable form to a computer readable storage medium or a local or remote computer system; or displaying an indicator representing the presence of the medical condition in the suspect region.

The illumination subsystem 210, sensor subsystem 230, processor subsystem 250, and projection subsystem 270 can be co-located (e.g., all enclosed in a common housing). Alternatively, a first subset of the subsystems can be co-located, while a second subset of the subsystems are located separately from the first subset, but in operable communication with the first subset. For example, the illumination, sensing, and projection subsystems 210, 230, 270 can be co-located within a common housing, and the processing subsystem 250 located separately from that housing and in operable communication with the illumination, sensing, and projection subsystems. Or, each of the subsystems can be located separately from the other subsystems. Note also that storage 240 and storage 252 can be regions of the same device or two separate devices, and that processor 238 of the sensor subsystem may perform some or all of the functions of the spectral analyzer 254 and/or the image constructor 256 of the processor subsystem 250.

Note also that although illumination subsystem 210 is illustrated as irradiating an area 201 that is of identical size to the area from which sensor subsystem 230 obtains light and upon which projection subsystem 270 projects the image, the areas need not be of identical size. For example, illumination subsystem 210 can irradiate an area that is substantially larger than the region from which sensor subsystem 230 obtains light and/or upon which projection subsystem 270 projects the image. Also, the light from projection subsystem 270 may irradiate a larger area than sensor subsystem 230 senses, for example in order to provide an additional area in which the subsystem 270 projects notations and/or legends that facilitate the inspection of the projected image. Alternately, the light from projection subsystem 270 may irradiate a smaller area than sensor subsystem 230 senses.

Although illumination subsystem 210, sensor subsystem 230, and projection subsystem 270 are illustrated as being laterally offset from one another, resulting in the subject being irradiated with light coming from a different direction than the direction from which the sensor subsystem 230 obtains light, and a different direction than the direction from which the projection subsystem 270 projects the image onto the subject. As will be apparent to those skilled in the art, the system can be arranged in a variety of different manners that will allow the light to/from some or all of the components to be collinear, e.g., through the use of dichroic mirrors, polarizers, and/or beamsplitters. Or, multiple functionalities can be performed by a single device. For example, the projection subsystem 270 could also be used as the irradiation subsystem 210, with timers used in order to irradiate the subject and project the image onto the subject at slightly offset times.

In some embodiments, the spectral analyzer 254 has access to spectral information (e.g., characteristic wavelength bands and/or normalized reflectances $R_N(k)$) associated with a wide variety of medical conditions, physiological characteristics, and/or chemicals. This information can be stored, for example, in storage 252, or can be accessed via the Internet (interface not shown). In some embodiments, the spectral analyzer has access to spectral information for a narrow subset of medical conditions, physiological features, or chemicals, that is, the system 200 is constructed to address only a particular kind of condition, feature, or chemical.

The present invention can be implemented as a computer program product that includes a computer program mechanism embedded in a computer-readable storage medium. Further, any of the methods disclosed herein can be implemented in one or more computers or other forms of apparatus. Examples of apparatus include but are not limited to the devices depicted in FIGS. 2 and 6. Further still, any of the methods disclosed herein can be implemented in one or more computer program products. Some embodiments disclosed herein provide a computer program product that encodes any or all of the methods disclosed herein. Such methods can be stored on a CD-ROM, DVD, magnetic disk storage product, or any other computer-readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices.

Some embodiments provide a computer program product that contains any or all of the program modules shown in the Figures. These program modules can be stored on a CD-ROM, DVD, magnetic disk storage product, or any other computer-readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices.

Additional Embodiments

The following includes description of additional optional embodiments of components of the hyperspectral apparatus and of methods for data collection and data analysis. It will be understood to one of ordinary skill in the art that the additional embodiments described therein are applicable to both the hyperspectral image devices without one or more contact probes and to the hyperspectral image devices with one or more contact probes, unless otherwise specified.

In some embodiments, the hyperspectral apparatus has at least one operating parameter that is a sensor control, an exposure setting, a frame rate, or an integration rate. In some embodiments, the light source of the in the hyperspectral apparatus is controlled by the control software module. In some embodiments, the hyperspectral apparatus is portable and further comprises one or more batteries for powering the hyperspectral sensor, the control computer and the light source. In some embodiments, the hyperspectral apparatus further comprises a scan mirror to provide simulated motion for a hyperspectral scan of the skin of the subject.

In some embodiments, the hyperspectral sensor is mounted on a tripod. In some embodiments, the tripod is a fixed sensor tripod or a fixed sensor tripod on wheels. In some embodiments, the hyperspectral sensor is mounted on a mobile rack.

In some embodiments, the hyperspectral apparatus further comprises a trained data analysis algorithm, which is stored in the computer readable memory, for identifying a region of the subject's skin of biological interest using an image obtained by the apparatus.

In some embodiments, the hyperspectral apparatus further comprises a trained data analysis algorithm, which is stored in the computer readable memory, for characterizing a region of the subject's skin of biological interest using an image obtained by the apparatus.

In some embodiments, the hyperspectral apparatus further comprises a trained data analysis algorithm, which stored in the computer readable memory, for determining a portion of a hyperspectral data cube that contains information about a biological insult in the subject's skin.

In the preceding embodiments, the trained data analysis algorithm is a trained neural network, a trained support vector machine, a decision tree, or a multiple additive regression tree.

In some embodiments, the hyperspectral apparatus further comprises an alternative sensor other than a hyperspectral sensor. The alternative sensor is a digital camera, a LIDAR sensor, or a terahertz sensor.

In some embodiments, the hyperspectral apparatus further comprises a fusion module, stored in the computer readable memory, for fusing an image of a portion of the skin of the subject from the other sensor and an image of a portion of the skin of the subject from the hyperspectral sensor. In some embodiments, the fusion module comprises instructions for color coding or greyscaling data from the image of a portion of the skin of the subject from the hyperspectral sensor onto the image of a portion of the skin of the subject from the other sensor. In some embodiments, the fusion module comprises instructions for color coding or greyscaling data from the image of a portion of the skin of the subject from the other sensor onto the image of a portion of the skin of the subject from the hyperspectral sensor. In some embodiments, the fusion module comprises instructions for color coding or greyscaling data from the image of a portion of the skin of the subject from the other sensor as well as color coding or greyscaling data from the image of a portion of the skin of the subject from the hyperspectral sensor.

In some embodiments, the hyperspectral apparatus further comprises an integrated display for displaying data from the hyperspectral sensor and a value of the at least one operating parameter that is controlled by the control computer. In some embodiments, the integrated display further displays the probabilistic presence of a biological insult to the skin of the subject.

In some embodiments, the hyperspectral apparatus further comprises a spectral analyzer module, which is stored in the computer readable media. The spectral analyzer module comprises instructions for determining a boundary of an image of a biological insult in the hyperspectral image. In some embodiments, the boundary of the image of the biological insult is manually determined by a user. In some embodiments, the boundary of the image of the biological insult is determined by a trained data analysis algorithm.

In some embodiments, the hyperspectral apparatus further comprises a communications module that comprises instructions for communicating the boundary of the image or the biological insult to a local or remote computer over a network connection. In some embodiments, the communications module further comprises instructions for communicating a frame of reference of the skin of the subject with the boundary of the image of the biological insult to the local or remote computer over the network connection.

In one aspect, the present application provides a method of diagnosing a medical condition in a subject, the subject having a plurality of regions. In some embodiments, the method comprises a) resolving light obtained from each region of the plurality of regions into a corresponding spectrum; b) obtaining, based on a stored spectral signature corresponding to the medical condition, a probability that each spectrum includes indicia of the medical condition being present in the corresponding region; c) displaying, if the probability exceeds a first pre-defined threshold, an indicator representing the probable presence of the medical condition in the corresponding region; d) accepting user input setting a second pre-defined threshold; and e) displaying, if the probability exceeds the second pre-defined threshold, an indicator representing the probable presence of the medical condition in the corresponding region.

In one aspect, the present application provides a method of diagnosing a medical condition in a subject, the subject having a plurality of regions. In some embodiments, the method comprises: a) resolving light obtained from each region of the plurality of regions into a corresponding spectrum; b) obtaining, based on a stored spectral signature corresponding to the medical condition, a probability that each spectrum includes indicia of the medical condition being present in the corresponding region; c) displaying, if the probability exceeds a first pre-defined threshold, an indicator representing the probable presence of the medical condition in the corresponding region; and d) displaying at least one of a type of the medical condition, a category of the medical condition, an age of the medical condition, a boundary of the medical condition, and a new area of interest for examination.

In one aspect, the present application provides a method of diagnosing a medical condition in a subject, the subject having a plurality of regions. In some embodiments, the method comprises: a) obtaining, at a first distance from the subject, light from each region of a first plurality of regions of the subject; b) resolving the light obtained from each region of the first plurality of regions into a corresponding spectrum; c) determining, based on a spectral characteristic present in a subset of the first plurality of regions, a second distance from the subject allowing for closer examination of the subset; d) obtaining, at a second distance from the subject, light from each region of a second plurality of regions of the subject, the second plurality of regions including the subset; e) resolving the light obtained from each region of the second plurality of regions into a corresponding spectrum; f) obtaining, based on a stored spectral signature corresponding to the medical condition, a probability that each spectrum includes indicia of the medical condition being present in the corresponding region; and g) displaying, if the probability exceeds a pre-defined threshold, an indicator representing the probable presence of the medical condition in the corresponding region.

In one aspect, the present application provides a method of diagnosing a medical condition in a subject, the subject having a plurality of regions. In some embodiments, the method comprises: a) resolving, at a first time, light obtained from each region of the plurality of regions into a corresponding spectrum; b) storing the spectra corresponding to the first time; c) resolving, at a second time subsequent to the first time, light obtained from each region of the plurality of regions into a corresponding spectrum; d) determining, based on a comparison of the spectra corresponding to the second time to the spectra corresponding to the first time, that the medical condition had been present at the first time although it had not been apparent at the first time; and e) displaying an indicator representing the probable presence of the medical condition in the subject.

In another aspect, the present application provides a hyperspectral apparatus comprising a contact probe module. The contact probe module is in electronic communication with the control computer and is configured to measure a region of interest of the skin of a subject that is identified based on an aspect of the hyperspectral image. Further, the contact probe module comprises a first probe head unit connected to a handle unit.

In some embodiments, the handle unit in the contact probe module of the hyperspectral apparatus is configured to receive a first probe head unit and a second probe head unit. The first probe head unit is a different type of probe head than the second probe head unit. In some embodiments, the contact probe module is configured to obtain more than one type of signal from the region of interest of the skin of the subject. In some embodiments, the contact probe module is configured to measure at least a first type of signal and a second type of signal. The first type of signal is different than the second type of signal.

In some embodiments, the contact probe module is configured to measure a region of interest of the skin of a subject at a plurality of different times.

In one aspect, the present application provides a method of diagnosing a medical condition of a subject using a contact probe module, where the subject has a plurality of regions of skin of interest. According to the method, light is first obtained from each region of skin in the plurality of regions of skin of interest and then resolved into a corresponding spectrum using a hyperspectral module, thereby constructing a plurality of spectra. Further, a suspect region of skin is identified in the plurality of regions of skin by obtaining a first indication that a first spectrum in the plurality of spectra that corresponds to the suspect region includes an indicia of a medical condition being present in the suspect region. After the identification, a measurement of the suspect region is collected using the contact probe module thereby obtaining a second indication that the medical condition is present in the suspect region. The contact probe module is configured to obtain a signal from the suspect region. An indicator representing the presence of the medical condition in the suspect region is then outputted to a user, a user interface device, or a monitor. Alternatively, an indicator representing the presence of the medical condition in the suspect region in user readable form is outputted to a computer readable storage medium or a local or remote computer system; or displaying an indicator representing the presence of the medical condition in the suspect region.

In some embodiments, the first indication is made based on a comparison between the first spectrum and a stored predetermined spectral signature corresponding to the medical condition. The stored predetermined spectral signature is obtained from a region that is known to have the medical condition.

In some embodiments, the first indication is made based on a comparison between the first spectrum and a stored predetermined spectral signature corresponding to the medical condition and the indication is made when the first spectrum shares a similarity to the stored predetermined spectral signature.

In some embodiments, the similarity is determined based on a similarity metric computed between the first spectrum and the stored predetermined spectral signature.

In some embodiments, the first indication is made based on a comparison between the first spectrum and a stored predetermined spectral signature corresponding to the medical condition and the second indication is made when the signal from the suspect region shares a similarity to the stored measurement signature. In some embodiments, the similarity is determined based on a similarity metric computed between the signal from the suspect region and the stored measurement signature.

In some embodiments, the first indication is made based on a comparison between the first spectrum and a stored predetermined spectral signature corresponding to the medical condition.

In some embodiments, the second indication is made based on comparison between the measurement and a stored measurement signature corresponding to the medical condition.

REFERENCES

All references cited herein are hereby incorporated by reference herein in their entirety and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments described herein are offered by way of example only, and the application is to be limited only by the terms of the appended claims, along with the full scope of equivalents to which the claims are entitled.

What is claimed:

1. An apparatus for analyzing the skin of a subject, the apparatus comprising:
   a hyperspectral sensor for obtaining a hyperspectral image of said subject over a spectrum of wavelengths, wherein the spectrum of wavelengths comprises a first wavelength and a second wavelength different than the first wavelength;
   a control computer for controlling the hyperspectral sensor, wherein the control computer is in electronic communication with the hyperspectral sensor and wherein the control computer controls at least one operating parameter of the hyperspectral sensor, and wherein the control computer comprises a processor unit and a computer readable memory;
   a control software module, stored in the computer readable memory and executed by the processor unit, the control software comprising instructions for controlling said at least one operating parameter of the hyperspectral sensor;
   a spectral calibrator module, stored in the computer readable memory and executed by the processor unit, the spectral calibrator module comprising instructions for applying a wave-length dependent spectral calibration standard constructed for the hyperspectral sensor to the hyperspectral image collected by the hyperspectral sensor, wherein the applying of a wave-length dependent spectral calibration standard constructed for the hyperspectral sensor to the hyperspectral image collected by the hyperspectral sensor comprises (i) obtaining a sensitivity of the hyperspectral sensor responsive to each wavelength in the spectrum of wavelengths, and (ii) calibrating the hyperspectral image using each sensitivity of the hyperspectral sensor responsive to each wavelength in the spectrum of wavelengths, wherein a first sensitivity of the hyperspectral sensor responsive to the first wavelength is different than a second sensitivity of the hyperspectral sensor responsive to the second wavelength; and
   a light source that illuminates the skin of the subject for the hyperspectral sensor.

2. The apparatus of claim 1, wherein the light source comprises a polarizer.

3. The apparatus of claim 2, wherein the hyperspectral sensor comprises a cross polarizer.

4. The apparatus of claim 1, wherein the hyperspectral sensor comprises a sensor head, and wherein the control software module comprises instructions for moving the sensor head through a range of distances relative to the subject, including a first distance that permits a wide field view of a portion of the subject's skin, and a second distance that permits a detailed view of a portion of the subject's skin.

5. The apparatus of claim 1, the apparatus further comprising:
   a spectral analyzer module stored in the computer readable memory, the spectral analyzer module comprising instructions for comparing a spectrum acquired using the hyperspectral sensor to a signature in a plurality of spectral signatures corresponding to characterized human lesions.

6. The apparatus of claim 1, the apparatus further comprising:
   a storage module, stored in the computer readable media, wherein the storage module comprises a plurality of spectra of the subject's skin taken at different time points; and
   a spectral analyzer module, stored in the computer readable media, wherein the spectral analyzer module comprises instructions for using the plurality of spectra to form a normalization baseline of the skin.

7. The apparatus of claim 6, wherein the different time points span one or more contiguous years up to the life time of the subject.

8. The apparatus of claim 6, wherein the spectral analyzer module further comprises instructions for analyzing the plurality of spectra to determine a time when a biological insult originated.

9. The apparatus of claim 8, wherein the biological insult is a lesion.

10. The apparatus of claim 1, the apparatus further comprising a sensor other than a hyperspectral sensor.

11. The apparatus of claim 10, wherein the other sensor is a digital camera, a LIDAR sensor, or a terahertz sensor.

12. The apparatus of claim 1, further comprising:
   a contact probe module in electronic communication with the control computer, wherein the contact probe module is configured to measure a region of interest of the skin of said subject that is identified based on an aspect of the hyperspectral image, and wherein said contact probe module comprises a first probe head unit connected to a handle unit.

13. The apparatus of claim 12, wherein said contact probe module further comprises a connector unit connected to the handle unit.

14. The apparatus of claim 12, wherein said first probe head unit is configured to obtain a signal from a region of interest of the skin of the subject, wherein said signal is an electrical, a magnetic, a thermal, a mechanical, a radiometric, a photometric, or an optical signal.

15. The apparatus of claim 12, wherein said first probe head unit is an electrical probe, a magnetic probe, a thermal probe, a mechanical probe, a radiometric probe, a photometric probe or an optical probe.

16. The method of claim 1, wherein the wave-length dependent spectral calibration standard constructed for the hyperspectral sensor is obtained by comparing measured reflection of light from a standard that is measured by the hyperspectral sensor to expected reflection of light from the standard.

* * * * *